(12) United States Patent
Smith et al.

(10) Patent No.: US 7,919,095 B2
(45) Date of Patent: Apr. 5, 2011

(54) ANTI-IL-6 MONOCLONAL ANTIBODIES

(75) Inventors: Ernest S. Smith, Ontario, NY (US); Wei Wang, Pittsford, NY (US)

(73) Assignee: Vaccinex, Inc., Rochester, NY (US)

( * ) Notice: Subject to any disclaimer, the term of this patent is extended or adjusted under 35 U.S.C. 154(b) by 430 days.

(21) Appl. No.: 11/882,751

(22) Filed: Aug. 3, 2007

(65) Prior Publication Data

US 2008/0075726 A1 Mar. 27, 2008

Related U.S. Application Data

(60) Provisional application No. 60/835,107, filed on Aug. 3, 2006.

(51) Int. Cl.
*A61K 39/395* (2006.01)
*C07K 16/24* (2006.01)

(52) U.S. Cl. .............. 424/145.1; 424/141.1; 530/388.1; 530/388.23

(58) Field of Classification Search .................. None
See application file for complete search history.

(56) References Cited

U.S. PATENT DOCUMENTS

| | | | |
|---|---|---|---|
| 5,618,700 A | 4/1997 | Novick et al. | |
| 5,693,780 A | 12/1997 | Newman et al. | |
| 5,856,135 A | 1/1999 | Tsuchiya et al. | |
| 5,888,510 A | 3/1999 | Kishimoto et al. | |
| 6,083,501 A | 7/2000 | Miyata et al. | |
| 6,086,874 A | 7/2000 | Yoshida et al. | |
| 6,121,423 A | 9/2000 | Tsuchiya et al. | |
| 6,248,516 B1 | 6/2001 | Winter et al. | |
| 6,632,927 B2 * | 10/2003 | Adair et al. ............... | 530/387.3 |
| 2002/0051787 A1 | 5/2002 | Prince et al. | |
| 2002/0123057 A1 | 9/2002 | Zauderer et al. | |
| 2002/0168360 A1 | 11/2002 | Dingivan et al. | |
| 2003/0044406 A1 | 3/2003 | Dingivan et al. | |
| 2004/0028681 A1 | 2/2004 | Ito et al. | |
| 2004/0161426 A1 | 8/2004 | Trikha et al. | |
| 2005/0032175 A1 | 2/2005 | Stahl et al. | |
| 2005/0100550 A1 | 5/2005 | Trikha et al. | |
| 2005/0180974 A1 | 8/2005 | Shafer | |
| 2005/0196755 A1 | 9/2005 | Zauderer et al. | |
| 2006/0134113 A1 | 6/2006 | Mihara | |
| 2006/0165696 A1 | 7/2006 | Okano et al. | |
| 2006/0228416 A1 | 10/2006 | Faure et al. | |
| 2006/0257401 A1 | 11/2006 | Stassi et al. | |
| 2006/0257407 A1 | 11/2006 | Chen et al. | |
| 2006/0275294 A1 | 12/2006 | Omoigui | |
| 2006/0292147 A1 | 12/2006 | Yoshizaki et al. | |
| 2007/0009527 A1 | 1/2007 | Muyldermans | |
| 2007/0060521 A1 | 3/2007 | Jove et al. | |

FOREIGN PATENT DOCUMENTS

| | | |
|---|---|---|
| DE | 39 39 706 C1 | 3/1991 |
| EP | 0 312 996 A2 | 4/1989 |
| EP | 0 410 813 A1 | 7/1989 |
| EP | 0 399 429 A1 | 11/1990 |
| EP | 0 783 893 A1 | 7/1997 |
| EP | 0 800 829 A1 | 10/1997 |
| EP | 1 536 012 A1 | 6/2005 |
| EP | 1 712 241 A1 | 10/2006 |
| WO | WO 98/36061 A2 | 8/1998 |
| WO | WO 98/42377 A1 | 10/1998 |
| WO | WO 99/47170 A1 | 9/1999 |
| WO | WO 99/64070 A1 | 12/1999 |
| WO | WO 00/10607 A1 | 3/2000 |
| WO | WO 01/62287 A1 | 8/2001 |
| WO | WO 02/34292 A1 | 5/2002 |
| WO | WO 02/080969 A1 | 10/2002 |
| WO | WO 2004/020633 A1 | 3/2004 |
| WO | WO 2004/039826 A1 | 5/2004 |
| WO | WO 2004/045507 A2 | 6/2004 |
| WO | WO 2004/073741 A1 | 9/2004 |
| WO | WO 2004/096273 A1 | 11/2004 |
| WO | WO 2005/023193 A2 | 3/2005 |
| WO | WO 2005/080429 A2 | 9/2005 |
| WO | WO 2006/066088 A2 | 6/2006 |
| WO | WO 2006/119767 A2 | 11/2006 |

OTHER PUBLICATIONS

Panka et al. Proc. Natl. Acad. Sci. USA vol. 85, pp. 3080-3084 (May 1988).*
Rudikoff et al. Proc. Natl. Acad. Sci. USA vol. 79, pp. 1979-1983 (Mar. 1982).*
Amit et al. Science, Vot. 233, pp. 747-753, (Aug. 1986).*
Mikayama et al. Proc. Natl. Acad. Sci. USA (1993), vol. 90, pp. 10056-10060.*
Voet et al. Biochemistry John Wiley & Sons, Inc., (199), pp. 126-128 and 228-234.*
Bataille, R., et al., "Biologic Effects of Anti-Interleukin-6 Murine Monoclonal Antibody in Advanced Multiple Myeloma," *Blood* 86:685-691, The American Society of Hematology (1995).
Bender, P.K., and Larson, T.J., "Chap. 24. PC/GENE: Database Searches," in *Methods in Molecular Biology*, vol. 24:*Computer Analysis of Sequence Data, Part I*, Griffin, A.M., and Griffin, H.G., eds., Humana Press Inc., Totowa, NJ, pp. 289-306 (1994). Blay, J.-Y., et al., "Role of Interleukin-6 in the Paraneoplastic Inflammatory Syndrome Associated with Renal-Cell Carcinoma," *Int. J. Cancer* 72:424-430, Wiley-Liss, Inc. (1997).
Brakenhoff, J.P.J., et al., "Structure-Function Analysis of Human IL-6. Epitope Mapping of Neutralizing Monoclonal Antibodies with Amino- and Carboxyl-Terminal Deletion Mutants," *J. Immunol.* 145:561-568, The American Association of Immunologists (1990).
Cahlin, C., et al., "Experimental Cancer Cachexia: The Role of Host-derived Cytokines Interlukin (IL)-6, IL-12, Interferon-γ, Tumor Necrosis Factor α Evaluated in Gene Knockout, Tumor-bearing Mice on C57 B1 Background and Eicosanoid-dependent Cachexia," *Cancer Res.* 60:5488-5493, American Association for Cancer Research, Inc. (2000).

(Continued)

*Primary Examiner* — Prema Mertz
(74) *Attorney, Agent, or Firm* — Sterne, Kessler, Goldstein & Fox P.L.L.C.

(57) ABSTRACT

The present invention provides novel monoclonal antibodies that bind specifically to IL-6. The antibodies of the invention comprise a variable heavy chain (VH) region selected from any of the VH regions disclosed herein as well as amino acid variants thereof, and/or a variable light chain (VL) region selected from any of the VL regions disclosed herein as well as amino acid variants thereof. The invention also provides methods of treating diseases and disorders associated with IL-6 expression and/or activity.

9 Claims, 26 Drawing Sheets

OTHER PUBLICATIONS

Campbell, I.L., et al., "Neurologic disease induced in transgenic mice by cerebral overexpression of interleukin 6," *Proc. Natl. Acad. Sci. USA* 90:10061-10065, National Academy of Sciences (1993).

Carrillo, H., and Lipman, D., "The Multiple Sequence Alignment Problem in Biology," *SIAM J. Appl. Math.* 48:1073-1082, Society for Industrial and Applied Mathematics (1988).

Clark, S.P., et al., *Biocomputing Informatics and Genome Projects*, Smith, D.W., ed., Academic Press, New York, NY, pp. 28-31 (1993).

Cohen, B.I., and Cohen, F.E., "Chap. 7. Predictions of Protein Secondary and Tertiary Structure," in *Biocomputing Informatics and Genome Projects*, Smith, D.W., ed., Academic Press, New York, NY, pp. 203-232 (1994).

Cunnigham, B.C., and Wells, J.A., "High-Resolution Epitope Mapping of hGH—Receptor Interactions by Alanine-Scanning Mutagenesis," *Science* 244:1081-1085, American Association for the Advancement of Science (1989).

Dayhoff, M.O., et al., "A Model of Evolutionary Change in Proteins," *Atlas Protein Sequence and Structure* 5:345-352, The National Biomedical Research Foundation (1979).

Devereux, J., et al., "A comprehensive set of sequence analysis programs for the VAX," *Nucl. Acid. Res.* 12:387-395, IRL Press Limited, Oxford, England (1984).

Dölz, R., "Chap. 12. GCG: Analysis of Protein Sequences," in *Methods in Molecular Biology*, vol. 24:*Computer Analysis of Sequence Data, Part I*, Griffin, A.M., and Griffin, H.G., eds., Humana Press Inc., Totowa, NJ, pp. 143-157 (1994).

Emilie, D., et al., "Administration of an Anti-Interleukin-6 Monoclonal Antibody to Patients with Acquired Immunodeficiency Syndrome and Lymphoma: Effect on Lymphoma Growth and on B Clinical Symptoms," *Blood* 84:2472-2479, The American Society for Hematology (1994).

Friguet, B., et al., "Measurements of the True Affinity Constant in Solution of Antigen-Antibody Complexes by Enzyme-Linked Immunosorbent Assay," *J. Immunol. Meth.* 77:305-319, Elsevier Science Publishers B.V. (1985).

Foussat, A., et al., "Human interleukin-6 is in vivo an autocrine growth factor for human herpesvirus-8-infected maliganant B lymphocytes," *Eur. Cytokine Netw.* 10:501-508, John Libbey Eurotext Ltd. (1999).

Haddad, E., et al., "Treatment of B-lymphoproliferative disorder with a monoclonal anti-interleukin-6 antibody in 12 patients: a multicenter phase 1-2 clinical trial," *Blood* 97:1590-1597, The American Society of Hematology (2001).

Henikoff, S., and Henikoff, J.G., "Amino acid substitution matrices from protein blocks," *Proc. Natl. Acad. Sci. USA* 89:10915-10919, National Academy of Sciences (1992).

Henikoff, S., "Chap. 4. Comparative Sequence Analysis: Finding Genes," in *Biocomputing Informatics and Genome Projects*, Smith, D.W., ed., Academic Press, New York, NY, pp. 87-117 (1994).

Jakobovits, A., "Production of fully human antibodies by transgenic mice," *Curr. Opin. Biotech.* 6:561-566, Current Biology Ltd. (1995).

Kabat, E.A. et al., *Sequences of proteins of immunological interest*, 5th edition, U.S. Department of Health and Human Services, NIH publication 91-3242, pp. 1-22, 23-40, 103-148, 310-324, 647-709, 1138-1155, 1157-1171, 1229-1248, 1335-1343, 1571-1604, 2130-2154 (1991).

Lonberg, N., "Human antibodies from transgeneic animals," *Nat. Biotech.* 23:1117-1125, Nature Publishing Group (Sep. 2005).

May, L.T., et al., "Anti-β-interferon antibodies inhibit the increased expression of HLA-B7 mRNA in tumor necrosis factor-treated human fibroblasts: Structural studies of the $\beta_2$ interferon involved," *Proc. Natl. Acad. Sci. USA* 83:8957-8961, National Academy of Sciences (1986).

McCafferty, J., et al., "Phage antibodies: filamentous phage displaying antibody variable domains," *Nature* 348:552-554, Macmillan Magazines Ltd. (1990).

Merrifield, R.K., "Chap. 18. MicroGenie: Protein Analysis," in *Methods in Molecular Biology*, vol. 24:*Computer Analysis of Sequence Data, Part I*, Griffin, A.M., and Griffin, H.G., eds., Humana Press Inc., Totowa, NJ, pp. 227-235 (1994).

Morrison, S.L., et al., "Chimeric human antibody molecules: Mouse antigen-binding domains with human constant region domains," *Proc. Natl. Acad. Sci. USA* 81:6851-6855, National Academy of Sciences (1984).

Musselman, D.L., et al., "Higher Than Normal Plasma Interleukin-6 Concentrations in Cancer Patients with Depression: Preliminary Findings," *Am. J. Psychiatry.* 158:1252-1257, American Psychiatric Association (2001).

Needleman, S.B., and Wunsch, C.D., "A General Method Applicable to the Search for Similarities in the Amino Acid Sequence of Two Proteins," *J. Mol. Biol.* 48:443-453, Academic Press Inc. (1970).

Racadot, E., et al., "Clinical and immunological follow-up of patients with AIDS-associated Kaposi's sarcoma treated with an anti-IL-6 monoclonal antibody," *Cytokin. Mol. Ther.* 1:133-138, Martin Dunitz Ltd. (1995).

Rossi, J.F., et al., "Optimizing the use of anti-interleukin-6 monoclonal antibody with dexamethasone and 140mg/m$^2$ of melphalan in multiple myeloma: results of a pilot study including biological aspects," *Bone Marrow Transplant.* 36:771-779, Nature Publishing Group (Aug. 2005).

Saggio, I., et al., "Adenovirus-mediated gene transfer of a human IL-6 antagonist," *Gene Ther.* 4:839-845, Stockton Press (1997).

States, D.J., and Boguski, M.S., "Chap. 3. Similarity and Homology," in *Sequence Analysis Primer*, Gribskov, M., and Devereux, J., eds., Stockton Press, New York, NY, pp. 89-157 (1991).

Tirkha, M., et al., "Targeted Anti-Interleukin-6 Monoclonal Antibody Therapy for Cancer: A Review of the Rationale and Clinical Evidence," *Clin. Cancer Res.* 9:4653-4665, American Association for Cancer Research, Inc., (2003).

van Zannen, H.C.T., et al., "Endogenous Interleukin 6 Production in Multiple Myeloma Patients Treated with Chimeric Monoclonal Anti-IL6 Antibodies Indicates the Existence of a Positive Feed-back Loop," *J. Clin. Invest.* 98:1441-1448, The American Society for Clinical Investigation, Inc. (1996).

Vaughan, T.J., et al., "Human antibodies by design," *Nat. Biotech.* 16:535-539, Nature America Inc., (1998).

von Heinje, G., "Chap. 6. Sequence Similarities, Homologies, and Alignments," in *Sequence Analysis in Molecular Biology*, Harcourt Brace Jovanovich Inc., San Diego, CA, pp. 123-139 (1987).

Wendling, D., et al., "Treatment of Severe Rheumatoid Arthritis by Anti-Interleukin 6 Monoclonal Antibody," *J. Rheumatol.* 20:259-262, Journal of Rheumatology Publishing Co. Ltd. (1993).

Wijdenes, J., et al., "Human Recombinant Dimeric IL-6 Binds to its Receptor as Detected by Anti-IL-6 Monoclonal Antibodies," *Mol. Immunol.* 28:1183-1192, Pregamon Press plc (1991).

Beck, J.T., et al., "Brief Report: Alleviation of Systemic Manifestations of Castleman's Disease by Monoclonal Anti-Interleukin-6 Antibody," *New Eng. J. Med.* 330:602-605, Massachusetts Medical Society (1994).

Kishimoto, T., "Interleukin-6 and its Receptor in Autoimmunity," *J. Autoimmu.* 5 (*Suppl. A*):123-132, Academic Press Ltd. (1992).

Klein, B., et al., "Murine Anti-Interluekin-6 Monoclonal Antibody Therapy for a Patient with Plasma Cell Leukemia," *Blood* 78:1198-1204, The American Society for Hematology (1991).

Shimamura, T. et al., "Analysis of Interleukin 6 (IL-6)/IL-6 Receptor System Using Monoclonal Anti-IL-6 Antibodies," *Molec. Immunol.* 28:1155-1161, Pergamon Press plc, Great Britain (1991).

Wendling, D., "Combination Therapy of Anti-CD4 and Anti-IL6 Monoclonal Antibodies in a Case of Severe Spondylarthropathy," *Br. J. Rheumatol.* 35:1330, Oxford University Press (1996).

International Search Report and Written Opinion of the International Searching Authority for International Application No. PCT/US2007,017337, European Patent Office, mailed on Jul. 15, 2008.

* cited by examiner

FIG. 1

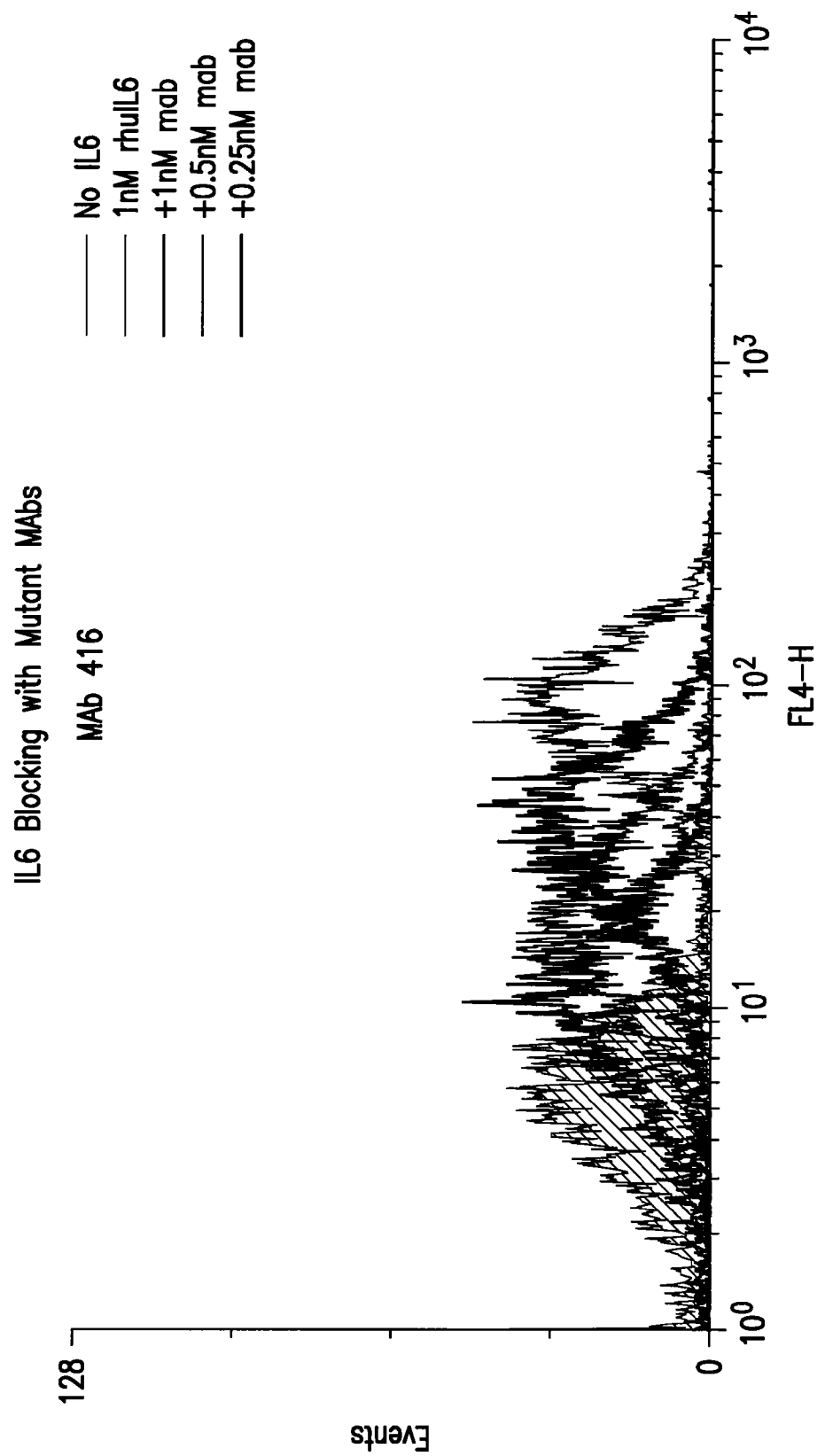

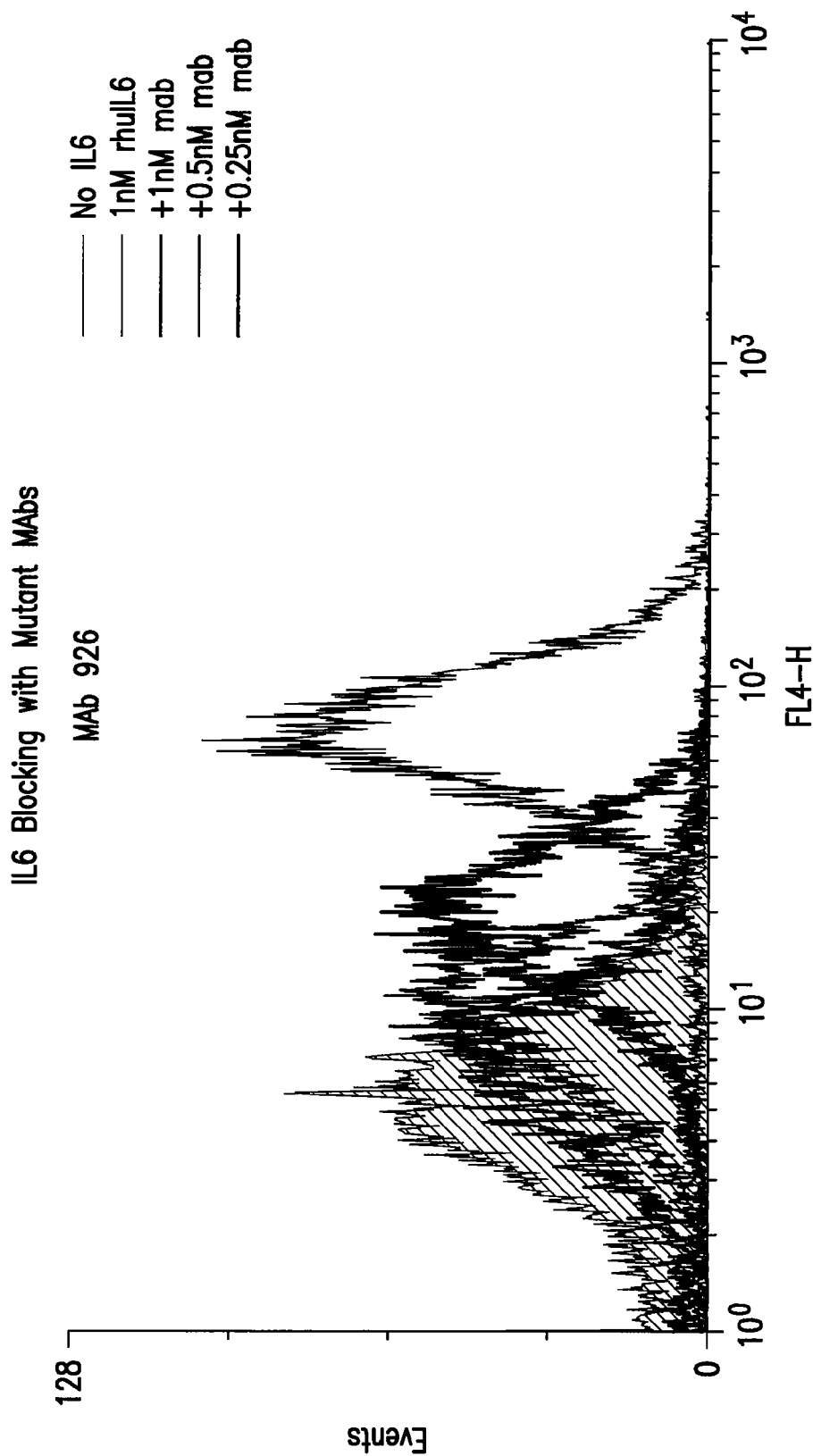

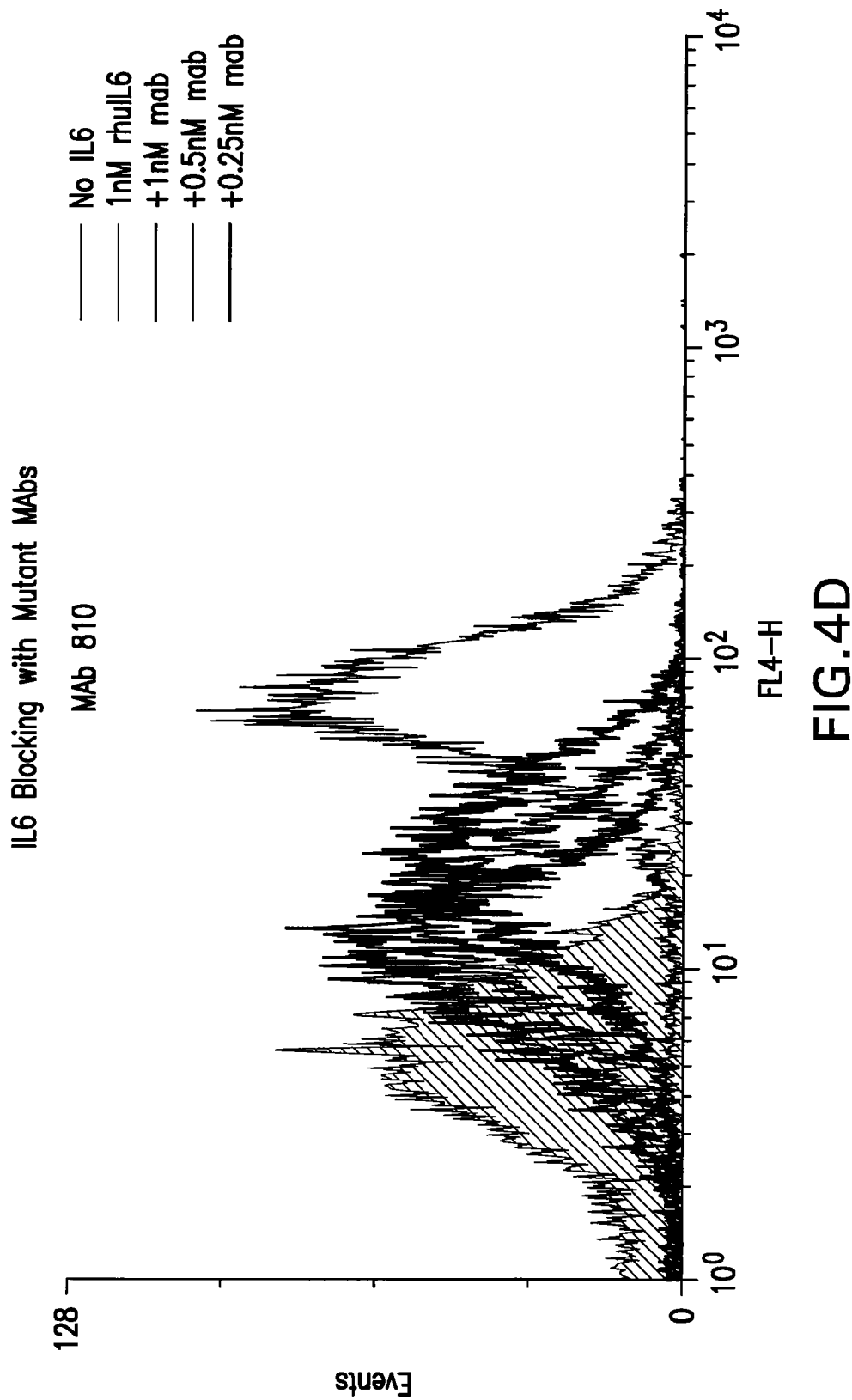

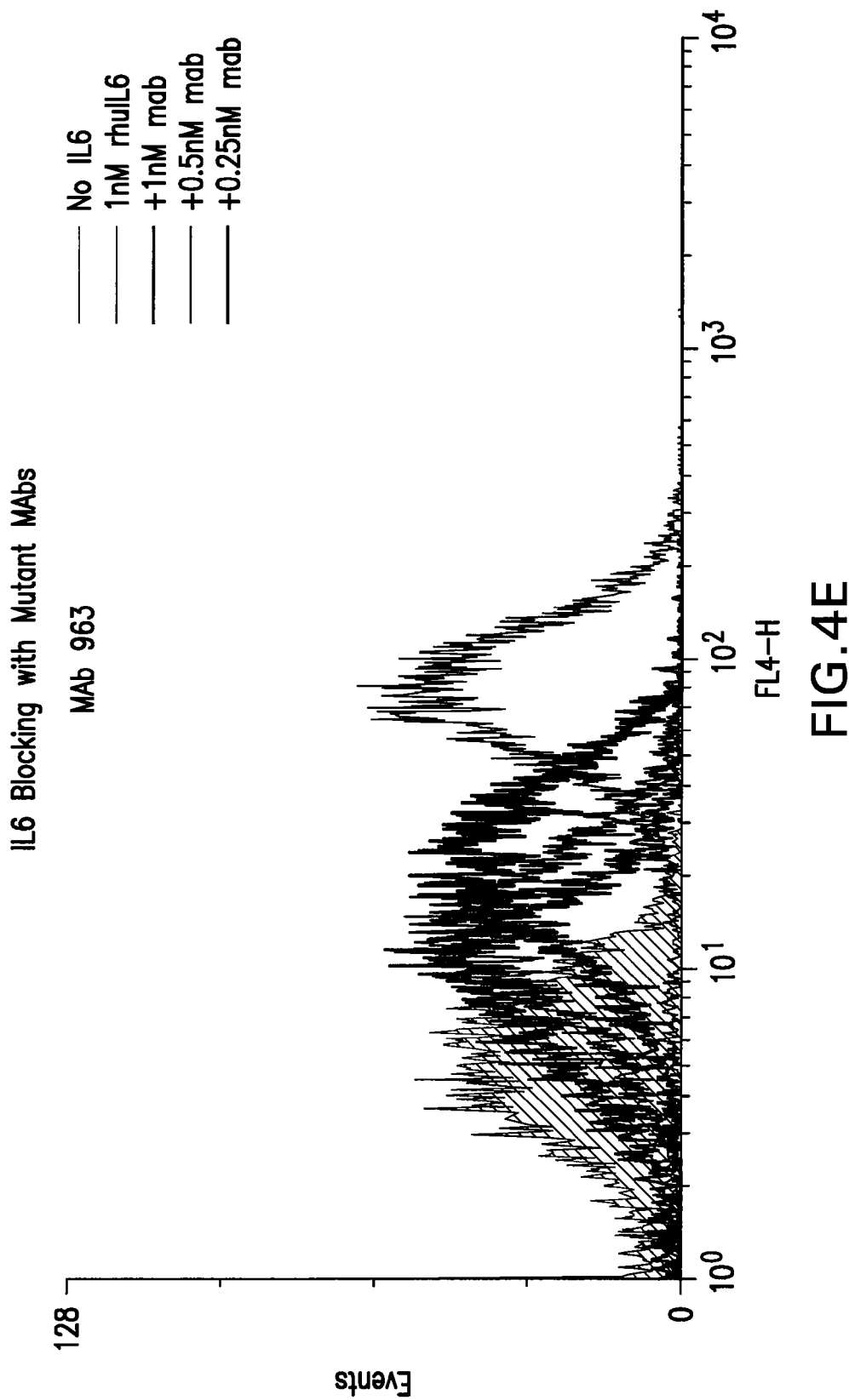

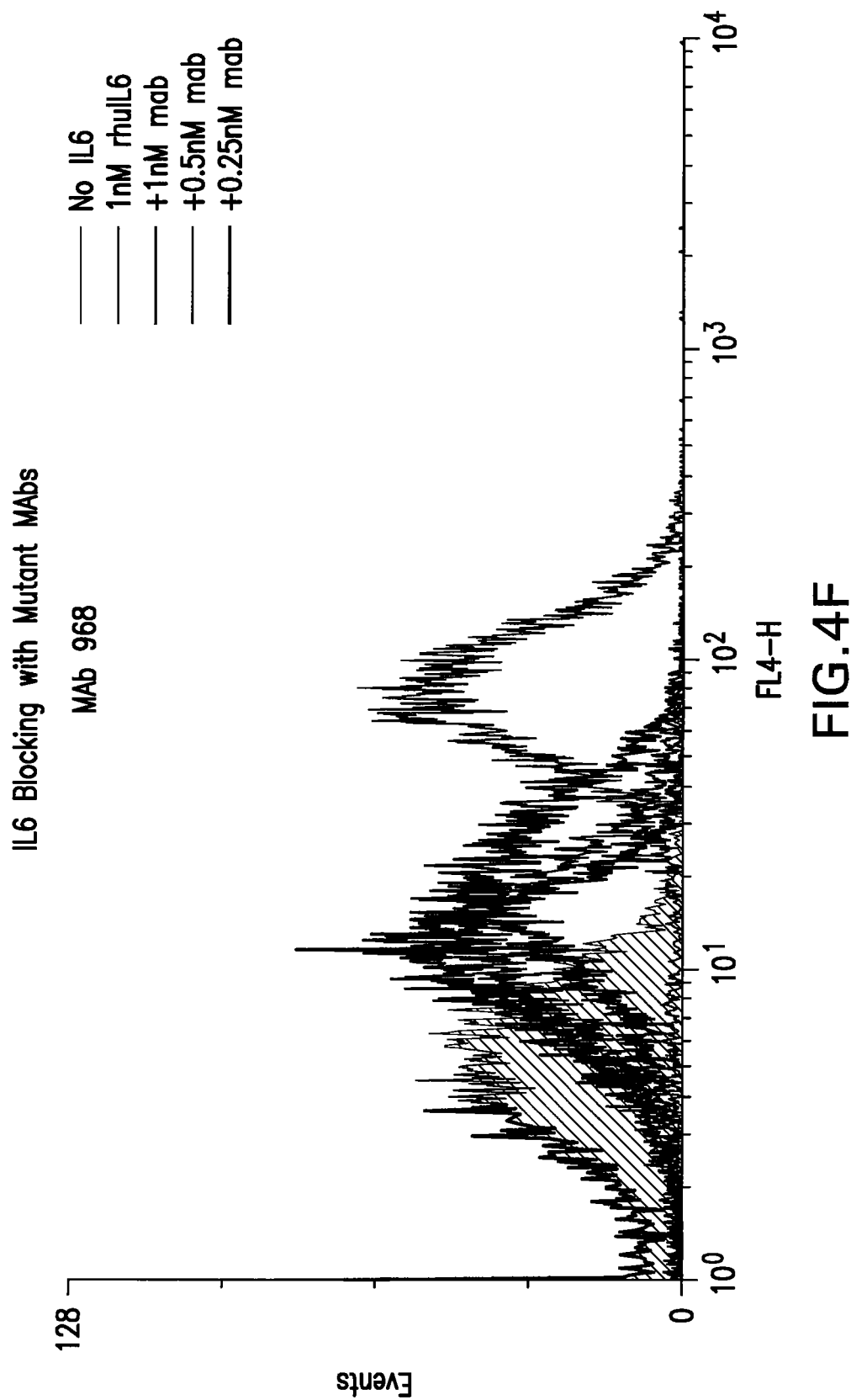

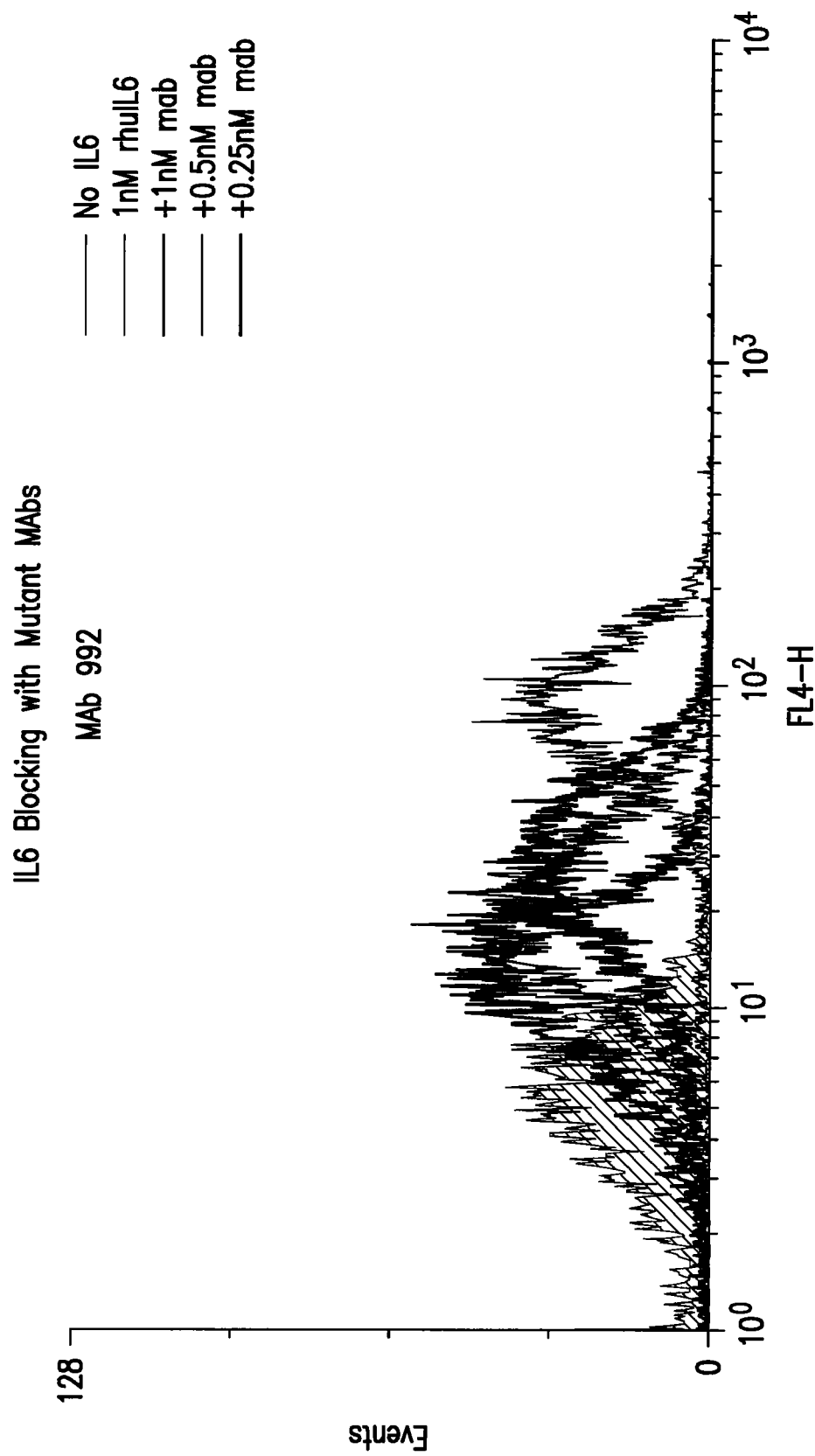

ANTI-IL-6 MONOCLONAL ANTIBODIES

CROSS-REFERENCE TO RELATED APPLICATION

This application claims the benefit of the filing date of U.S. Appl. No. 60/835,107, filed Aug. 3, 2006, which is hereby incorporated by reference in its entirety.

BACKGROUND OF THE INVENTION

1. Field of the Invention

The present invention relates to the field of monoclonal antibodies and their use in the treatment of diseases and disorders. More specifically, the invention relates to monoclonal antibodies that specifically bind to the cytokine IL-6, and to uses of the antibodies for the treatment of diseases and disorders associated with IL-6 activity or expression.

2. Related Art

Interleukin-6 (IL-6) is a 22 to 27 kDa secreted glycoprotein which exhibits growth stimulatory and proinflammatory activities. IL-6 is also known as interferon-β2 (IFN-β2), IL-1 inducible 26-kDa protein, hepatocyte-stimulating factor, cytotoxic T-cell differentiation factor, and B-cell stimulatory factor. (Trikha et al., *Clin. Cancer Res.* 9:4653-4665 (2003)). IL-6 is secreted by various cell types. IL-6 exerts its activities through binding to a high-affinity receptor complex consisting of two membrane glycoproteins: an 80 kDa component receptor that binds IL-6 with low affinity (IL-6R) and a signal-transducing component of 130 kDa (gp130) that does not bind IL-6 by itself, but is required for high-affinity binding of IL-6 by the complex. (See FIG. 11; BioCarta). IL-6R can be cleaved by a transmembrane metalloproteinase to yield the soluble IL-6R.

IL-6 blood levels are elevated in numerous infectious, inflammatory, and autoimmune diseases and in cancer in association with increased synthesis of other cytokines stimulated by infection, trauma, and immunological challenge. (Trikha et al., *Clin. Cancer Res.* 9:4653-4665 (2003)).

IL-6 has been implicated in various diseases and disorders such as multiple myeloma (Rossi et al., *Bone Marrow Transplantation* 36:771-779 (2005)), lymphomas (Emilie et al., *Blood* 84:2472-2479 (1994)), neurological disorders such as neurodegeneration, astrocytosis and cerebral angiogenesis (Campbell et al., *Proc. Natl. Acad. Sci.* 90:10061-10065 (1993)), autoimmune disorders (such as, e.g., rheumatoid arthritis), inflammatory diseases, Alzheimer's disease, myocardial infarction, Paget's disease, osteoporosis, solid tumors, prostatic and bladder cancers (Trikha et al., *Clin. Cancer Res.* 9:4653-4665 (2003)), septic shock, transplant, acute infections of the central nervous system, cardiac myxoma (Wijdenes et al., *Mol. Immunol.* 28:1183-1192 (1991)), tumor-induced cachexia (Cahlin et al., *Cancer Res.* 60:5488-5489 (2000)), cancer-associated depression, and cerebral edema secondary to brain tumors (Musselman et al., *Am. J. Psychiatry* 158:1252-1257 (2001)).

In addition, anti-IL-6 antibodies have been shown to be effective in treating several diseases and disorders. For example, anti-IL-6 monoclonal antibodies have been shown to block the proliferation of myeloma cells both in vivo and in vitro. (Rossi et al., *Bone Marrow Transplantation* 36:771-779 (2005)). Administration of anti-IL-6 antibodies to chronic rheumatoid arthritis patients was found to alleviate the symptoms of the disease (Wendling et al., *J. Rheumatol.* 20:259-262 (1993)). Anti-IL-6 antibodies have also been shown to be effective in treating AIDS-associated lymphoma (Emilie et al., *Blood* 84:2472-2479 (1994)), and metastatic renal cell carcinoma (Blay et al., *Int. J. Cancer* 72:424-430 (1997). Clinical results involving the administration of anti-IL-6 antibodies to treat various other diseases and disorders are summarized in Trikha et al., *Clin. Cancer Res.* 9:4653-4665 (2003).

Anti-IL-6 antibodies are known in the art. For example, reshaped human (i.e., humanized) anti-IL6 monoclonal antibodies derived from a mouse monoclonal antibody (SK2) are set forth in U.S. Pat. Nos. 5,618,700 and 5,856,135. Other anti-IL-6 antibodies include an antibody known as CLB-6/8 (Brakenhoff et al., *J. Immunol.* 145:561-568 (1990)) and a chimeric form thereof, known as cCLB8 (Van Zaanen et al., *J. Clin. Invest.* 98:1441-1448 (1996). A murine anti-IL-6 monoclonal antibody (mAb) designated B-E8 has been clinically used to treat various IL-6-associated diseases and disorders. (See, e.g., Bataille et al., *Blood* 86:685-691 (1995), Rossi et al., *Bone Marrow Transplantation* 36:771-779 (2005), Haddad et al., *Blood* 15:1590-1597 (2001), and Emilie et al., *Blood* 84:2472-2479 (1994)).

The use of murine antibodies, including murine anti-IL-6 antibodies, is compromised by problems such as variable selectivity for the target antigen, short serum half-lives, and the development of human anti-murine antibodies (HAMA). These issues are reduced to some extent by the development of chimeric antibodies (in which rodent constant regions are replaced by their human counterparts) or humanized/CDR-grafted/reshaped antibodies (in which only the CDRs are of non-human origin). (See generally, Vaughan et al., *Nat. Biotech.* 16:535-539 (1998)). Nonetheless, a number of practical limitations are associated with humanized antibodies, such as (1) the limited number of options for routes for efficient construction of humanized mAbs, (2) the need for detailed knowledge of antibody structure or modeling, (3) unpredictable immunogenicity due to a compromise between affinity retention and introduced foreign amino acids, and (4) limitations in the antibody repertoire to the animal in which the progenitor mAb originated. (Vaughan et al., *Nat. Biotechnol.* 16:535-539 (1998)). These limitations may be addressed by the use of human monoclonal antibodies. (Lonberg, *Nat. Biotechnol.* 23:1117-1125 (2005)).

There is therefore a need in the art for additional anti-IL-6 monoclonal antibodies for clinical applications, including human anti-IL-6 mAbs. The present invention addresses this existing need in the art.

SUMMARY OF THE INVENTION

The present invention provides novel monoclonal antibodies that bind specifically to IL-6. The antibodies of the invention comprise a variable heavy chain (VH) region selected from any of the VH regions disclosed herein as well as amino acid variants thereof, and/or a variable light chain (VL) region selected from any of the VL regions disclosed herein as well as amino acid variants thereof.

In one exemplary embodiment of the invention, multiple VH and VL regions were obtained from a library of human VH and VL genes. Antibody heavy chains containing human VH regions obtained from the library were paired with light chains from a known murine anti-IL-6 mAb (i.e., B-E8). Likewise, antibody light chains containing human VL regions obtained from the library were paired with heavy chains from a known murine anti-IL-6 mAb (i.e., B-E8). The resulting antibodies were screened for their ability to bind specifically to an IL-6 antigen. From this process, eighteen human VLs (represented by SEQ ID NOs:1 to 18) and seven human VHs (represented by SEQ ID NOs:19 to 25) were identified.

All of the identified VLs were cross paired with all of the identified VHs. The resulting antibodies were tested for binding affinity to IL-6 by ELISA and for the ability to block IL-6-induced cell proliferation. From this process, 33 human VH/VL pairings were identified that exhibited substantial binding affinity and blocking activity.

Amino acid substitutions were introduced into certain human VHs and VLs identified by the above-described process. The variant VHs and VLs were paired with human VLs and VHs, respectively, and the resulting antibodies were again tested for IL-6 binding affinity and blocking activity. From these experiments, several antibodies were identified with binding and blocking activities comparable to that of the original murine B-E8 antibody (or a chimera thereof). The present invention therefore also includes antibodies comprising any combination of the variant VHs and VLs obtained by the process outlined above and described in detail in the Examples below.

The invention also includes nucleic acid molecules that encode any of the VH and/or VL regions disclosed herein, and vectors and host cells comprising the nucleic acid molecules.

In some embodiments, the novel monoclonal antibodies of the present invention demonstrate species specificity, binding to or aiding in the detection of human IL-6. In some embodiments, the novel monoclonal antibodies of the present invention bind to or aid in the detection of human and monkey IL-6 but not murine or rat IL-6.

In some embodiments, the novel monoclonal antibodies of the present invention inhibit IL-6-induced proliferation of cells such as murine B9 (ECACC) myeloma cells or human U266 myleoma cells.

In some embodiments, the novel monoclonal antibodies of the present invention bind to IL-6 but not to other IL-6 superfamily members.

In some embodiments, the novel monoclonal antibodies of the present invention bind specifically to IL-6, inhibiting the binding of IL-6 to its receptor.

The invention also includes methods of producing an antibody of the present invention, the method comprising: (i) culturing a host cell expressing one or more nucleic acid sequences encoding an antibody of the present invention, and (ii) recovering the antibody from the culture medium.

The invention also includes pharmaceutical compositions comprising an antibody of the present invention. It is contemplated that the pharmaceutical composition may further comprise a pharmaceutically acceptable carrier, an adjuvant, or a combination thereof.

The invention also includes methods of preventing or treating diseases and/or disorders associated with IL-6 activity or expression, wherein the methods comprise administering an antibody of the present invention to a patient in need thereof. In one embodiment, the methods comprise administering a therapeutically or prophylactically effective amount of a pharmaceutical composition comprising an antibody of the present invention and a pharmaceutically acceptable carrier to a patient in need thereof. In some embodiments, the disease or disorder includes any disease or disorder mediated by, associated with, or caused by the action of IL-6. In some embodiments, the disease or disorder to be treated is selected from the group consisting of an autoimmune disease or disorder, a disease or disorder associated with aberrant or inappropriate angiogenesis, cancer, osteoarthritis, idiopathic juvenile arthritis, and fibrotic conditions.

The invention also includes use of an antibody of the present invention for the manufacture of a medicament for the treatment of a disease or disorder mediated by, associated with, or caused by the action of IL-6. In a particular embodiment, the invention is also directed to use of an antibody of the present invention for the manufacture of a medicament for the treatment of a disease or disorder selected from the group consisting of an autoimmune disease or disorder, a disease or disorder associated with aberrant or inappropriate angiogenesis, cancer, osteoarthritis, idiopathic juvenile arthritis, and fibrotic conditions.

The invention also includes an antibody of the present invention for use in the treatment of a disease or disorder mediated by, associated with, or caused by the action of IL-6. In a particular embodiment, the invention is also directed to use of an antibody of the present invention for the manufacture of a medicament for the treatment of a disease or disorder selected from the group consisting of an autoimmune disease or disorder, a disease or disorder associated with aberrant or inappropriate angiogenesis, cancer, osteoarthritis, idiopathic juvenile arthritis, and fibrotic conditions.

BRIEF DESCRIPTION OF THE FIGURES

FIG. 1 shows an alignment of exemplary human VH regions, represented by SEQ ID NOs:19-25, that can be included within the antibodies of the invention.

FIGS. 4A-4G show the results of an IL-6 binding inhibition assay in which human recombinant IL-6 was incubated with various anti-IL-6 antibodies, followed by the addition of IL-6 receptor-bearing U266 cells. A purified mouse IL-6 antibody and an APC-conjugated polyclonal goat-anti-mouse secondary antibody were then added. Flow cytometry analysis was used to quantitate the IL-6 blocking activity at various anti-IL-6 antibody concentrations.

In FIG. 6A, the concentration of mAb was 0.5 µg/ml. For each mAb, the four columns from left to right indicate the percent inhibition of IL-6 binding to IL-6 receptor at IL-6 concentrations of 100.0, 50.0, 25.0, and 12.5 ng/ml, respectively.

In FIG. 7A, the concentration of IL-6 was 500 ng/ml. For each mAb in FIG. 7A, the eight columns from left to right indicate the percent inhibition of IL-6 binding to IL-6 receptor at mAb concentrations of 5000, 2500, 1250, 625.0, 156.3, 78.1, and 39.1 ng/ml, respectively.

In FIG. 6B, the concentration of mAb, if present, was 0.5 µg/ml mAb. In FIG. 7B, the concentration of mAb, if present, was 0.3 µg/ml mAb.

In FIG. 17, the four columns from left to right indicate the optical density associated with detection of human IL-6 in human serum at serum dilutions of 1, ½, ¼, and ⅛. Each column represents a mean of two experiments +/− standard deviation.

In FIG. 18, the four columns from left to right indicate the optical density associated with detection of monkey IL-6 in rhesus monkey serum at serum dilutions of 1/10, 1/20, 1/40, 1/80, 1/160, 1/320, and 1/640.

DETAILED DESCRIPTION OF THE INVENTION

Figure 2:
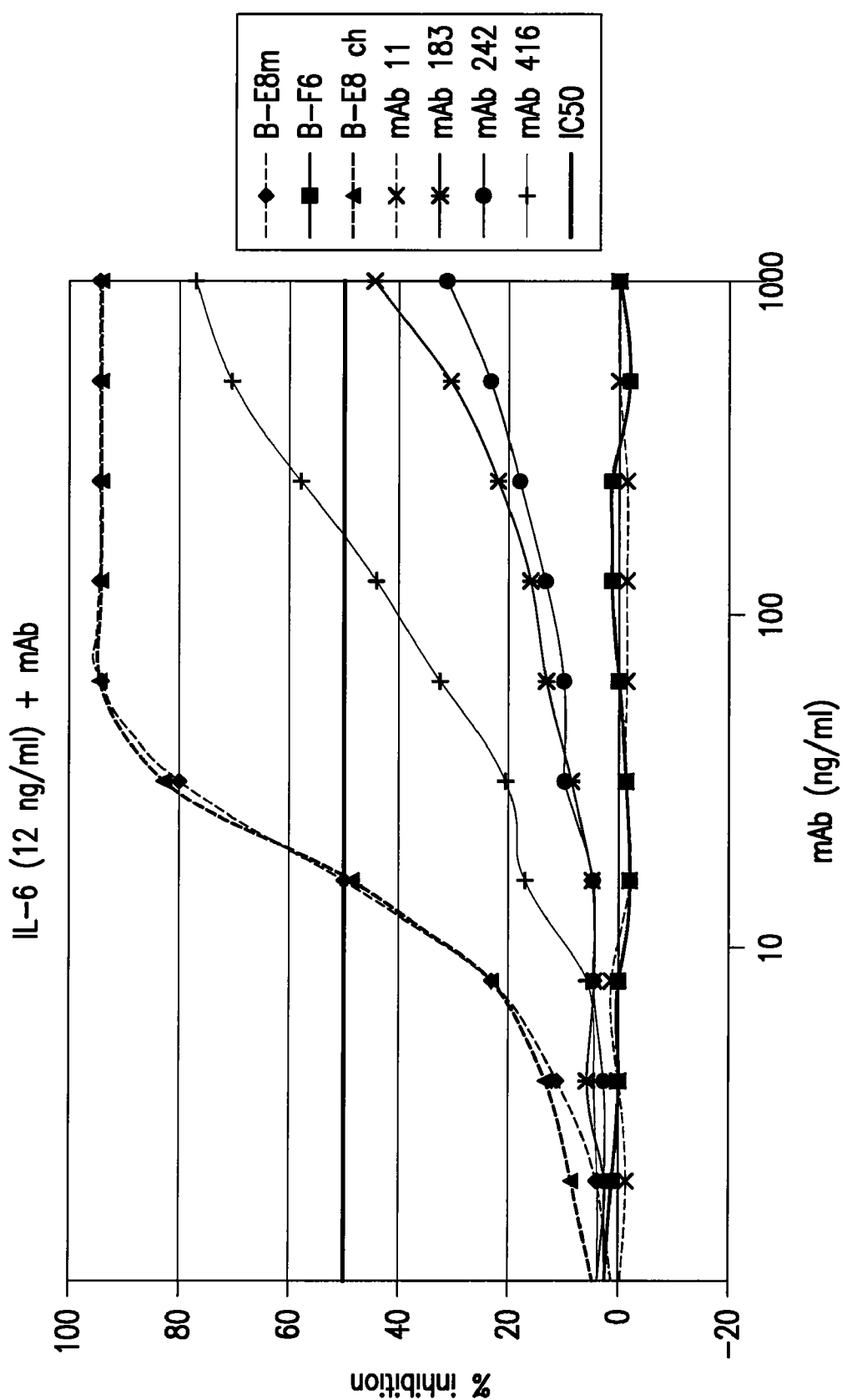
FIG. 2 shows the results of an IL-6 binding inhibition assay in which biotinylated human recombinant IL-6 was incubated with various anti-IL-6 antibodies, followed by the addition of IL-6 receptor-bearing U266 cells. Flow cytometry analysis was used to quantitate the percent inhibition of IL-6 binding at various anti-IL-6 antibody concentrations.

Unless otherwise defined, all technical and scientific terms used herein have the meanings commonly understood by one of ordinary skill in the art for the art to which this invention belongs.

Antibodies

The present invention provides monoclonal antibodies that specifically bind to IL-6.

As used herein, the term "antibody" includes immunoglobulin molecules comprising four polypeptide chains, two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chains of antibodies (immunoglobulins) from any vertebrate species can be assigned to one of two clearly distinct types, called kappa (K) and lambda (λ), based on the amino acid sequences of their constant domains. The variable regions of kappa light chains are referred to herein as VK. The expression VL, as used herein, is intended to include both the variable regions from kappa-type light chains (VK) and from lambda-type light chains. The light chain constant region is comprised of one domain, CL. The VH and VL regions include regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1-CDR1-FR2-CDR2-FR3-CDR3-FR4.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called α, δ, ε, γ, and µ, respectively. The subunit structures and three-dimensional configurations of different classes of immunoglobulins are well known. The present invention includes antibodies of any of the aforementioned classes or subclasses (isotypes).

The term "antibody" as used herein is also intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof; each containing at least one CDR. Functional fragments include antigen binding fragments that bind to an IL-6 antigen. For example, antibody fragments capable of binding to IL-6 or a portion thereof, including, but not limited to Fab (e.g., by papain digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the present invention. Antibody fragments are also intended to include, e.g., domain deleted antibodies, diabodies, linear antibodies, single-chain antibody molecules, and multispecific antibodies formed from antibody fragments.

The term "monoclonal antibody," as used herein, refers to an antibody obtained from a population of substantially homogeneous antibodies, e.g., the individual antibodies comprising the population are substantially identical except for possible naturally occurring mutations or minor post-translational variations that may be present. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. The monoclonal antibodies of the present invention are preferably made by recombinant DNA methods or are obtained by screening methods as described elsewhere herein.

The term "monoclonal antibodies," as used herein, includes "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species (e.g., mouse or rat) or belonging to another antibody class or subclass, as well as fragments of such antibodies, so long as they exhibit the desired biological activity (Morrison et al., *Proc. Natl. Acad. Sci. USA* 81:6851-6855 (1984)). Chimeric antibodies of interest herein include "primatized" antibodies comprising variable domain antigen-binding sequences derived from a non-human primate (e.g., Old World Monkey, such as baboon, rhesus or cynomolgus monkey) and human constant region sequences (U.S. Pat. No. 5,693,780).

Thus, the present invention includes, for example, chimeric monoclonal antibodies comprising a chimeric heavy chain and/or a chimeric light chain. The chimeric heavy chain may comprise any of the heavy chain variable (VH) regions described herein or mutants or variants thereof fused to a heavy chain constant region of a non-human antibody. The chimeric light chain may comprise any of the light chain variable (VL) regions described herein or mutants or variants thereof fused to a light chain constant region of a non-human antibody.

The term "human antibody," as used herein, includes antibodies having variable and constant regions corresponding to human germline immunoglobulin sequences as described by Kabat et al. (See Kabat, et al. (1991) Sequences of Proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The human antibody can have at least one position replaced with an amino acid residue, e.g., an activity enhancing amino acid residue which is not encoded by the human germline immunoglobulin sequence. In the context of the present invention, the human antibody can have up to twenty positions replaced with amino acid residues which are not part of the human germline immunoglobulin sequence. In other embodiments, up to ten, up to five, up to three or up to two positions are replaced. However, the term "human antibody," as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences (See Kabat, E. A., et al. (1991) Sequences of Proteins of Immunological Interest, Fifth Edition, U.S. Department of Health and Human Services, NIH Publication No. 91-3242). According to the present invention, recombinant human antibodies include human germline immunoglobulin sequence that have been subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or backmutation or both.

The antibodies of the present invention may be isolated antibodies. An "isolated antibody," as used herein, includes an antibody that is substantially free of other antibodies having different antigenic specificities. Moreover, an isolated antibody may be substantially free of other cellular material and/or chemicals.

The antibodies of the present invention preferably bind specifically to an IL-6 antigen. As used herein, "an IL-6 antigen" is intended to include, e.g., the complete IL-6 protein or a fragment of the IL-6 protein. The term "IL-6 antigen" is intended to encompass naturally occurring IL-6 (e.g., IL-6 purified from a cell that expresses IL-6 under normal conditions) as well as recombinant IL-6 and variants and mutants thereof. Preferably, the IL-6 antigen is capable of binding to the IL-6 receptor.

An antibody of the present invention binds specifically to an IL-6 antigen if, e.g., the antibody binds to an IL-6 antigen and will not show any significant binding to non-IL-6 molecules. In certain embodiments, an antibody binds specifically to an IL-6 antigen if it binds to an IL-6 antigen with an affinity that is at least 1000 fold, at least 500 fold, at least 200 fold, at least 100 fold, at least 90 fold, at least 80 fold, at least 70 fold, at least 60 fold, at least 50 fold, at least 40 fold, at least 30 fold, at least 20 fold, at least 10 fold or at least 2 fold greater than the affinity with which it binds to an antigen other than an IL-6 antigen.

Whether an antibody of the invention binds specifically to an IL-6 antigen can be determined, e.g., by a binding assay such as an ELISA, employing a panel of antigens including an IL-6 antigen as well as at least one other non-IL-6 antigen. An exemplary method for assessing specificity is set forth in Example 5, below. Here, a human anti-IL-6 antibody of the invention (mAb 1339) was tested by ELISA for binding to unrelated antigens such as human insulin, human serum albumin, human hemoglobin, and bovine serum albumin. Since no binding to the non-IL-6 antigens was observed, mAb 1339 was deemed to bind specifically to IL-6.

In certain embodiments, an antibody of the present invention binds specifically to IL-6 but not to other IL-6 superfamily members. In certain embodiments, an antibody of the invention binds specifically to an IL-6 antigen if it binds to an IL-6 antigen with an affinity that is at least 1000 fold, at least 500 fold, at least 200 fold, at least 100 fold, at least 90 fold, at least 80 fold, at least 70 fold, at least 60 fold, at least 50 fold, at least 40 fold, at least 30 fold, at least 20 fold, at least 10 fold or at least 2 fold greater than the affinity with which it binds to an IL-6 superfamily member such as, e.g., CNFT, oncostatin M, IL-11 or NNT-1. For example, mAb 1339 was shown by ELISA to bind to IL-6 and showed insignificant levels of binding to CNFT, oncostatin M, IL-11 or NNT-1. (See Example 5 and FIG. 5B). This or a similar assay can be used to assess whether any antibody specifically binds to an IL-6 antigen.

In other embodiments, an antibody of the invention binds specifically to an IL-6 antigen when the dissociation constant ($K_d$) is about $10^{-8}$ M. The antibody, in certain embodiments, is said to bind specifically to an IL-6 antigen with "high affinity" when the $K_d$ is about $5 \times 10^{-9}$ M, and with "very high affinity" when the $K_d$ is about $5 \times 10^{-10}$ M.

Whether an antibody binds specifically to an IL-6 antigen in the context of the present invention can also be determined by functional assay. For example, an assay can be conducted in which cells expressing IL-6 receptor are incubated with IL-6 in the presence of a test antibody. In a parallel assay, cells expressing another receptor are incubated with the ligand for the receptor in the presence of the test antibody. If the antibody shows an inhibitory effect in the first assay (which includes IL-6 and cells expressing the IL-6 receptor) but does not show an inhibitory effect in the second assay (which includes a different ligand and cells expressing the receptor for that ligand), then it can be concluded that the antibody binds specifically to an IL-6 antigen. Assays for determining whether an antibody inhibits the biological effects of IL-6 binding to an IL-6 receptor on cells are discussed elsewhere herein. For instance, Example 5 shows the ability of human anti-IL-6 antibodies of the invention to inhibit IL-6-induced human myeloma cell proliferation.

In some embodiments, the antibodies of the present invention inhibit IL-6-induced proliferation of cells such as murine B9 (ECACC) or human U266 myeloma cells. In some embodiments, the antibodies of the present invention inhibit IL-6-induced proliferation of cells such as murine B9 (ECACC) human U266 myeloma cells at a level of 100% (i.e., complete) inhibition. In some embodiments, the antibodies of the present invention inhibit IL-6-induced proliferation of cells such as murine B9 (ECACC) or human U266 myeloma cells at a level of 90% or greater inhibition. In some embodiments, the antibodies of the present invention inhibit IL-6-induced proliferation of cells such as murine B9 (ECACC) or human U266 myeloma cells at a level of 80% or greater inhibition. In some embodiments, the antibodies of the present invention inhibit IL-6-induced proliferation of cells such as murine B9 (ECACC) or human U266 myeloma cells at a level of 70% or greater, 60% or greater, 50% or greater, 40% or greater, 30% or greater, 20% or greater, 10% or greater, or 5% or greater, or 1% or greater inhibition.

In some embodiments, the antibodies of the present invention bind specifically to IL-6, inhibiting the binding of IL-6 to its receptor. In some embodiments, the antibodies of the present invention bind specifically to IL-6, inhibiting the binding of IL-6 to its receptor at a level of 100% (i.e., complete) inhibition. In some embodiments, the antibodies of the present invention bind specifically to IL-6, inhibiting the binding of IL-6 to its receptor at a level of 90% or greater inhibition. In some embodiments, the antibodies of the present invention bind specifically to IL-6, inhibiting the binding of IL-6 to its receptor at a level of 80% or greater inhibition. In some embodiments, the antibodies of the present invention bind specifically to IL-6, inhibiting the binding of IL-6 to its receptor at a level of 70% or greater, 60% or greater, 50% or greater, 40% or greater, 30% or greater, 20% or greater, 10% or greater, 5% or greater, or 1% or greater inhibition.

In some embodiments, the antibodies of the present invention demonstrate species specificity, binding to or aiding in the detection of human IL-6. In some embodiments, the novel monoclonal antibodies of the present invention bind to or aid in the detection of human or monkey IL-6 but not murine or rat IL-6.

The human antibodies of the invention can be obtained by a variety of methods. For example, human monoclonal antibodies that bind to IL-6 can be selected, for example, by screening one or more human VL and VH cDNA libraries with IL-6 or a portion thereof, such as by phage display techniques. (McCafferty et al., *Nature* 348:552-554 (1990)). Human antibodies of the invention can also be obtained from transgenic animals such as, e.g., transgenic mice. (Jakobovits, *Curr. Opin. Biotechnol.* 6:561-566 (1995)). The present invention includes human anti-IL-6 antibodies that are obtained by any method known in the art for making human antibodies.

Exemplary methods that can be used to generate antibodies of the invention are disclosed, e.g., in U.S. Patent Appl. Publication No. 2005/0196755, the content of which is incorporated by reference in its entirety.

The present invention thus includes monoclonal antibodies that comprise a human heavy chain variable region (VH), wherein the human VH, when paired with a variable light chain region (VL) of a non-human anti-IL-6 monoclonal antibody (such as, e.g., B-E8), results in an antibody the binds specifically to an IL-6 antigen.

The present invention also includes monoclonal antibodies that comprise a human light chain variable region (VL), wherein the human VL, when paired with a variable heavy chain region (VH) of a non-human anti-IL-6 monoclonal antibody (such as, e.g., B-E8), results in an antibody that binds specifically to an IL-6 antigen. In certain embodiments, the human VL is of the kappa subtype (i.e., VK).

The present invention also includes monoclonal antibodies that comprise a human heavy chain variable region (VH) and a human light chain variable region (VL), wherein the human VH, when paired with a variable light chain region (VL) of a non-human anti-IL-6 monoclonal antibody (such as, e.g., B-E8), results in an antibody the binds specifically to an IL-6 antigen, and wherein the human VL, when paired with a variable heavy chain region (VH) of a non-human anti-IL-6 monoclonal antibody (such as, e.g., B-E8), results in an antibody that binds specifically to an IL-6 antigen.

In certain embodiments, the monoclonal antibodies of the invention comprise a variable heavy chain region (VH) comprising an amino acid sequence selected from the group consisting of H415 (SEQ ID NO:19), H884 (SEQ ID NO:20), H1077 (SEQ ID NO:21), H1078 (SEQ ID NO:22), H1079 (SEQ ID NO:23), H1081 (SEQ ID NO:24), H1089 (SEQ ID NO:25), H1511 (SEQ ID NO:26), H1420 (SEQ ID NO:27), H1432 (SEQ ID NO:28), H1515 (SEQ ID NO:29), H1362 (SEQ ID NO:30), H1437 (SEQ ID NO:31), H1461 (SEQ ID NO:32), H1519 (SEQ ID NO:38), H1520 (SEQ ID NO:39), H1521 (SEQ ID NO:40), H1522 (SEQ ID NO:41), H1553

(SEQ ID NO:42), and H1579 (SEQ ID NO:43), wherein the antibodies bind specifically to an IL-6 antigen.

In certain embodiments, the monoclonal antibodies of the invention comprise a variable light chain region (VL or VK) comprising an amino acid sequence selected from the group consisting of L112 (SEQ ID NO:1), L151 (SEQ ID NO:2), L158 (SEQ ID NO:3), L159 (SEQ ID NO:4), L164 (SEQ ID NO:5), L165 (SEQ ID NO:6), L166 (SEQ ID NO:7), L167 (SEQ ID NO:8), L168 (SEQ ID NO:9), L169 (SEQ ID NO:10), L170 (SEQ ID NO:11), L171 (SEQ ID NO:12), L172 (SEQ ID NO:13), L173 (SEQ ID NO:14), L174 (SEQ ID NO:15), L175 (SEQ ID NO:16), L189 (SEQ ID NO:17), L198 (SEQ ID NO:18), L314 (SEQ ID NO:33), L305 (SEQ ID NO:34), L303 (SEQ ID NO:35), L298 (SEQ ID NO:36), and L321 (SEQ ID NO:37), wherein the antibodies bind specifically to an IL-6 antigen.

It will be understood by a person of ordinary skill in the art that "antibodies comprising a variable heavy chain region (VH)" and "antibodies comprising a variable light chain region (VL or VK)," as described in the context of the present invention, may include one or more additional regions (or "domains") that are normally found in antibody molecules, such as, e.g., one or more constant heavy chain regions (e.g., CH1, CH2 and/or CH3), and/or a constant light chain region (CL).

The antibodies of the invention may, in certain embodiments, comprise a variable heavy chain region (VH) comprising an amino acid sequence that is at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to any one of SEQ ID NOs:19 to 32 or 38 to 43, wherein the antibodies bind specifically to an IL-6 antigen.

The antibodies of the invention may, in certain embodiments, comprise a variable light chain region (VL or VK) comprising an amino acid sequence that is at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to any one of SEQ ID NOs:1 to 18 or 33 to 37, wherein the antibodies bind specifically to an IL-6 antigen.

The term "identical," as used herein, refers to a relationship between the sequences of two or more polypeptide molecules as determined by aligning and comparing the sequences. "Percent identity" means the percent of identical residues between the amino acids in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48: 1073.

In calculating percent identity, the sequences being compared are aligned in a way that gives the largest match between the sequences. The computer program used to determine percent identity may be the GCG program package, which includes GAP (Devereux et al., 1984, Nucl Acid Res 12:387; Genetics Computer Group, University of Wisconsin, Madison, Wis.). The computer algorithm GAP is used to align the two polypeptides for which the percent sequence identity is to be determined. The sequences are aligned for optimal matching of their respective amino acid (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see Dayhoff et al., 1978, Atlas of Protein Sequence and Structure 5:345-352 for the PAM 250 comparison matrix; Henikoff et al., 1992, Proc. Natl. Acad. Sci. USA 89: 10915-10919 for the BLOSUM 62 comparison matrix) is also used by the algorithm.

Recommended parameters for determining percent identity for polypeptides using the GAP program are the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps);

Gap Length Penalty: 4;

Threshold of Similarity: 0.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

Amino acid sequence modification(s) of anti-IL-6 antibodies described herein are contemplated. For example, it may be desirable to improve the binding affinity and/or other biological properties of the anti-IL-6 antibodies.

Amino acid sequence variants of the anti-IL-6 antibodies may be prepared by introducing appropriate nucleotide changes into a nucleic acid that encodes the heavy or light chains of the antibody, or by peptide synthesis. Exemplary modifications include those that alter the amino acid sequence of a variable region of the heavy and/or light chain of the antibody. Especially preferred are modifications that alter the amino acid sequence of one or more CDR of a variable region of a heavy and/or light chain of an antibody of the invention.

Exemplary modifications include, for example, deletions from, and/or insertions into and/or substitutions of, residues within the amino acid sequences of the anti-IL-6 antibodies. Any combination of deletion, insertion, and substitution is made to arrive at the final construct, provided that the final construct possesses the desired characteristics (e.g., the ability to form part of an antibody that binds specifically to an IL-6 antigen). The amino acid changes also may alter post-translational processes of the anti-IL-6 antibodies, such as changing the number or position of glycosylation sites.

One exemplary method for introducing amino acid changes into the VH and VL regions of the antibodies of the invention is illustrated in Example 2, below. According to this method, NNK is introduced at specific positions, e.g., within a CDR of a VH or VL, where N can be A, T, G, or C, and K is T or G. Using NNK, all 20 amino acids and 1 stop codon can be introduced at each position.

Another useful method for identification of certain residues or regions of the anti-IL-6 antibody variable heavy chain regions and variable light chain regions that are preferred locations for mutagenesis is called "alanine scanning mutagenesis" as described by Cunningham and Wells, *Science* 244:1081-1085 (1989). Here, a residue or group of target residues are identified (e.g., charged residues such as arg, asp, his, lys, and glu) and replaced by a neutral or negatively charged amino acid (most preferably alanine or polyalanine). Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed VH variants and/or VL variants are screened for the desired activity when combined with a variable light chain or variable heavy chain, respectively.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-IL-6 VH or an anti-IL-6 VL with an N-terminal methionyl residue, or an anti-IL-6 VH or an anti-IL-6 VL fused to a cytotoxic polypeptide.

Another type of variant is an amino acid substitution variant. These variants have at least one amino acid residue in the VH or VL molecule replaced by a different residue. The sites of greatest interest for substitutional mutagenesis of VH and VL regions of anti-IL-6 antibodies of the invention include the hypervariable regions, but FR alterations are also contemplated.

Conservative substitutions are shown in Table 1 under the heading of "preferred substitutions." If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp; lys; arg | gln |
| Asp (D) | glu; asn; | glu |
| Cys (C) | ser; ala | ser |
| Gln (Q) | asn; glu | asn |
| Glu (E) | asp; gln | asp |
| Gly (G) | ala | ala |
| His (H) | asn, gln, lys, arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Tpr (W) | tyr; phe | tyr |
| Tyr (Y) | trp; phe; thr; ser | phe |
| Val (V) | ile; leu; met; phe; ala; norleucine | leu |

Substantial modifications in the biological properties of the anti-IL-6 antibodies of the invention may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-IL-6 antibody also may be substituted, generally with serine, to improve the oxidative stability of the molecule and prevent aberrant crosslinking. Conversely, cysteine bond(s) may be added to the anti-IL-6 antibody to improve its stability (particularly where the anti-IL-6 antibody is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated (e.g., improved affinity for an IL-6 antigen). One exemplary method for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the anti-IL-6 antibodies set forth herein alters the original glycosylation pattern of the anti-IL-6 antibodies. Such altering includes deleting one or more carbohydrate moieties found in the anti-IL-6 antibody, and/or adding one or more glycosylation sites that are not present in the anti-IL-6 antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an anti-IL-6 antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-IL-6 antibody (for O-linked glycosylation sites).

The VH domains included in the antibodies of the invention may, in certain embodiments, comprise an amino sequence that is identical to any one of SEQ ID NOs:19 to 32 or 38 to 43, except for a substitution of 1 to 20 amino acids. For example, the VH may have an amino acid sequence that is identical to SEQ ID NOs:19 to 32 or 38 to 43, except for a substitution of 1, 2, 3, 4, 5, 6, 7, 8, 9, 10, 11, 12, 13, 14, 15, 16, 17, 18, 19 or 20 amino acids. The substitution(s) can be at any position within the sequence found in SEQ ID NOs:19 to 32 or 38 to 43. In certain embodiments, the substitution(s) is/are within one or more CDR of the VH domain. For example, the substitution(s) can be within CDR1, CDR2 and/or CDR3.

Likewise, the VL domains included in the antibodies of the invention may, in certain embodiments, comprise an amino sequence that is identical to any one of SEQ ID NOs:1 to 18 or 33 to 37, except for a substitution of 1 to 20 amino acids. For example, the VL may have an amino acid sequence that is identical to SEQ ID NOs:1 to 18 or 33 to 37, except for a substitution of 1, 2, 3, 4, 5, 6, 7, 8, 9, 10, 11, 12, 13, 14, 15, 16, 17, 18, 19 or 20 amino acids. The substitution(s) can be at any position within the sequence found in SEQ ID NOs:1 to 18 or 33 to 37. In certain embodiments, the substitution(s) is/are within one or more CDR of the VL domain. For example, the substitution(s) can be within CDR1, CDR2 and/or CDR3.

The anti-IL-6 antibodies of the present invention which comprise a VH region that differs from SEQ ID NOs:19 to 32 or 38 to 43 in one or more amino acid residues and/or a VL region that differs from SEQ ID NOs:1 to 18 or 33 to 37 in one or more amino acid residues will preferably retain the ability to specifically bind to an IL-6 antigen.

The present invention includes anti-IL-6 antibodies comprising a VH domain, wherein the VH comprises any one of the CDR1s set forth in Table 2:

TABLE 2

| Exemplary VH CDR1 sequences | |
|---|---|
| VH CDR1 Sequence | SEQ ID NO: |
| TSGMCVS | 51 |
| TSGVAVG | 52 |
| TSGVSVG | 53 |

TABLE 2-continued

| Exemplary VH CDR1 sequences | |
|---|---|
| VH CDR1 Sequence | SEQ ID NO: |
| TSGVGVG | 54 |
| TSGVAVN | 55 |

The invention includes anti-IL-6 antibodies comprising a VH domain, wherein the VH comprises a variant CDR1 having an amino acid sequence that is identical to any one of SEQ ID NOs:51 to 55, except that one or more (e.g., one, two, three, four, five, six or seven) of the amino acids from SEQ ID NOs:51 to 55 is replaced with any other amino acid. Preferably the anti-IL-6 antibodies comprising a variant CDR1 will specifically bind to an IL-6 antigen.

The invention also includes anti-IL-6 antibodies comprising a VH domain, wherein the VH comprises any one of the CDR2s set forth in Table 3:

TABLE 3

| Exemplary VH CDR2 sequences | |
|---|---|
| VH CDR2 Sequence | SEQ ID NO: |
| LIYWDDDKRYNPSLRS | 56 |
| LIFWDDDKHYSPSLKS | 57 |
| LVYWDDDRRYNPSLKN | 58 |
| LIYWDDDKRYSPSLKN | 59 |
| FIFWDDDKYYSPSLES | 60 |
| VIYWDDDRRYSPSLSS | 61 |
| LIYWDDDKRYSPSLET | 97 |
| FIWWDDDKYYSPSLES | 101 |

The invention includes anti-IL-6 antibodies comprising a VH domain, wherein the VH comprises a variant CDR2 having an amino acid sequence that is identical to any one of SEQ ID NOs:56 to 61 or 97, except that one or more (e.g., one, two, three, four, five, six, seven, eight, nine, ten, eleven, twelve, thirteen, fourteen, fifteen or sixteen) of the amino acids from SEQ ID NOs:56 to 61 or 97 is replaced with any other amino acid. Preferably the anti-IL-6 antibodies comprising a variant CDR2 will specifically bind to an IL-6 antigen.

The invention also includes anti-IL-6 antibodies comprising a VH domain, wherein the VH comprises any one of the CDR3s set forth in Table 4:

TABLE 4

| Exemplary VH CDR3 sequences | |
|---|---|
| VH CDR3 Sequence | SEQ ID NO: |
| SYDDYLYYALDY | 62 |
| FYDDYLYYALDY | 63 |
| SADDYLYYALDY | 64 |
| SGDDYLYYALDY | 65 |
| SYDDYLMYALDY | 66 |

TABLE 4-continued

Exemplary VH CDR3 sequences

| VH CDR3 Sequence | SEQ ID NO: |
|---|---|
| SYDDYLYYSLDY | 67 |
| SYDDYLYYAFDY | 68 |
| SYDDYLYYALDT | 69 |
| SADDYLYYSLDY | 70 |
| SADDYLYYAFDY | 71 |
| SADDYLYYSFDY | 72 |
| SADDYLYYSFDT | 73 |
| SHDDYLYYALDY | 98 |

The invention includes anti-IL-6 antibodies comprising a VH domain, wherein the VH comprises a variant CDR3 having an amino acid sequence that is identical to any one of SEQ ID NOs:62 to 73 or 98, except that one or more (e.g., one, two, three, four, five, six, seven, eight, nine, ten, eleven, or twelve) of the amino acids from SEQ ID NOs:62 to 73 or 98 is replaced with any other amino acid. Preferably the anti-IL-6 antibodies comprising a variant CDR3 will specifically bind to an IL-6 antigen.

In addition, the present invention includes anti-IL-6 antibodies comprising a VL domain, wherein the VL comprises any one of the CDR1s set forth in Table 5:

TABLE 5

Exemplary VL CDR1 sequences

| VL CDR1 Sequence | SEQ ID NO: |
|---|---|
| RASQTIDSSYLA | 74 |
| RASQDIDNFLA | 75 |
| RASQTISSYLN | 76 |
| RASQSISIYLN | 77 |
| RASQTISDFLN | 78 |
| WASQSINDYLN | 79 |

The invention includes anti-IL-6 antibodies comprising a VL domain, wherein the VL comprises a variant CDR1 having an amino acid sequence that is identical to any one of SEQ ID NOs:74 to 79, except that one or more (e.g., one, two, three, four, five, six, seven, eight, nine, ten, eleven, or twelve) of the amino acids from SEQ ID NOs:74 to 79 is replaced with any other amino acid. Preferably the anti-IL-6 antibodies comprising a variant CDR1 will specifically bind to an IL-6 antigen.

The invention also includes anti-IL-6 antibodies comprising a VL domain, wherein the VL comprises any one of the CDR2s set forth in Table 6:

TABLE 6

Exemplary VL CDR2 sequences

| VL CDR2 Sequence | SEQ ID NO: |
|---|---|
| GASSRAT | 80 |
| KVSSLRS | 81 |
| AASSLES | 82 |
| ATSTLQS | 83 |
| ASSNLQS | 84 |
| AASNLQI | 85 |

The invention includes anti-IL-6 antibodies comprising a VL domain, wherein the VL comprises a variant CDR2 having an amino acid sequence that is identical to any one of SEQ ID NOs:80 to 85, except that one or more (e.g., one, two, three, four, five, six, or seven) of the amino acids from SEQ ID NOs:80 to 85 is replaced with any other amino acid. Preferably the anti-IL-6 antibodies comprising a variant CDR2 will specifically bind to an IL-6 antigen.

The invention also includes anti-IL-6 antibodies comprising a VL domain, wherein the VL comprises any one of the CDR3s set forth in Table 7:

TABLE 7

Exemplary VL CDR3 sequences

| VL CDR3 Sequence | SEQ ID NO: |
|---|---|
| QQYAKSPIT | 86 |
| QQTRRFPLT | 87 |
| QQANSFPLT | 88 |
| QQTYRNLFT | 89 |
| QQTYSTLGT | 90 |
| QNGHSFPLT | 91 |
| QSGHSFPLT | 92 |
| QHGHSFPLT | 93 |
| QLGHSFPLT | 94 |
| QNAHSFPLT | 95 |
| QNGWSFPLT | 96 |

The invention includes anti-IL-6 antibodies comprising a VL domain, wherein the VL comprises a variant CDR3 having an amino acid sequence that is identical to any one of SEQ ID NOs:86 to 96, except that one or more (e.g., one, two, three, four, five, six, seven, eight, or nine) of the amino acids from SEQ ID NOs:86 to 96 is replaced with any other amino acid. Preferably the anti-IL-6 antibodies comprising a variant CDR3 will specifically bind to an IL-6 antigen.

Figure 1:
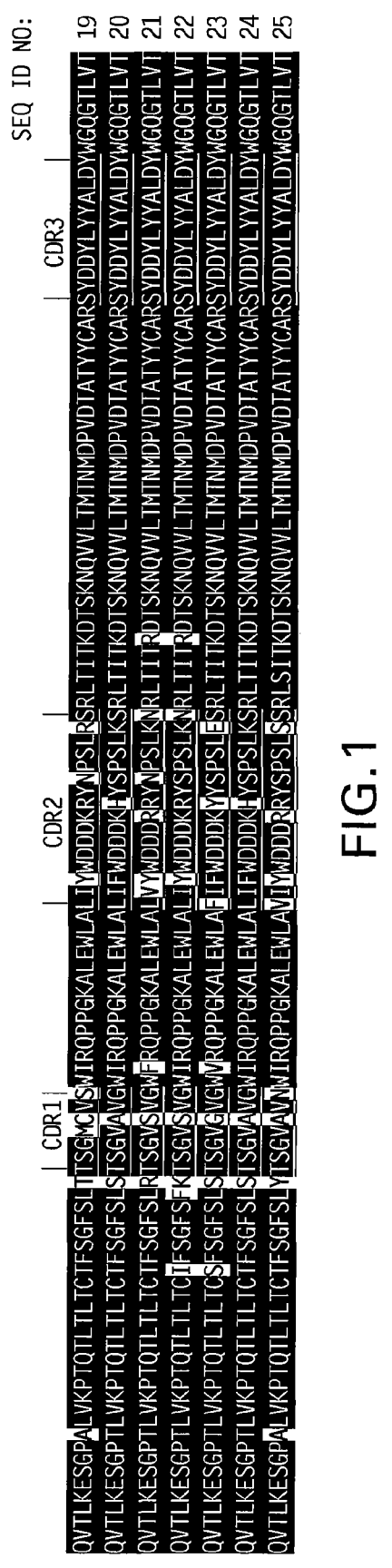

As shown in Example 1, the first generation human variable heavy chain regions (VHs) identified by screening a library of human VHs share significant sequence identity with one another. The amino sequence identities among the human VHs are shown in Table 10 and are illustrated in FIG. 1. For example, the CDR1s of the identified human VHs all share the amino acid sequence T-S-G-$X_1$-$X_2$-V-$X_3$ (SEQ ID NO:99). Additionally, the CDR2s of the identified human VHs all share the amino acid sequence $X_1$-$X_2$-$X_3$-W-D-D-D-$X_4$-$X_5$-Y-$X_6$-P-S-L-$X_7$-$X_8$ (SEQ ID NO:100).

Thus, the invention includes monoclonal antibodies comprising a variable heavy chain CDR1 (VH-CDR1) having the amino acid sequence T-S-G-$X_1$-$X_2$-V-$X_3$ (SEQ ID NO:99), wherein $X_1$, $X_2$ and $X_3$ can be any amino acid. For example, $X_1$, $X_2$ and/or $X_3$ can be isoleucine (I), leucine (L), valine (V), phenylalanine (P), methionine (M), cysteine (C), alanine (A), glycine (G), proline (P), threonine (T), serine (S), tyrosine (Y), tryptophan (W), glutamine (Q), asparagine (N), histidine (H), glutamic acid (E), aspartic acid (D), lysine (K), or arginine (R). In one exemplary embodiment, $X_1$ is methionine (M) or valine (V). In another exemplary embodiment, $X_1$ is valine (V). In another exemplary embodiment, $X_2$ is cysteine (C), alanine (A), serine (S) or glycine (G). In another exemplary embodiment, $X_3$ is serine (S) or glycine (G). Preferably, the antibodies of the invention that comprise a VH-CDR1 having the amino acid sequence T-S-G-$X_1$-$X_2$-V-$X_3$ (SEQ ID NO:99) bind specifically to an IL-6 antigen.

The invention also includes monoclonal antibodies comprising a variable heavy chain CDR2 (VH-CDR2) having the amino acid sequence $X_1$-$X_2$-$X_3$-W-D-D-D-$X_4$-$X_5$-Y-$X_6$-P-S-L-$X_7$-$X_8$ (SEQ ID NO:100), wherein $X_1$, $X_2$, $X_3$, $X_4$, $X_5$, $X_6$, $X_7$ and $X_8$ can be any amino acid. For example, $X_1$, $X_2$, $X_3$, $X_4$, $X_5$, $X_6$, $X_7$ and/or $X_8$ can be isoleucine (I), leucine (L), valine (V), phenylalanine (P), methionine (M), cysteine (C), alanine (A), glycine (G), proline (P), threonine (T), serine (S), tyrosine (Y), tryptophan (W), glutamine (Q), asparagine (N), histidine (H), glutamic acid (E), aspartic acid (D), lysine (K), or arginine (R). In one exemplary embodiment, $X_1$ is leucine (L), phenylalanine (F) or valine (V). In another exemplary embodiment, $X_1$ is leucine (L). In another exemplary embodiment, $X_2$ is isoleucine (I) or valine (V). In another exemplary embodiment, $X_2$ is isoleucine (I). In another exemplary embodiment, $X_3$ is tyrosine (Y) or phenylalanine (F). In another exemplary embodiment, $X_4$ is lysine (K) or arginine (R). In another exemplary embodiment, $X_5$ is arginine (R), tyrosine (Y), or histidine (H). In another exemplary embodiment, $X_6$ is serine (S) or asparagine (N). In another exemplary embodiment, wherein $X_6$ is serine (S). In another exemplary embodiment, $X_7$ is arginine (R), lysine (K), glutamic acid (E) or serine (S). In another exemplary embodiment, $X_7$ is lysine (K). In another exemplary embodiment, $X_8$ is serine (S) or asparagine (N). Preferably, the antibodies of the invention that comprise a VH-CDR2 having the amino acid sequence $X_1$-$X_2$-$X_3$-W-D-D-D-$X_4$-$X_5$-Y-$X_6$-P-S-L-$X_7$-$X_8$ (SEQ ID NO:100) bind specifically to an IL-6 antigen.

The invention also includes anti-IL-6 antibodies comprising a VL domain, wherein the VL is identical to any one of SEQ ID NOs:1 to 18 or 33 to 37, except that one or more of the non-CDR (e.g., framework region) amino acids from SEQ ID NOs:1 to 18 or 33 to 37 is replaced with any other amino acid. The invention also includes anti-IL-6 antibodies comprising a VH domain, wherein the VH is identical to any one of SEQ ID NOs:19 to 32 or 38 to 43, except that one or more of the non-CDR (e.g., framework region) amino acids from SEQ ID NOs:19 to 32 or 38 to 43 is replaced with any other amino acid. Preferably the anti-IL-6 antibodies comprising one or more amino acid changes in the framework regions of the VH and/or VK sequences will specifically bind to an IL-6 antigen.

The invention includes antibodies comprising any combination of:
  (1) a variable heavy chain region (VH) set forth herein, or
     a VH comprising one or more CDRs set forth herein; and
  (2) a variable light chain region (VL) set forth herein or a
     VL comprising one or more CDRs set forth herein.

For example, the invention includes anti-IL-6 antibodies comprising any one of the following combinations of VH regions and VL regions: H415 (SEQ ID NO:19) and L112 (SEQ ID NO:1); H415 (SEQ ID NO:19) and L151 (SEQ ID NO:2); H415 (SEQ ID NO:19) and L158 (SEQ ID NO:3); H415 (SEQ ID NO:19) and L159 (SEQ ID NO:4); H415 (SEQ ID NO:19) and L164 (SEQ ID NO:5); H415 (SEQ ID NO:19) and L165 (SEQ ID NO:6); H415 (SEQ ID NO:19) and L166 (SEQ ID NO:7); H415 (SEQ ID NO:19) and L167 (SEQ ID NO:8); H415 (SEQ ID NO:19) and L168 (SEQ ID NO:9); H415 (SEQ ID NO:19) and L169 (SEQ ID NO:10); H415 (SEQ ID NO:19) and L170 (SEQ ID NO:11); H415 (SEQ ID NO:19) and L171 (SEQ ID NO:12); H415 (SEQ ID NO:19) and L172 (SEQ ID NO:13); H415 (SEQ ID NO:19) and L173 (SEQ ID NO:14); H415 (SEQ ID NO:19) and L174 (SEQ ID NO:15); H415 (SEQ ID NO:19) and L175 (SEQ ID NO:16); H415 (SEQ ID NO:19) and L189 (SEQ ID NO:17); H415 (SEQ ID NO:19) and L198 (SEQ ID NO:18); H415 (SEQ ID NO:19) and L314 (SEQ ID NO:33); H415 (SEQ ID NO:19) and L305 (SEQ ID NO:34); H415 (SEQ ID NO:19) and L303 (SEQ ID NO:35); H415 (SEQ ID NO:19) and L298 (SEQ ID NO:36); or H415 (SEQ ID NO:19) and L321 (SEQ ID NO:37).

The invention also includes anti-IL-6 antibodies comprising any one of the following combinations of VH regions and VL regions: H884 (SEQ ID NO:20) and L112 (SEQ ID NO:1); H884 (SEQ ID NO:20) and L151 (SEQ ID NO:2); H884 (SEQ ID NO:20) and L158 (SEQ ID NO:3); H884 (SEQ ID NO:20) and L159 (SEQ ID NO:4); H884 (SEQ ID NO:20) and L164 (SEQ ID NO:5); H884 (SEQ ID NO:20) and L165 (SEQ ID NO:6); H884 (SEQ ID NO:20) and L166 (SEQ ID NO:7); H884 (SEQ ID NO:20) and L167 (SEQ ID NO:8); H884 (SEQ ID NO:20) and L168 (SEQ ID NO:9); H884 (SEQ ID NO:20) and L169 (SEQ ID NO:10); H884 (SEQ ID NO:20) and L170 (SEQ ID NO:11); H884 (SEQ ID NO:20) and L171 (SEQ ID NO:12); H884 (SEQ ID NO:20) and L172 (SEQ ID NO:13); H884 (SEQ ID NO:20) and L173 (SEQ ID NO:14); H884 (SEQ ID NO:20) and L174 (SEQ ID NO:15); H884 (SEQ ID NO:20) and L175 (SEQ ID NO:16); H884 (SEQ ID NO:20) and L189 (SEQ ID NO:17); H884 (SEQ ID NO:20) and L198 (SEQ ID NO:18); H884 (SEQ ID NO:20) and L314 (SEQ ID NO:33); H884 (SEQ ID NO:20) and L305 (SEQ ID NO:34); H884 (SEQ ID NO:20) and L303 (SEQ ID NO:35); H884 (SEQ ID NO:20) and L298 (SEQ ID NO:36); or H884 (SEQ ID NO:20) and L321 (SEQ ID NO:37).

The invention also includes anti-IL-6 antibodies comprising any one of the following combinations of VH regions and VL regions: H1077 (SEQ ID NO:21) and L112 (SEQ ID NO:1); H1077 (SEQ ID NO:21) and L151 (SEQ ID NO:2); H1077 (SEQ ID NO:21) and L158 (SEQ ID NO:3); H1077 (SEQ ID NO:21) and L159 (SEQ ID NO:4); H1077 (SEQ ID NO:21) and L164 (SEQ ID NO:5); H1077 (SEQ ID NO:21) and L165 (SEQ ID NO:6); H1077 (SEQ ID NO:21) and L166 (SEQ ID NO:7); H1077 (SEQ ID NO:21) and L167 (SEQ ID NO:8); H1077 (SEQ ID NO:21) and L168 (SEQ ID NO:9); H1077 (SEQ ID NO:21) and L169 (SEQ ID NO:10); H1077 (SEQ ID NO:21) and L170 (SEQ ID NO:11); H1077 (SEQ ID NO:21) and L171 (SEQ ID NO:12); H1077 (SEQ ID NO:21) and L172 (SEQ ID NO:13); H1077 (SEQ ID NO:21) and L173 (SEQ ID NO:14); H1077 (SEQ ID NO:21) and L174 (SEQ ID NO:15); H1077 (SEQ ID NO:21) and L175 (SEQ ID NO:16); H1077 (SEQ ID NO:21) and L189 (SEQ ID NO:17); H1077 (SEQ ID NO:21) and L198 (SEQ ID NO:18); H1077 (SEQ ID NO:21) and L314 (SEQ ID NO:33); H1077 (SEQ ID NO:21) and L305 (SEQ ID NO:34); H1077 (SEQ ID NO:21)

and L303 (SEQ ID NO:35); H1077 (SEQ ID NO:21) and L298 (SEQ ID NO:36); or H1077 (SEQ ID NO:21) and L321 (SEQ ID NO:37).

The invention also includes anti-IL-6 antibodies comprising any one of the following combinations of VH regions and VL regions: H1078 (SEQ ID NO:22) and L112 (SEQ ID NO:1); H1078 (SEQ ID NO:22) and L151 (SEQ ID NO:2); H1078 (SEQ ID NO:22) and L158 (SEQ ID NO:3); H1078 (SEQ ID NO:22) and L159 (SEQ ID NO:4); H1078 (SEQ ID NO:22) and L164 (SEQ ID NO:5); H1078 (SEQ ID NO:22) and L165 (SEQ ID NO:6); H1078 (SEQ ID NO:22) and L166 (SEQ ID NO:7); H1078 (SEQ ID NO:22) and L167 (SEQ ID NO:8); H1078 (SEQ ID NO:22) and L168 (SEQ ID NO:9); H1078 (SEQ ID NO:22) and L169 (SEQ ID NO:10); H1078 (SEQ ID NO:22) and L170 (SEQ ID NO:11); H1078 (SEQ ID NO:22) and L171 (SEQ ID NO:12); H1078 (SEQ ID NO:22) and L172 (SEQ ID NO:13); H1078 (SEQ ID NO:22) and L173 (SEQ ID NO:14); H1078 (SEQ ID NO:22) and L174 (SEQ ID NO:15); H1078 (SEQ ID NO:22) and L175 (SEQ ID NO:16); H1078 (SEQ ID NO:22) and L189 (SEQ ID NO:17); H1078 (SEQ ID NO:22) and L198 (SEQ ID NO:18); H1078 (SEQ ID NO:22) and L314 (SEQ ID NO:33); H1078 (SEQ ID NO:22) and L305 (SEQ ID NO:34); H1078 (SEQ ID NO:22) and L303 (SEQ ID NO:35); H1078 (SEQ ID NO:22) and L298 (SEQ ID NO:36); or H1078 (SEQ ID NO:22) and L321 (SEQ ID NO:37).

The invention also includes anti-IL-6 antibodies comprising any one of the following combinations of VH regions and VL regions: H1079 (SEQ ID NO:23) and L112 (SEQ ID NO:1); H1079 (SEQ ID NO:23) and L151 (SEQ ID NO:2); H1079 (SEQ ID NO:23) and L158 (SEQ ID NO:3); H1079 (SEQ ID NO:23) and L159 (SEQ ID NO:4); H1079 (SEQ ID NO:23) and L164 (SEQ ID NO:5); H1079 (SEQ ID NO:23) and L165 (SEQ ID NO:6); H1079 (SEQ ID NO:23) and L166 (SEQ ID NO:7); H1079 (SEQ ID NO:23) and L167 (SEQ ID NO:8); H1079 (SEQ ID NO:23) and L168 (SEQ ID NO:9); H1079 (SEQ ID NO:23) and L169 (SEQ ID NO:10); H1079 (SEQ ID NO:23) and L170 (SEQ ID NO:11); H1079 (SEQ ID NO:23) and L171 (SEQ ID NO:12); H1079 (SEQ ID NO:23) and L172 (SEQ ID NO:13); H1079 (SEQ ID NO:23) and L173 (SEQ ID NO:14); H1079 (SEQ ID NO:23) and L174 (SEQ ID NO:15); H1079 (SEQ ID NO:23) and L175 (SEQ ID NO:16); H1079 (SEQ ID NO:23) and L189 (SEQ ID NO:17); H1079 (SEQ ID NO:23) and L198 (SEQ ID NO:18); H1079 (SEQ ID NO:23) and L314 (SEQ ID NO:33); H1079 (SEQ ID NO:23) and L305 (SEQ ID NO:34); H1079 (SEQ ID NO:23) and L303 (SEQ ID NO:35); H1079 (SEQ ID NO:23) and L298 (SEQ ID NO:36); or H1079 (SEQ ID NO:23) and L321 (SEQ ID NO:37).

The invention also includes anti-IL-6 antibodies comprising any one of the following combinations of VH regions and VL regions: H1081 (SEQ ID NO:24) and L112 (SEQ ID NO:1); H1081 (SEQ ID NO:24) and L151 (SEQ ID NO:2); H1081 (SEQ ID NO:24) and L158 (SEQ ID NO:3); H1081 (SEQ ID NO:24) and L159 (SEQ ID NO:4); H1081 (SEQ ID NO:24) and L164 (SEQ ID NO:5); H1081 (SEQ ID NO:24) and L165 (SEQ ID NO:6); H1081 (SEQ ID NO:24) and L166 (SEQ ID NO:7); H1081 (SEQ ID NO:24) and L167 (SEQ ID NO:8); H1081 (SEQ ID NO:24) and L168 (SEQ ID NO:9); H1081 (SEQ ID NO:24) and L169 (SEQ ID NO:10); H1081 (SEQ ID NO:24) and L170 (SEQ ID NO:11); H1081 (SEQ ID NO:24) and L171 (SEQ ID NO:12); H1081 (SEQ ID NO:24) and L172 (SEQ ID NO:13); H1081 (SEQ ID NO:24) and L173 (SEQ ID NO:14); H1081 (SEQ ID NO:24) and L174 (SEQ ID NO:15); H1081 (SEQ ID NO:24) and L175 (SEQ ID NO:16); H1081 (SEQ ID NO:24) and L189 (SEQ ID NO:17); H1081 (SEQ ID NO:24) and L198 (SEQ ID NO:18); H1081 (SEQ ID NO:24) and L314 (SEQ ID NO:33); H1081 (SEQ ID NO:24) and L305 (SEQ ID NO:34); H1081 (SEQ ID NO:24) and L303 (SEQ ID NO:35); H1081 (SEQ ID NO:24) and L298 (SEQ ID NO:36); or H1081 (SEQ ID NO:24) and L321 (SEQ ID NO:37).

The invention also includes anti-IL-6 antibodies comprising any one of the following combinations of VH regions and VL regions: H1089 (SEQ ID NO:25) and L112 (SEQ ID NO:1); H1089 (SEQ ID NO:25) and L151 (SEQ ID NO:2); H1089 (SEQ ID NO:25) and L158 (SEQ ID NO:3); H1089 (SEQ ID NO:25) and L159 (SEQ ID NO:4); H1089 (SEQ ID NO:25) and L164 (SEQ ID NO:5); H1089 (SEQ ID NO:25) and L165 (SEQ ID NO:6); H1089 (SEQ ID NO:25) and L166 (SEQ ID NO:7); H1089 (SEQ ID NO:25) and L167 (SEQ ID NO:8); H1089 (SEQ ID NO:25) and L168 (SEQ ID NO:9); H1089 (SEQ ID NO:25) and L169 (SEQ ID NO:10); H1089 (SEQ ID NO:25) and L170 (SEQ ID NO:11); H1089 (SEQ ID NO:25) and L171 (SEQ ID NO:12); H1089 (SEQ ID NO:25) and L172 (SEQ ID NO:13); H1089 (SEQ ID NO:25) and L173 (SEQ ID NO:14); H1089 (SEQ ID NO:25) and L174 (SEQ ID NO:15); H1089 (SEQ ID NO:25) and L175 (SEQ ID NO:16); H1089 (SEQ ID NO:25) and L189 (SEQ ID NO:17); H1089 (SEQ ID NO:25) and L198 (SEQ ID NO:18); H1089 (SEQ ID NO:25) and L314 (SEQ ID NO:33); H1089 (SEQ ID NO:25) and L305 (SEQ ID NO:34); H1089 (SEQ ID NO:25) and L303 (SEQ ID NO:35); H1089 (SEQ ID NO:25) and L298 (SEQ ID NO:36); or H1089 (SEQ ID NO:25) and L321 (SEQ ID NO:37).

The invention also includes anti-IL-6 antibodies comprising any one of the following combinations of VH regions and VL regions: H1511 (SEQ ID NO:26) and L112 (SEQ ID NO:1); H1511 (SEQ ID NO:26) and L151 (SEQ ID NO:2); H1511 (SEQ ID NO:26) and L158 (SEQ ID NO:3); H1511 (SEQ ID NO:26) and L159 (SEQ ID NO:4); H1511 (SEQ ID NO:26) and L164 (SEQ ID NO:5); H1511 (SEQ ID NO:26) and L165 (SEQ ID NO:6); H1511 (SEQ ID NO:26) and L166 (SEQ ID NO:7); H1511 (SEQ ID NO:26) and L167 (SEQ ID NO:8); H1511 (SEQ ID NO:26) and L168 (SEQ ID NO:9); H1511 (SEQ ID NO:26) and L169 (SEQ ID NO:10); H1511 (SEQ ID NO:26) and L170 (SEQ ID NO:11); H1511 (SEQ ID NO:26) and L171 (SEQ ID NO:12); H1511 (SEQ ID NO:26) and L172 (SEQ ID NO:13); H1511 (SEQ ID NO:26) and L173 (SEQ ID NO:14); H1511 (SEQ ID NO:26) and L174 (SEQ ID NO:15); H1511 (SEQ ID NO:26) and L175 (SEQ ID NO:16); H1511 (SEQ ID NO:26) and L189 (SEQ ID NO:17); H1511 (SEQ ID NO:26) and L198 (SEQ ID NO:18); H1511 (SEQ ID NO:26) and L314 (SEQ ID NO:33); H1511 (SEQ ID NO:26) and L305 (SEQ ID NO:34); H1511 (SEQ ID NO:26) and L303 (SEQ ID NO:35); H1511 (SEQ ID NO:26) and L298 (SEQ ID NO:36); or H1511 (SEQ ID NO:26) and L321 (SEQ ID NO:37).

The invention also includes anti-IL-6 antibodies comprising any one of the following combinations of VH regions and VL regions: H1420 (SEQ ID NO:27) and L112 (SEQ ID NO:1); H1420 (SEQ ID NO:27) and L151 (SEQ ID NO:2); H1420 (SEQ ID NO:27) and L158 (SEQ ID NO:3); H1420 (SEQ ID NO:27) and L159 (SEQ ID NO:4); H1420 (SEQ ID NO:27) and L164 (SEQ ID NO:5); H1420 (SEQ ID NO:27) and L165 (SEQ ID NO:6); H1420 (SEQ ID NO:27) and L166 (SEQ ID NO:7); H1420 (SEQ ID NO:27) and L167 (SEQ ID NO:8); H1420 (SEQ ID NO:27) and L168 (SEQ ID NO:9); H1420 (SEQ ID NO:27) and L169 (SEQ ID NO:10); H1420 (SEQ ID NO:27) and L170 (SEQ ID NO:11); H1420 (SEQ ID NO:27) and L171 (SEQ ID NO:12); H1420 (SEQ ID NO:27) and L172 (SEQ ID NO:13); H1420 (SEQ ID NO:27) and L173 (SEQ ID NO:14); H1420 (SEQ ID NO:27) and L174 (SEQ ID NO:15); H1420 (SEQ ID NO:27) and L175 (SEQ ID NO:16); H1420 (SEQ ID NO:27) and L189 (SEQ ID NO:17); H1420 (SEQ ID NO:27) and L198 (SEQ ID NO:18); H1420 (SEQ ID NO:27) and L314 (SEQ ID NO:33); H1420 (SEQ ID NO:27) and L305 (SEQ ID NO:34); H1420 (SEQ ID NO:27) and L303 (SEQ ID NO:35); H1420 (SEQ ID NO:27) and L298 (SEQ ID NO:36); or H1420 (SEQ ID NO:27) and L321 (SEQ ID NO:37).

The invention also includes anti-IL-6 antibodies comprising any one of the following combinations of VH regions and VL regions: H1432 (SEQ ID NO:28) and L112 (SEQ ID NO:1); H1432 (SEQ ID NO:28) and L151 (SEQ ID NO:2); H1432 (SEQ ID NO:28) and L158 (SEQ ID NO:3); H1432 (SEQ ID NO:28) and L159 (SEQ ID NO:4); H1432 (SEQ ID NO:28) and L164 (SEQ ID NO:5); H1432 (SEQ ID NO:28) and L165 (SEQ ID NO:6); H1432 (SEQ ID NO:28) and L166 (SEQ ID NO:7); H1432 (SEQ ID NO:28) and L167 (SEQ ID NO:8); H1432 (SEQ ID NO:28) and L168 (SEQ ID NO:9); H1432 (SEQ ID NO:28) and L169 (SEQ ID NO:10); H1432 (SEQ ID NO:28) and L170 (SEQ ID NO:11); H1432 (SEQ ID NO:28) and L171 (SEQ ID NO:12); H1432 (SEQ ID NO:28) and L172 (SEQ ID NO:13); H1432 (SEQ ID NO:28) and L173 (SEQ ID NO:14); H1432 (SEQ ID NO:28) and L174 (SEQ ID NO:15); H1432 (SEQ ID NO:28) and L175 (SEQ ID NO:16); H1432 (SEQ ID NO:28) and L189 (SEQ ID NO:17); H1432 (SEQ ID NO:28) and L198 (SEQ ID NO:18); H1432 (SEQ ID NO:28) and L314 (SEQ ID NO:33); H1432 (SEQ ID NO:28) and L305 (SEQ ID NO:34); H1432 (SEQ ID NO:28) and L303 (SEQ ID NO:35); H1432 (SEQ ID NO:28) and L298 (SEQ ID NO:36); or H1432 (SEQ ID NO:28) and L321 (SEQ ID NO:37).

The invention also includes anti-IL-6 antibodies comprising any one of the following combinations of VH regions and VL regions: H1515 (SEQ ID NO:29) and L112 (SEQ ID NO:1); H1515 (SEQ ID NO:29) and L151 (SEQ ID NO:2); H1515 (SEQ ID NO:29) and L158 (SEQ ID NO:3); H1515 (SEQ ID NO:29) and L159 (SEQ ID NO:4); H1515 (SEQ ID NO:29) and L164 (SEQ ID NO:5); H1515 (SEQ ID NO:29) and L165 (SEQ ID NO:6); H1515 (SEQ ID NO:29) and L166 (SEQ ID NO:7); H1515 (SEQ ID NO:29) and L167 (SEQ ID NO:8); H1515 (SEQ ID NO:29) and L168 (SEQ ID NO:9); H1515 (SEQ ID NO:29) and L169 (SEQ ID NO:10); H1515 (SEQ ID NO:29) and L170 (SEQ ID NO:11); H1515 (SEQ ID NO:29) and L171 (SEQ ID NO:12); H1515 (SEQ ID NO:29) and L172 (SEQ ID NO:13); H1515 (SEQ ID NO:29) and L173 (SEQ ID NO:14); H1515 (SEQ ID NO:29) and L174 (SEQ ID NO:15); H1515 (SEQ ID NO:29) and L175 (SEQ ID NO:16); H1515 (SEQ ID NO:29) and L189 (SEQ ID NO:17); H1515 (SEQ ID NO:29) and L198 (SEQ ID NO:18); H1515 (SEQ ID NO:29) and L314 (SEQ ID NO:33); H1515 (SEQ ID NO:29) and L305 (SEQ ID NO:34); H1515 (SEQ ID NO:29) and L303 (SEQ ID NO:35); H1515 (SEQ ID NO:29) and L298 (SEQ ID NO:36); or H1515 (SEQ ID NO:29) and L321 (SEQ ID NO:37).

The invention also includes anti-IL-6 antibodies comprising any one of the following combinations of VH regions and VL regions: H1362 (SEQ ID NO:30) and L112 (SEQ ID NO:1); H1362 (SEQ ID NO:30) and L151 (SEQ ID NO:2); H1362 (SEQ ID NO:30) and L158 (SEQ ID NO:3); H1362 (SEQ ID NO:30) and L159 (SEQ ID NO:4); H1362 (SEQ ID NO:30) and L164 (SEQ ID NO:5); H1362 (SEQ ID NO:30) and L165 (SEQ ID NO:6); H1362 (SEQ ID NO:30) and L166 (SEQ ID NO:7); H1362 (SEQ ID NO:30) and L167 (SEQ ID NO:8); H1362 (SEQ ID NO:30) and L168 (SEQ ID NO:9); H1362 (SEQ ID NO:30) and L169 (SEQ ID NO:10); H1362 (SEQ ID NO:30) and L170 (SEQ ID NO:11); H1362 (SEQ ID NO:30) and L171 (SEQ ID NO:12); H1362 (SEQ ID NO:30) and L172 (SEQ ID NO:13); H1362 (SEQ ID NO:30) and L173 (SEQ ID NO:14); H1362 (SEQ ID NO:30) and L174 (SEQ ID NO:15); H1362 (SEQ ID NO:30) and L175 (SEQ ID NO:16); H1362 (SEQ ID NO:30) and L189 (SEQ ID NO:17); H1362 (SEQ ID NO:30) and L198 (SEQ ID NO:18); H1362 (SEQ ID NO:30) and L314 (SEQ ID NO:33); H1362 (SEQ ID NO:30) and L305 (SEQ ID NO:34); H1362 (SEQ ID NO:30) and L303 (SEQ ID NO:35); H1362 (SEQ ID NO:30) and L298 (SEQ ID NO:36); or H1362 (SEQ ID NO:30) and L321 (SEQ ID NO:37).

The invention also includes anti-IL-6 antibodies comprising any one of the following combinations of VH regions and VL regions: H1437 (SEQ ID NO:31) and L112 (SEQ ID NO:1); H1437 (SEQ ID NO:31) and L151 (SEQ ID NO:2); H1437 (SEQ ID NO:31) and L158 (SEQ ID NO:3); H1437 (SEQ ID NO:31) and L159 (SEQ ID NO:4); H1437 (SEQ ID NO:31) and L164 (SEQ ID NO:5); H1437 (SEQ ID NO:31) and L165 (SEQ ID NO:6); H1437 (SEQ ID NO:31) and L166 (SEQ ID NO:7); H1437 (SEQ ID NO:31) and L167 (SEQ ID NO:8); H1437 (SEQ ID NO:31) and L168 (SEQ ID NO:9); H1437 (SEQ ID NO:31) and L169 (SEQ ID NO:10); H1437 (SEQ ID NO:31) and L170 (SEQ ID NO:11); H1437 (SEQ ID NO:31) and L171 (SEQ ID NO:12); H1437 (SEQ ID NO:31) and L172 (SEQ ID NO:13); H1437 (SEQ ID NO:31) and L173 (SEQ ID NO:14); H1437 (SEQ ID NO:31) and L174 (SEQ ID NO:15); H1437 (SEQ ID NO:31) and L175 (SEQ ID NO:16); H1437 (SEQ ID NO:31) and L189 (SEQ ID NO:17); H1437 (SEQ ID NO:31) and L198 (SEQ ID NO:18); H1437 (SEQ ID NO:31) and L314 (SEQ ID NO:33); H1437 (SEQ ID NO:31) and L305 (SEQ ID NO:34); H1437 (SEQ ID NO:31) and L303 (SEQ ID NO:35); H1437 (SEQ ID NO:31) and L298 (SEQ ID NO:36); or H1437 (SEQ ID NO:31) and L321 (SEQ ID NO:37).

The invention also includes anti-IL-6 antibodies comprising any one of the following combinations of VH regions and VL regions: H1461 (SEQ ID NO:32) and L112 (SEQ ID NO:1); H1461 (SEQ ID NO:32) and L151 (SEQ ID NO:2); H1461 (SEQ ID NO:32) and L158 (SEQ ID NO:3); H1461 (SEQ ID NO:32) and L159 (SEQ ID NO:4); H1461 (SEQ ID NO:32) and L164 (SEQ ID NO:5); H1461 (SEQ ID NO:32) and L165 (SEQ ID NO:6); H1461 (SEQ ID NO:32) and L166 (SEQ ID NO:7); H1461 (SEQ ID NO:32) and L167 (SEQ ID NO:8); H1461 (SEQ ID NO:32) and L168 (SEQ ID NO:9); H1461 (SEQ ID NO:32) and L169 (SEQ ID NO:10); H1461 (SEQ ID NO:32) and L170 (SEQ ID NO:11); H1461 (SEQ ID NO:32) and L171 (SEQ ID NO:12); H1461 (SEQ ID NO:32) and L172 (SEQ ID NO:13); H1461 (SEQ ID NO:32) and L173 (SEQ ID NO:14); H1461 (SEQ ID NO:32) and L174 (SEQ ID NO:15); H1461 (SEQ ID NO:32) and L175 (SEQ ID NO:16); H1461 (SEQ ID NO:32) and L189 (SEQ ID NO:17); H1461 (SEQ ID NO:32) and L198 (SEQ ID NO:18); H1461 (SEQ ID NO:32) and L314 (SEQ ID NO:33); H1461 (SEQ ID NO:32) and L305 (SEQ ID NO:34); H1461 (SEQ ID NO:32) and L303 (SEQ ID NO:35); H1461 (SEQ ID NO:32) and L298 (SEQ ID NO:36); or H1461 (SEQ ID NO:32) and L321 (SEQ ID NO:37).

The invention also includes anti-IL-6 antibodies comprising any one of the following combinations of VH regions and VL regions: H1519 (SEQ ID NO:38) and L112 (SEQ ID NO:1); H1519 (SEQ ID NO:38) and L151 (SEQ ID NO:2); H1519 (SEQ ID NO:38) and L158 (SEQ ID NO:3); H1519 (SEQ ID NO:38) and L159 (SEQ ID NO:4); H1519 (SEQ ID NO:38) and L164 (SEQ ID NO:5); H1519 (SEQ ID NO:38) and L165 (SEQ ID NO:6); H1519 (SEQ ID NO:38) and L166 (SEQ ID NO:7); H1519 (SEQ ID NO:38) and L167 (SEQ ID NO:8); H1519 (SEQ ID NO:38) and L168 (SEQ ID NO:9); H1519 (SEQ ID NO:38) and L169 (SEQ ID NO:10); H1519 (SEQ ID NO:38) and L170 (SEQ ID NO:11); H1519 (SEQ ID NO:38) and L171 (SEQ ID NO:12); H1519 (SEQ ID NO:38) and L172 (SEQ ID NO:13); H1519 (SEQ ID NO:38) and L173 (SEQ ID NO:14); H1519 (SEQ ID NO:38) and L174 (SEQ ID NO:15); H1519 (SEQ ID NO:38) and L175 (SEQ ID NO:16); H1519 (SEQ ID NO:38) and L189 (SEQ ID NO:17); H1519 (SEQ ID NO:38) and L198 (SEQ ID NO:18); H1519 (SEQ ID NO:38) and L314 (SEQ ID NO:33); H1519 (SEQ ID NO:38) and L305 (SEQ ID NO:34); H1519 (SEQ ID NO:38) and L303 (SEQ ID NO:35); H1519 (SEQ ID NO:38) and L298 (SEQ ID NO:36); or H1519 (SEQ ID NO:38) and L321 (SEQ ID NO:37).

The invention also includes anti-IL-6 antibodies comprising any one of the following combinations of VH regions and VL regions: H1520 (SEQ ID NO:39) and L112 (SEQ ID NO:1); H1520 (SEQ ID NO:39) and L151 (SEQ ID NO:2); H1520 (SEQ ID NO:39) and L158 (SEQ ID NO:3); H1520 (SEQ ID NO:39) and L159 (SEQ ID NO:4); H1520 (SEQ ID NO:39) and L164 (SEQ ID NO:5); H1520 (SEQ ID NO:39) and L165 (SEQ ID NO:6); H1520 (SEQ ID NO:39) and L166 (SEQ ID NO:7); H1520 (SEQ ID NO:39) and L167 (SEQ ID NO:8); H1520 (SEQ ID NO:39) and L168 (SEQ ID NO:9); H1520 (SEQ ID NO:39) and L169 (SEQ ID NO:10); H1520 (SEQ ID NO:39) and L170 (SEQ ID NO:11); H1520 (SEQ ID NO:39) and L171 (SEQ ID NO:12); H1520 (SEQ ID NO:39) and L172 (SEQ ID NO:13); H1520 (SEQ ID NO:39) and L173 (SEQ ID NO:14); H1520 (SEQ ID NO:39) and L174 (SEQ ID NO:15); H1520 (SEQ ID NO:39) and L175 (SEQ ID NO:16); H1520 (SEQ ID NO:39) and L189 (SEQ ID NO:17); H1520 (SEQ ID NO:39) and L198 (SEQ ID NO:18); H1520 (SEQ ID NO:39) and L314 (SEQ ID NO:33); H1520 (SEQ ID NO:39) and L305 (SEQ ID NO:34); H1520 (SEQ ID NO:39) and L303 (SEQ ID NO:35); H1520 (SEQ ID NO:39) and L298 (SEQ ID NO:36); or H1520 (SEQ ID NO:39) and L321 (SEQ ID NO:37).

The invention also includes anti-IL-6 antibodies comprising any one of the following combinations of VH regions and VL regions: H1521 (SEQ ID NO:40) and L112 (SEQ ID NO:1); H1521 (SEQ ID NO:40) and L151 (SEQ ID NO:2); H1521 (SEQ ID NO:40) and L158 (SEQ ID NO:3); H1521 (SEQ ID NO:40) and L159 (SEQ ID NO:4); H1521 (SEQ ID NO:40) and L164 (SEQ ID NO:5); H1521 (SEQ ID NO:40) and L165 (SEQ ID NO:6); H1521 (SEQ ID NO:40) and L166 (SEQ ID NO:7); H1521 (SEQ ID NO:40) and L167 (SEQ ID NO:8); H1521 (SEQ ID NO:40) and L168 (SEQ ID NO:9); H1521 (SEQ ID NO:40) and L169 (SEQ ID NO:10); H1521 (SEQ ID NO:40) and L170 (SEQ ID NO:11); H1521 (SEQ ID NO:40) and L171 (SEQ ID NO:12); H1521 (SEQ ID NO:40) and L172 (SEQ ID NO:13); H1521 (SEQ ID NO:40) and L173 (SEQ ID NO:14); H1521 (SEQ ID NO:40) and L174 (SEQ ID NO:15); H1521 (SEQ ID NO:40) and L175 (SEQ ID NO:16); H1521 (SEQ ID NO:40) and L189 (SEQ ID NO:17); H1521 (SEQ ID NO:40) and L198 (SEQ ID NO:18); H1521 (SEQ ID NO:40) and L314 (SEQ ID NO:33); H1521 (SEQ ID NO:40) and L305 (SEQ ID NO:34); H1521 (SEQ ID NO:40) and L303 (SEQ ID NO:35); H1521 (SEQ ID NO:40) and L298 (SEQ ID NO:36); or H1521 (SEQ ID NO:40) and L321 (SEQ ID NO:37).

The invention also includes anti-IL-6 antibodies comprising any one of the following combinations of VH regions and VL regions: H1522 (SEQ ID NO:41) and L112 (SEQ ID NO:1); H1522 (SEQ ID NO:41) and L151 (SEQ ID NO:2); H1522 (SEQ ID NO:41) and L158 (SEQ ID NO:3); H1522 (SEQ ID NO:41) and L159 (SEQ ID NO:4); H1522 (SEQ ID NO:41) and L164 (SEQ ID NO:5); H1522 (SEQ ID NO:41) and L165 (SEQ ID NO:6); H1522 (SEQ ID NO:41) and L166 (SEQ ID NO:7); H1522 (SEQ ID NO:41) and L167 (SEQ ID NO:8); H1522 (SEQ ID NO:41) and L168 (SEQ ID NO:9); H1522 (SEQ ID NO:41) and L169 (SEQ ID NO:10); H1522 (SEQ ID NO:41) and L170 (SEQ ID NO:11); H1522 (SEQ ID NO:41) and L171 (SEQ ID NO:12); H1522 (SEQ ID NO:41) and L172 (SEQ ID NO:13); H1522 (SEQ ID NO:41) and L173 (SEQ ID NO:14); H1522 (SEQ ID NO:41) and L174 (SEQ ID NO:15); H1522 (SEQ ID NO:41) and L175 (SEQ ID NO:16); H1522 (SEQ ID NO:41) and L189 (SEQ ID NO:17); H1522 (SEQ ID NO:41) and L198 (SEQ ID NO:18); H1522 (SEQ ID NO:41) and L314 (SEQ ID NO:33); H1522 (SEQ ID NO:41) and L305 (SEQ ID NO:34); H1522 (SEQ ID NO:41) and L303 (SEQ ID NO:35); H1522 (SEQ ID NO:41) and L298 (SEQ ID NO:36); or H1522 (SEQ ID NO:41) and L321 (SEQ ID NO:37).

The invention also includes anti-IL-6 antibodies comprising any one of the following combinations of VH regions and VL regions: H1553 (SEQ ID NO:42) and L112 (SEQ ID NO:1); H1553 (SEQ ID NO:42) and L151 (SEQ ID NO:2); H1553 (SEQ ID NO:42) and L158 (SEQ ID NO:3); H1553 (SEQ ID NO:42) and L159 (SEQ ID NO:4); H1553 (SEQ ID NO:42) and L164 (SEQ ID NO:5); H1553 (SEQ ID NO:42) and L165 (SEQ ID NO:6); H1553 (SEQ ID NO:42) and L166 (SEQ ID NO:7); H1553 (SEQ ID NO:42) and L167 (SEQ ID NO:8); H1553 (SEQ ID NO:42) and L168 (SEQ ID NO:9); H1553 (SEQ ID NO:42) and L169 (SEQ ID NO:10); H1553 (SEQ ID NO:42) and L170 (SEQ ID NO:11); H1553 (SEQ ID NO:42) and L171 (SEQ ID NO:12); H1553 (SEQ ID NO:42) and L172 (SEQ ID NO:13); H1553 (SEQ ID NO:42) and L173 (SEQ ID NO:14); H1553 (SEQ ID NO:42) and L174 (SEQ ID NO:15); H1553 (SEQ ID NO:42) and L175 (SEQ ID NO:16); H1553 (SEQ ID NO:42) and L189 (SEQ ID NO:17); H1553 (SEQ ID NO:42) and L198 (SEQ ID NO:18); H1553 (SEQ ID NO:42) and L314 (SEQ ID NO:33); H1553 (SEQ ID NO:42) and L305 (SEQ ID NO:34); H1553 (SEQ ID NO:42) and L303 (SEQ ID NO:35); H1553 (SEQ ID NO:42) and L298 (SEQ ID NO:36); or H1553 (SEQ ID NO:42) and L321 (SEQ ID NO:37).

The invention also includes anti-IL-6 antibodies comprising any one of the following combinations of VH regions and VL regions: H1579 (SEQ ID NO:43) and L112 (SEQ ID NO:1); H1579 (SEQ ID NO:43) and L151 (SEQ ID NO:2); H1579 (SEQ ID NO:43) and L158 (SEQ ID NO:3); H1579 (SEQ ID NO:43) and L159 (SEQ ID NO:4); H1579 (SEQ ID NO:43) and L164 (SEQ ID NO:5); H1579 (SEQ ID NO:43) and L165 (SEQ ID NO:6); H1579 (SEQ ID NO:43) and L166 (SEQ ID NO:7); H1579 (SEQ ID NO:43) and L167 (SEQ ID NO:8); H1579 (SEQ ID NO:43) and L168 (SEQ ID NO:9); H1579 (SEQ ID NO:43) and L169 (SEQ ID NO:10); H1579 (SEQ ID NO:43) and L170 (SEQ ID NO:11); H1579 (SEQ ID NO:43) and L171 (SEQ ID NO:12); H1579 (SEQ ID NO:43) and L172 (SEQ ID NO:13); H1579 (SEQ ID NO:43) and L173 (SEQ ID NO:14); H1579 (SEQ ID NO:43) and L174 (SEQ ID NO:15); H1579 (SEQ ID NO:43) and L175 (SEQ ID NO:16); H1579 (SEQ ID NO:43) and L189 (SEQ ID NO:17); H1579 (SEQ ID NO:43) and L198 (SEQ ID NO:18); H1579 (SEQ ID NO:43) and L314 (SEQ ID NO:33); H1579 (SEQ ID NO:43) and L305 (SEQ ID NO:34); H1579 (SEQ ID NO:43) and L303 (SEQ ID NO:35); H1579 (SEQ ID NO:43) and L298 (SEQ ID NO:36); or H1579 (SEQ ID NO:43) and L321 (SEQ ID NO:37).

It will be understood by person of ordinary skill in the art that any of the aforementioned antibodies comprising a combination of a VH region and a VL region, may include one or more additional regions (or "domains") that are normally found in antibody molecules, such as, e.g., one or more constant heavy chain regions (e.g., CH1, CH2 and/or CH3), and/or a constant light chain region (CL). Preferably, an antibody comprising a combination of a VH region and a VL region, as set forth herein, will bind specifically to an IL-6 antigen.

Nucleic Acid Molecules, Vectors and Cells

The present invention includes nucleic acid molecules that encode an anti-IL-6 antibody heavy chain comprising any one of the VH regions set forth herein, including any amino acid variants of the VH regions. The invention also includes nucleic acid molecules that encode an anti-IL-6 antibody light chain comprising any one of the VL regions set forth herein, including any amino acid variants of the VL regions. In certain embodiments, the nucleic acid molecules encode a portion of an anti-IL-6 antibody heavy chain or a portion of an anti-IL-6 antibody light chain. For example, the invention includes nucleic acid molecules that encode a polypeptide comprising one or more CDR of an anti-IL-6 VH set forth herein, including any one of the CDRs represented by SEQ ID NOs:51 to 73. The invention also includes nucleic acid molecules that encode a polypeptide comprising one or more CDR of an anti-IL-6 VL set forth herein, including any one of the CDRs represented by SEQ ID NOs:74 to 96.

The present invention also includes nucleic acid molecules that encode any of the VH regions set forth herein, including any one of the VH regions represented by SEQ ID NOs:19 to 32 and 38 to 43. The invention includes nucleic acid molecules that encode a VH region having an amino acid sequence that is at least at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to any one of SEQ ID NOs:19 to 32 and 38 to 43, wherein an antibody comprising the VH region specifically binds to IL-6.

The present invention also includes nucleic acid molecules that encode any of the VL regions set forth herein, including any one of the VL regions represented by SEQ ID NOs:1 to 18 and 33 to 37. The invention includes nucleic acid molecules that encode a VL region having an amino acid sequence that is at least at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to any one of SEQ ID NOs:1 to 18 and 33 to 37, wherein an antibody comprising the VL region specifically binds to IL-6.

The invention also includes expression vectors comprising any of the nucleic acid molecules described herein. Exemplary vectors include plasmids, phagemids, cosmids, viruses and phage nucleic acids or other nucleic acid molecules that are able to replicate autonomously or to be replicated in a prokaryotic or eukaryotic cell. In certain embodiments, the vectors are able to be replicated in a mammalian cell. Typical expression vectors contain transcription and translation terminators, initiation sequences, and promoters useful for regulation of the expression of the nucleic acid molecules of the invention. The vectors may also comprise genetic expression cassettes containing at least one independent terminator sequence, sequences permitting replication of the vector in both eukaryotes and prokaryotes, i.e., shuttle vectors, and selection markers for both prokaryotic and eukaryotic systems. The vectors preferably contain a marker to provide a phenotypic trait for selection of transformed host cells such as conferring resistance to antibiotics such as ampicillin or neomycin.

The nucleic acid molecules of the invention can be under the control of one or more promoters. For example, the nucleic acid molecules can be under the control of a constitutive promoter or an inducible promoter. Exemplary promoters include promoters derived from the human cytomegalovirus, metallothionine promoter, SV-40 early promoter, SV-40 later promoter, murine mammary tumor virus promoter, Rous sarcoma virus promoter, polyhedrin promoter, or other promoters shown effective for expression in eukaryotic cells.

The invention also includes host cells comprising a nucleic acid molecule or a vector of the invention. By "host cell" is meant a cell or population of cells into which a nucleic acid molecule or vector of the invention is introduced. A host cell of the present invention is preferably a eukaryotic cell or cell line, preferably a plant, animal, vertebrate, mammalian, rodent, mouse, primate, or human cell or cell line. By "a population of host cells" is meant a group of cultured cells into which a nucleic acid molecule or vector of the present invention can be introduced and expressed. Any host cells which will support expression from a nucleic acid molecule or vector of the invention is intended. Although it is preferred that a population of host cells be a monoculture, i.e., where each cell in the population is of the same cell type, mixed cultures of cells are also contemplated. Host cells of the present invention may be adherent, i.e., host cells which grow attached to a solid substrate, or, alternatively, the host cells may be in suspension. Host cells may be cells derived from primary tumors, cells derived from metastatic tumors, primary cells, cells which have lost contact inhibition, transformed primary cells, immortalized primary cells, cells which may undergo apoptosis, and cell lines derived therefrom.

The invention also includes methods of producing an antibody of the present invention, the method comprising: (i) culturing a host cell expressing one or more nucleic acid sequences encoding an antibody of the present invention, and (ii) recovering the antibody from the culture medium.

Pharmaceutical Compositions

The anti-IL-6 antibodies of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The pharmaceutical compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The anti-IL-6 antibodies of the present invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an anti-IL-6 antibody of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents. In some embodiments, the one or more additional therapeutic agents is an agent or agents for the treatment of a disease or condition as described herein, in particular a disease or disorder as described in the section entitled "Therapeutic Uses of Anti-IL-6 Antibodies of the Invention." For example, an anti-IL-6 antibody of the invention may be coformulated and/or coadministered with one or more additional antibodies that bind IL-6 or other targets, e.g., antibodies that bind to the IL-6 receptor.

As used herein, the terms "treat" and "treatment" refer to therapeutic treatment, including prophylactic or preventative measures, wherein the object is to prevent or slow down (lessen) an undesired physiological change associated with a disease or disorder. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. "Treatment" can also mean prolonging survival as compared to expected survival if not receiving treatment. Those in need of treatment include those already with the disease or disorder as well as those prone to having the disease or disorder or those in which the disease or disorder is to be prevented.

The pharmaceutical compositions of the invention may include a "therapeutically effective amount" or a "prophylactically effective amount" of an anti-IL-6 antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an anti-IL-6 antibody of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Therapeutic Uses of Anti-IL-6 Antibodies of the Invention

Figure 11:
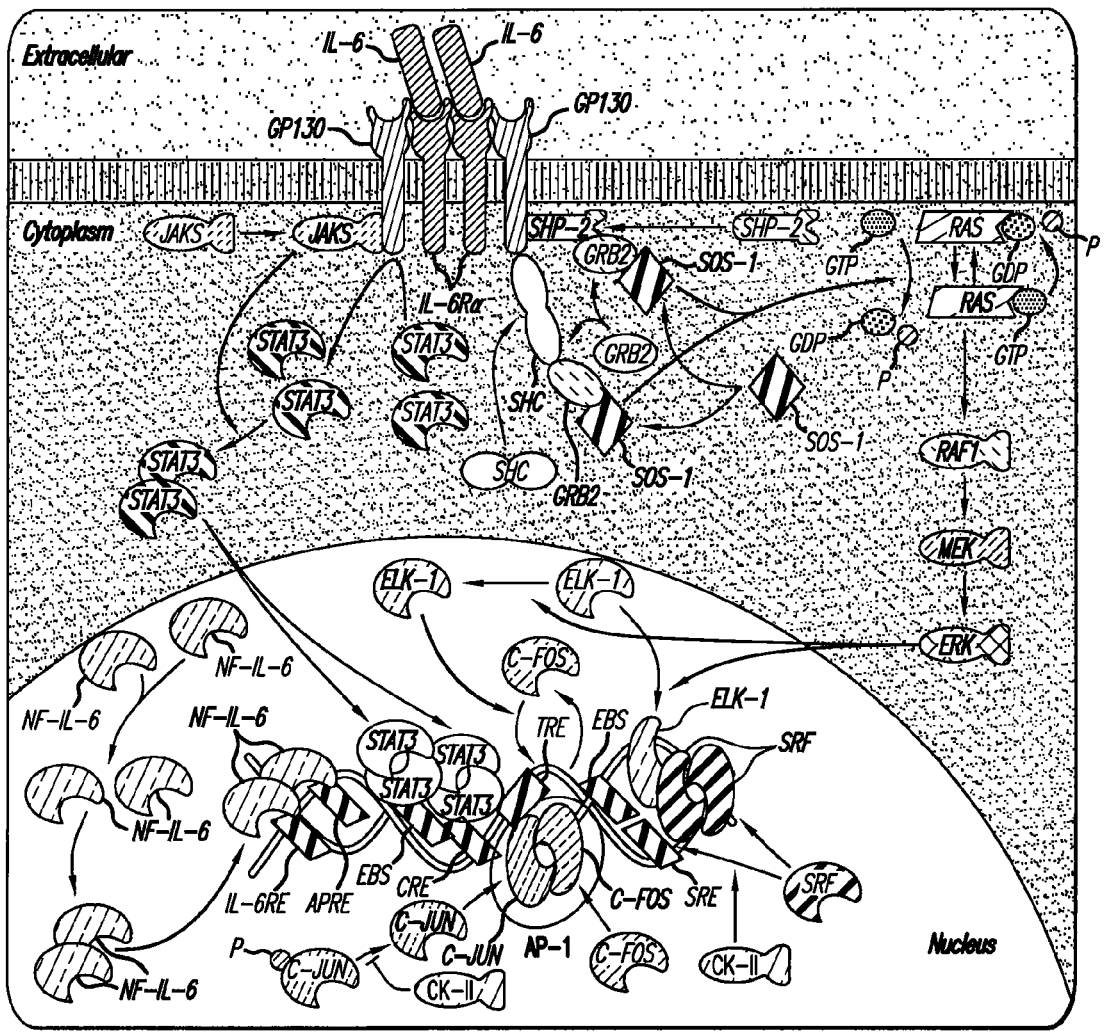
FIG. 11 is a schematic representation of IL-6 signaling pathways (available at BioCarta).

The antibodies of the present invention can be used to treat any disease or disorder mediated by, associated with, or caused by the action of IL-6. For example, the antibodies of the invention can be used to treat a disease or disorder that results from the binding of IL-6 to an IL-6 receptor. The antibodies of the invention may be used to treat a disease or disorder caused by an intracellular signaling event that results, directly or indirectly, from the binding of IL-6 to an IL-6 receptor. Exemplary intracellular IL-6 signaling pathways are illustrated in FIG. 11. The antibodies of the present invention can be used to treat any disease or disorder that is caused by or is associated with the activity of any of the molecules illustrated in FIG. 11, the activities of which are influenced by the binding of IL-6 to an IL-6 receptor.

Thus, the present invention includes methods for treating a disease or disorder mediated by, associated with, or caused by the action of IL-6. The methods comprise administering to a patient in need thereof an anti-IL-6 antibody as disclosed herein. The expression "an anti-IL-6 antibody as disclosed herein" is intended to mean any anti-IL-6 antibody comprising any of the VH regions and/or VL regions set forth herein, as well as any anti-IL-6 antibody comprising a variant of any of the VH regions set forth herein and/or a variant of any of the VL regions set forth herein. An "anti-IL-6 antibody as disclosed herein" is also intended to mean any anti-IL-6 antibody comprising one or more VH CDRs (e.g., CDR1, CDR2, and/or CDR3) and/or one or more VL CDRs (e.g., CDR1, CDR2, and/or CDR3) disclosed herein. Preferably, the antibodies bind specifically to an IL-6 antigen.

In some embodiments, the disease or disorder to be treated is selected from the group consisting of an autoimmune disease or disorder, a disease or disorder associated with aberrant or inappropriate angiogenesis, cancer, osteoarthritis, idiopathic juvenile arthritis, and fibrotic conditions.

In one exemplary embodiment, the invention provides a method for treating an autoimmune disease or disorder, wherein the method comprises administering to a patient in need thereof an anti-IL-6 antibody as disclosed herein. Exemplary autoimmune diseases and disorders that can be treated with an anti-IL-6 antibody of the invention include, e.g., allograft rejection, autoimmune thyroid disease (e.g., Graves' disease and Hashimoto's thyroiditis), autoimmune uveoretinitis, giant cell arteritis, inflammatory bowel diseases (including, e.g., Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, psoriasis, arthritis, rheumatoid arthritis, sarcoidosis, scleroderma, and systemic lupus erythematosus.

The invention includes methods of treating diseases and disorders associated with aberrant or inappropriate angiogenesis, wherein the method comprises administering to a patient in need thereof an anti-IL-6 antibody as disclosed herein. Exemplary diseases and disorders associated with aberrant or inappropriate angiogenesis that can be treated with an anti-IL-6 antibody of the invention include, e.g., cardiovascular diseases such as angioma, angiofibroma, vascular deformity, atherosclerosis, synechia and edemic sclerosis, and opthalmological diseases such as neovascularization after cornea implantation, neovascular glaucoma, diabetic retinopathy, angiogenic corneal disease, macular degeneration, pterygium, retinal degeneration, retrolental fibroplasias, and granular conjunctivitis. Inflammatory diseases that are associated with inappropriate angiogenesis that can be treated with an anti-IL-6 antibody of the invention include, e.g., arthritis, dermatological diseases such as psoriasis, telangiectasis, pyogenic granuloma, seborrheic dermatitis, venous ulcers, acne, rosacea (acne rosacea or erythematosa), warts (verrucas), eczema, hemangiomas, and lymphangiogenesis.

The invention includes methods of treating a cancer, wherein the method comprises administering to a patient in need thereof an anti-IL-6 antibody as disclosed herein. Exemplary cancers that can be treated with an anti-IL-6 antibody of the invention include, e.g., cancers arising from immune cell abnormalities, including myeloid cancers such as multiple myeloma, and myelogenous leukemia (CML), as well as lymphocytic leukemia (CLL and ALL) and lymphomas, particularly Non-Hodgkin's Lymphoma (NHL). The antibodies of the invention can also be used to treat, e.g., renal carcinoma, breast cancer, prostate cancer, lymphoma, post-transplant lymphoma, and post-transplant lymphoproliferative disease (also termed posttransplantation lymphoproliferative disorder).

Additional conditions that can be treated with the anti-IL-6 antibodies of the invention include, e.g., osteoarthritis, idiopathic juvenile arthritis, rheumatoid arthritis, and fibrotic conditions (such as internal and external organ scarring).

The invention also includes use of an antibody of the present invention for the manufacture of a medicament for the treatment of a disease or disorder as described herein.

It will be readily apparent to one of ordinary skill in the relevant arts that other suitable modifications and adaptations to the compositions, methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

First Generation of Human Monoclonal Antibodies that Bind Specifically to IL-6

The purpose of this Example was to make human anti-IL-6 monoclonal antibodies starting from the murine IL-6 antibody known as B-E8 (also known as Elsilimomab).

A screening process was carried out using a vaccinia virus based antibody selection platform in order to identify human VH and VK regions that, when paired with the VK or VH regions of the murine B-E8 antibody, formed antibodies that bound specifically to IL-6. The selected human VH and VK were then used to select human VK and VH, respectively, that bound specifically to IL-6. The details of the vaccinia virus based screening platform are disclosed, e.g., in U.S. Patent Appl. Publication No. 2005/0196755. From this screening process, using either murine B-E8 or human VH, 18 different human VK genes were identified. The nucleic acid sequences of the identified human VK genes and their corresponding amino acid sequences were determined. The amino acid sequences of the identified human VK genes is set forth in Table 8, below:

TABLE 8 amino acid sequences of human VK regions identified

| VK | Amino Acid Sequence | SEQ ID NO: |
|---|---|---|
| L112 | DIVMTQSPATLSVTPGDRVSLSC<u>RASQSISDYLH</u>WYQQK SHESPRLLI<u>KSVSQSIS</u>GIPSRFSGSGSGSDFTLSINSV EPEDVGVYYC<u>QNGHSFPLT</u>FGAGTKLELK | 1 |
| L151 | EIVLTQSPGTLSLSPGERATLSC<u>RASQTIDSSYLA</u>WYQQ KPGQAPRLLVY<u>GASSRATG</u>IPDRFSDSGSGTDFTLTISR LEPEDFAVYYC<u>QQYAKSPIT</u>FGQGTKLE | 2 |
| L158 | DVVMTQSPSSVSASVGDRVTITC<u>RASQDIDNFLA</u>WYQQK PGKAPNLLIY<u>KVSSLRS</u>GVPSRFSGSRSGTDFTLTITSL QPEDFATYFC<u>QQTRRFPLT</u>FGPGTKLE | 3 |
| L159 | DIVMTQSPSSLSASVGDRVTITC<u>RASQTISSYLN</u>WYQQK LPGKPPKLLIY<u>AASSLES</u>GVPSRFSGSGSGTEFTLTISS LQPEDLATYYC<u>QQANSFPLT</u>FGGGTKLE | 4 |
| L164 | DIQMTQSPSSLSASVGDRVTITC<u>RASQSISTYLN</u>WYQQK LGKAPKLLIY<u>AASSLQS</u>GVPSRFSGSGSGTDFTLTISSL QPEDLATYYC<u>QQSYRPLT</u>FGGGTKLEIK | 5 |
| L165 | DIQMTQSPSSLSASVGDSVTITC<u>RASQSISIYLN</u>WYQQK PGKAPDLLIY<u>ATSTLQS</u>GVPSRFSGRGSGTHFTLTIDSL QPEDFATYYC<u>QQTYRNLFT</u>FGQGTKLE | 6 |
| L166 | DIQMTQSPSSLSASVGDSVTVTC<u>RASQKMRTYLH</u>WYQQK PGKAPKLLIY<u>DVSFLQN</u>GVPSRFSGRASGTEFTLTISDL QPEDFATYYC<u>QQSYDTPLT</u>FGQGTKLEIK | 7 |
| L167 | DVVMTQSPSSVSASVGDRVTITC<u>RASQVIDSWLH</u>WYQRE PGKAPKILIY<u>AATTLQR</u>GVPSRFSGSGFGTEFTLTISGL QPEDFATYFC<u>QQGYSFPIT</u>FGQGTRLEIK | 8 |
| L168 | DVVMTQSPSSLSASVGGRVTITC<u>RASQTIGDYLN</u>WYQQK PGKAPRLLIY<u>SASIVQS</u>GVPSRFSASGSGTDFTLTISSL QPEDFATYSC<u>QQSYSFPLT</u>FGGGTKLEIK | 9 |
| L169 | EIVLTQSPSSLSASAGDTVTIAC<u>RASQGIRTALA</u>WYQQK PGRNPKLLI<u>SEAYRLQS</u>GVSPKFSGSGFGTDFTLTINSL QPEDFATYYC<u>QQFNDFPLT</u>FGGGTKLEIK | 10 |
| L170 | DIQMTQSPSTLSASVGDRVTITC<u>RASQSISRWLA</u>WYQQK PGKAPKLLI<u>SKASSLEY</u>GVPSRFSGSGSGTEFALTISNV QPEDFATYYC<u>QQSFAVPLT</u>FGGGTKLEIK | 11 |
| L171 | DIQMTQSPSSLSAFVGDGVTMTC<u>WASQSINDYLN</u>WYHQR PGEAPELLVF<u>AASNLQI</u>GVPSRFRGSGSETYFTLTINSL QPEDSGTYFC<u>QQTSSFPLT</u>FGGGTKLE | 12 |
| L172 | DIQMTQSPSSLSASVGDSVTITC<u>RASQTISDFLN</u>WYQQK PGKAPKLLIH<u>ASSNLQS</u>GVPSRFSGSGSGTDFTLTISDL QPEDFATYSC<u>QQTYSTLGT</u>FGQGTRLE | 13 |
| L173 | DVVMTQSPSSLSASVGGRVTITC<u>RASQTIGDYLN</u>WYQQR PGKAPRLLIY<u>SASIVQS</u>GVPSRFSGSGSGTHFTLTISSL QPEDFATYSC<u>QQSYSFPLT</u>FGGGTKLEIK | 14 |
| L174 | DIVMTQSPSSLSASVGDRVTITC<u>RASRNINTYLN</u>WYQQK PGKAPKLLVH<u>SASTLQS</u>GAPSRFSGSGYGTEFTLIISSL QPDDFATYYC<u>QQGYNTLT</u>FGPGTKLE | 15 |
| L175 | EIVLTQSPSSLSASVGDRVTISC<u>RASQNIIDYLN</u>WYQHK PGKVPTLLI<u>SGTSTLQS</u>GVPSRFSGSGFGTDFTLTISSV QPEDVATYYC<u>QQGHGTPLS</u>FGGGTKLEIK | 16 |

TABLE 8-continued amino acid sequences of human VK regions identified

| VK | Amino Acid Sequence | SEQ ID NO: |
|---|---|---|
| L189 | DIQMTQSPSTLSASVGDRVTITC<u>RASQSMSDYLN</u>WYQQK PGKAPKLLIY<u>SASGLQS</u>GVPSRFSGSGSGTDFTLTIINL QPEDVAAYYC<u>QQSFSFPLT</u>FGPGTKLEIK | 17 |
| L198 | DIQMTQSPSSLSAFVGDGVTMTC<u>WASQSINDYLN</u>WYHQR PGEAPELLVF<u>AASNLQI</u>GVPSRFRGSGSETYFTLTINSL QPEDSGTYFC<u>QNGHSFPLT</u>FGGGTKLEI | 18 |

The underlined sequences represent CDRs 1-3, respectively.

In addition, using either the murine B-E8 or human VK, 7 different human VH genes were identified. The nucleic acid sequences of the identified human VH genes and their corresponding amino acid sequences were determined. The amino acid sequences of the identified human VH genes is set forth in Table 9, below:

TABLE 9 amino acid sequences of human VH regions identified

| VH | Amino Acid Sequence | SEQ ID NO: |
|---|---|---|
| H415 | QVTLKESGPALVKPTQTLTLTCTFSGFSLT<u>TSGMCVS</u> WIRQPPGKALEWL<u>ALIYWDDDKRYNPSLRS</u>RLTITKD TSKNQVVLTMTNMDPVDTATYYCAR<u>SYDDYLYYALDY</u> WGQGTLVT | 19 |
| H884 | QVTLKESGPALVKPTQTLTLTCTFSGFSLT<u>TSGMCVS</u> WIRQPPGKALEWL<u>ALIYWDDDKRYNPSLRS</u>RLTITKD TSKNQVVLTMTNMDPVDTATYYCAR<u>SHDDYLYYALDY</u> WGQGTLVT | 20 |
| H1077 | QVTLKESGPTLVKPTQTLTLTCTFSGFSLR<u>TSGVSVG</u> WFRQPPGKALEWL<u>ALVYWDDDRRYNPSLKN</u>RLTITRD TSKNQVVLTMTNMDPVDTATYYCAR<u>SYDDYLYYALDY</u> WGQGTLVT | 21 |
| H1078 | QVTLKESGPTLVKPTQTLTLTCIFSGFSFK<u>TSGVSVG</u> WIRQPPGKALEWL<u>ALIYWDDDKRYSPSLKN</u>RLTITRD TSKNQVVLTMTNMDPVDTATYYCAR<u>SYDDYLYYALDY</u> WGQGTLVT | 22 |
| H1079 | QVTLKESGPTLVKPTQTLTLTCSFSGFSLS<u>TSGVGVG</u> WVRQPPGKALEWL<u>AFIFWDDDKYYSPSLES</u>RLTITKD TSKNQVVLTMTNMDPVDTATYYCAR<u>SYDDYLYYALDY</u> WGQGTLVT | 23 |
| H1081 | QVTLKESGPTLVKPTQTLTLTCTFSGFSLS<u>TSGVAVG</u> WIRQPPGKALEWL<u>ALIFWDDDKHYSPSLKS</u>RLTITKD TSKNQVVLTMTNMDPVDTATYYCAR<u>SYDDYLYYALDY</u> WGQGTLVTVSS | 24 |
| H1089 | QVTLKESGPALVKPTQTLTLTCTFSGFSLS<u>TSGMCVS</u> WIRQPPGKALEWL<u>TLIYWDDDKRYSPSLET</u>RLTITKD TSKNQVVLTMTNMDPVDTATYYCAR<u>SYDDYLYYALDY</u> WGQGTLVT | 25 |

The underlined sequences represent CDRs 1-3, respectively.

The amino acid sequences of the human VH regions identified exhibited significant sequence identity to one another as illustrated in Table 10, below:

TABLE 10 amino acid sequence identities among the human VHs

|       | H1079 | H415 | H1081 | H1078 | H1089 | H1077 |
|-------|-------|------|-------|-------|-------|-------|
| H1079 |       | 89   | 94    | 90    | 90    | 89    |
| H415  | 89    |      | 92    | 90    | 95    | 90    |
| H1081 | 94    | 92   |       | 93    | 92    | 91    |
| H1078 | 90    | 90   | 93    |       | 90    | 94    |
| H1089 | 90    | 95   | 92    | 90    |       | 89    |
| H1077 | 89    | 90   | 91    | 94    | 89    |       |

An alignment of the identified human VH regions is depicted in FIG. 1.

All of the identified human VKs were cross-paired with all of the identified human VHs. The antibodies resulting from these cross-pairings were tested for their ability to bind IL-6 by ELISA. The antibodies were also tested for functional activity in blocking assays of IL-6-induced cell proliferation or of IL-6 binding to IL-6R.

The affinity of the selected antibodies for IL-6 was measured by ELISA, based on the procedure set forth in *J. of Immunology Methods* 77 (1985) 305-319. Briefly, plates were coated with 2 µg/ml of mBE4 capture antibody in coating buffer, 100 µl per well. The plates were incubated overnight. Next, the plates were washed 3 times and tapped dry. The plates were then blocked with 200 µl per well of Assay Diluent or 10% FBS in PBS and incubated for 2 hours. While the plates were blocking, the competition reaction was set up in solution by pre-incubating 65 µl of Ab at about 2 ng/ml concentration with 65 µl of various concentrations of rhIL6 (from 5.12 µg/ml to 5 ng/ml at 1:2 serial dilutions for total 12 different concentrations including one without IL-6). The reaction was left at RT for 3-4 hours. Therefore, final rhIL6 in competition solution was from 98.46, 49.23, 24.62, 12.31, 6.15, 3.08, 1.54, 0.77, 0.38, 0.19, 0.10 and 0 nM, according IL-6 as monomer. Next, the plates were washed 3 times and tapped dry. 50 ng/ml of recombinant human IL-6 in 100 µl was added to each well to BE4 coated plates. The plates were incubated for 1-2 hours. The plates were washed 3 times and tapped dry. Next, 100 µl of mAb samples from above were added to IL-6 captured plates. The plates were incubated at RT for 2 hours. (Therefore, any unbound mAb at this point will be measured by ELISA). Plates were then washed 5 times and tapped dry. 100 µl of detection Ab goat anti-human IgG F(ab)'2-HRP (Jackson lab) was added at 1:20,000 dilutions or 1:40,000 dilutions (depending on lot) and the plates were incubated for 1-2 hours. The plates were washed 7 times and tapped dry. Next, the Developer Substrate (equal parts of each reagent in the kit) was pre-mixed and allowed to warm to room temperature before use. Then 100 µl of Developer was added to each well. The plates were allowed to develop for 15 minutes un-sealed in a drawer in the dark. Finally, developing was stopped by adding 100 µl of 2N $H_2SO_4$ to each well and plates were read as Endpoint at 450 nm-570 mm.

The blocking assay was conducted as described elsewhere herein.

From the VH/VK cross-pairings, thirty-three first generation mAbs were identified. These first generation mAbs are listed in Table 11, below:

TABLE 11

Summary of first generation human anti-IL-6 antibodies

| mAb | VH | VK | Affinity (IC50 in nM) | Blocking Activity on IL-6-Induced Cell Proliferation |
|-----|------|------|------|------|
| 88* | H383 | L112 | 0.5 | ++++ |
| 123 | H884 | L112 | 1.1 |  |
| 179 | H415 | L112 | 0.85-4.2 | ++ |
| 181 | H415 | L159 | 12.9 |  |
| 182 | H415 | L164 | 6.3 |  |
| 183 | H415 | L165 | 1.75 | ++ |
| 184 | H415 | L166 | 2.4 |  |
| 185 | H415 | L167 | 1.5 |  |
| 186 | H415 | L168 | 2.0 |  |
| 187 | H415 | L169 | 2.4 |  |
| 188 | H415 | L170 | 1.4 |  |
| 189 | H415 | L171 | 0.72 |  |
| 190 | H415 | L172 | 1.9 | ++ |
| 191 | H415 | L173 | 1.5 |  |
| 192 | H415 | L174 | 2.3 |  |
| 193 | H415 | L175 | 2.7 |  |
| 197 | H884 | L167 | 3.7 |  |
| 201 | H884 | L171 | 2.0 |  |
| 202 | H884 | L172 | 2.4 |  |
| 205 | H884 | L175 | 7.4 |  |
| 237 | H1077 | L158 | 6.5 |  |
| 239 | H1078 | L158 | 9.6 |  |
| 241 | H1079 | L158 | 6.5 |  |
| 242 | H1079 | L159 | 2.2 | ++ |
| 246 | H1081 | L151 | 5.5 |  |
| 247 | H1081 | L158 | 4.0 |  |
| 248 | H1081 | L159 | 2.0 |  |
| 265 | H415 | L189 | 6.2 |  |
| 273 | H884 | L171 |  |  |
| 275 | H415 | L198 | 0.7 | ++ |
| 285 | H1089 | L158 | 2.5 |  |
| 286 | H1089 | L159 | 2.5 |  |
| 297 | H1081 | L172 | 11.5 | + |
| 416 | H1079 | L198 | 0.6 | +++ |

*mAb 88 is a chimeric B-E8 control antibody

As the above Table shows, all of the first generation human anti-IL-6 antibodies obtained exhibited some degree of affinity for IL-6 and functional activity in a blocking assay. Briefly, biotinylated human recombinant IL-6 at 12.5 ng/ml was incubated with anti-IL-6 antibodies at the indicated concentrations for 20 min. on ice. FcR-blocked U266 cells (about 250,000 cells) were then added and co-incubated for another 30 min on ice. After washing, streptavidin-PE was added to reveal IL-6 bound to the cell surface. After washing, the cells were analyzed by flow cytometry.

The ability of certain exemplary first generation mAbs to block IL-6 binding to the IL-6 receptor on U266 cells is depicted in FIG. 2.

This Example therefore demonstrates the production of several biologically functional, human anti-IL-6 monoclonal antibodies.

Example 2

Affinity Improvement of Human Anti-IL-6 Antibodies

Mutagenesis was used to further improve the functional activity of first generation human mAbs identified in Example 1. In particular, PCR-based mutagenesis was used to introduce amino acid sequence changes in the CDR3 of VH (H1079) and VK (L198), of mAb 416.

In order to introduce variability, the sequence NNK was introduced at specific positions in the VH and VK genes, where N can be A, T, G, or C, and K is T or G. Using NNK, all 20 amino acids and 1 stop codon can be introduced at each position (there are 32 possible combinations 4×4×2 with the NNK sequence).

All of the CDR3 residues in both H1079 and L198 were changed, one residue at a time. The light chain (VK) CDR3 has 9 amino acids, and the heavy chain (VH) CDR3 has 12 amino acids. Selected residues in CDR1 and CDR2 of H1079 were changed using this process as well.

To create the mutations, an anti-sense primer that encodes one amino acid replaced with NNK and amplifies CDR3 and Framework Region 4 was paired with a sense primer that hybridizes in Framework Region 1 of the chain of interest for a PCR reaction. Each PCR product encodes the entire VK or VH chain and has one amino acid position converted to NNK.

The PCR products were cloned into a mammalian expression vector containing the constant domain of human gamma I (for VH mutants), or kappa (for VK mutants), thereby generating the full length heavy or light chains.

Figure 3:
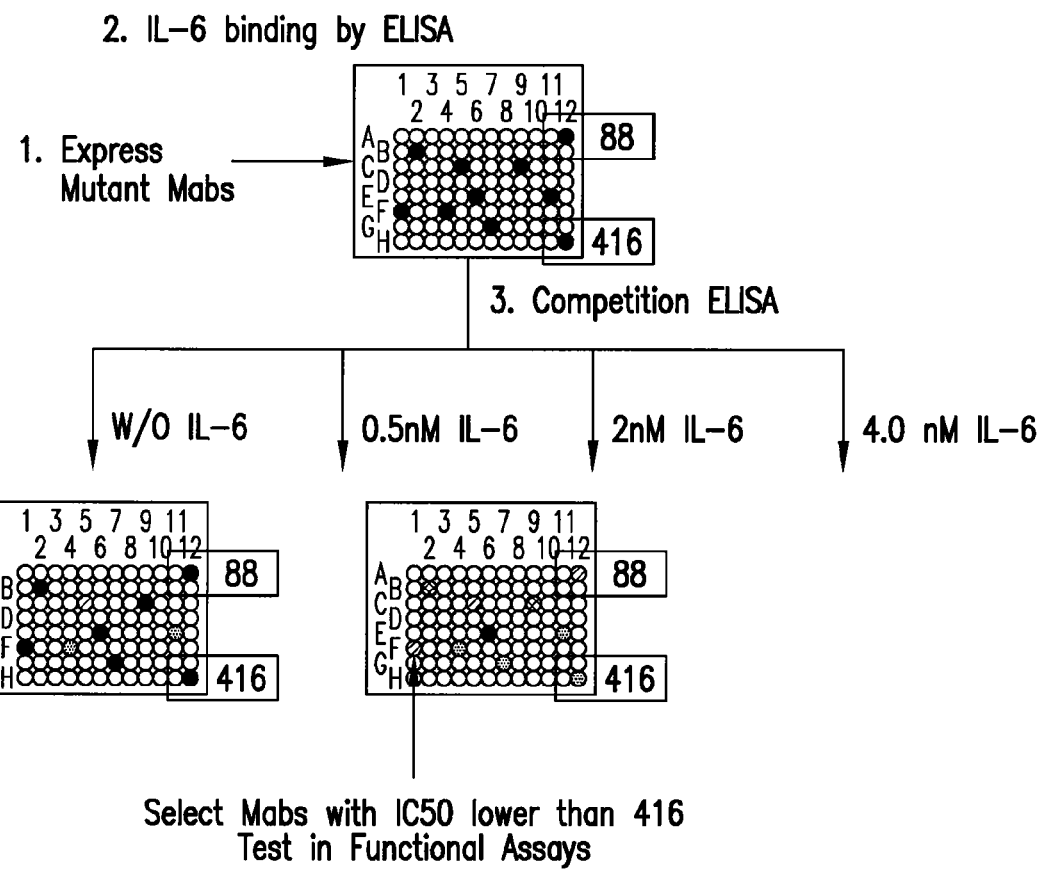
FIG. 3 depicts the general process used for affinity selection of mAbs from libraries generated by site-directed mutagenesis.
Figure 4A:
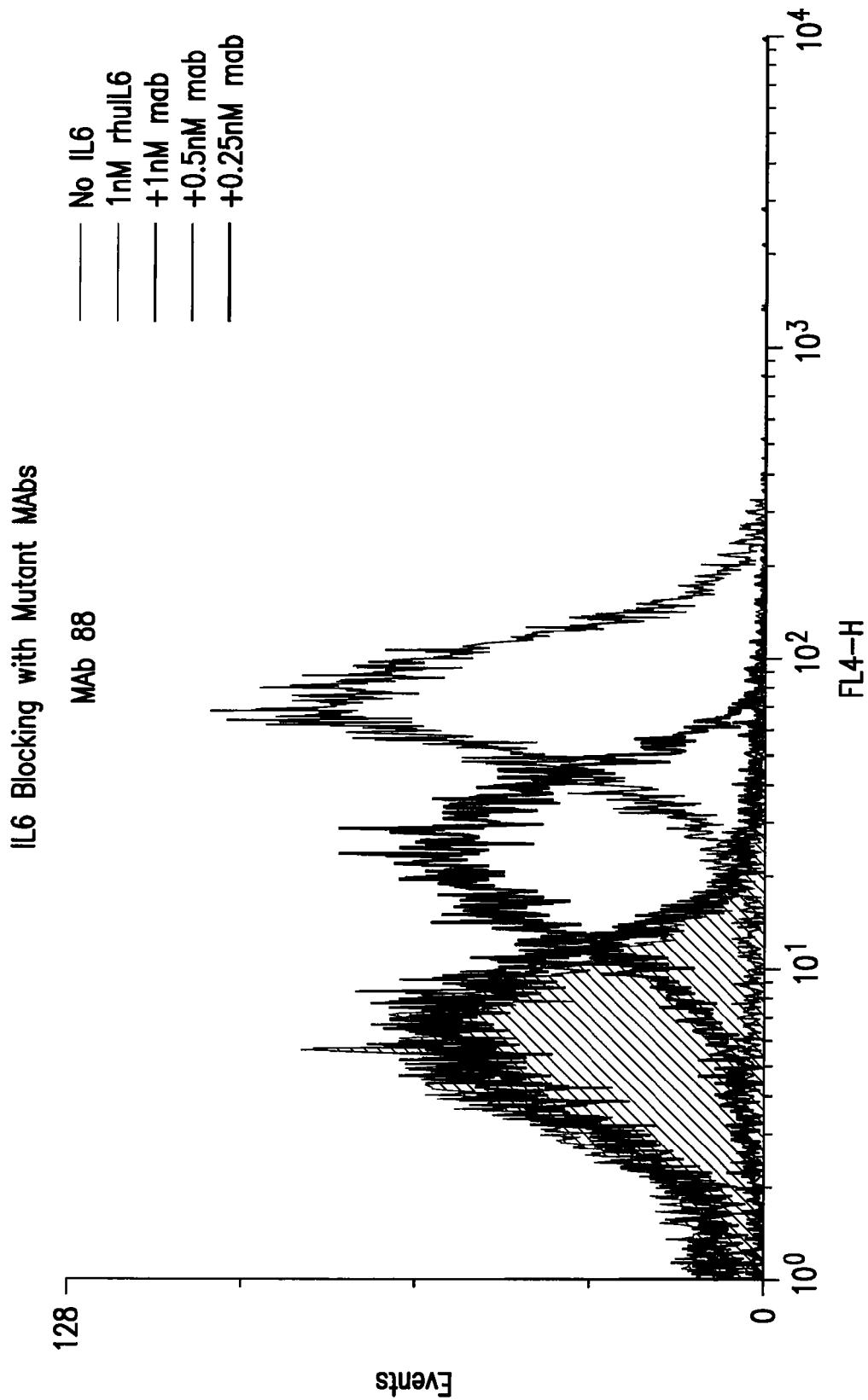

Clones were dispatched in 96 well plate format, with 1 clone per well. Plasmid DNA was purified from each clone and then each clone was expressed with the complementary chain (e.g., a mutated VK would be expressed with a VH) by transfection in CHO cells. Higher affinity binders were selected and characterized. A summary of this procedure is shown in FIG. 3.

When higher affinity mutants were identified, the mutants were sequenced, the resulting mAb was produced by transfection in CHO cells and then tested for specificity, affinity and function in a flow cytometry-based IL-6 blocking assay.

By this process, the following H1079 and L198 variants were obtained:

TABLE 12

H1079 variants obtained by PCR-based mutagenesis

| Amino Acid Change* | Sequence§ | SEQ ID NO: | New VH Designation |
|---|---|---|---|
| S95F | QVTLKESGPTLVKPTQTLTLTCSFSGFSLSTS GVGVGWVRQPPGKALEWLAFIFWDDDKYY SPSLESRLTITKDTSKNQVVLTMTNMDPVDT ATYYCARFYDDYLYYALDYWGQGTLVT | 26 | H1511 |
| Y96A | QVTLKESGPTLVKPTQTLTLTCSFSGFSLSTS GVGVGWVRQPPGKALEWLAFIFWDDDKYY SPSLESRLTITKDTSKNQVVLTMTNMDPVDT ATYYCARSADDYLYYALDYWGQGTLVT | 27 | H1420 |
| Y96G | QVTLKESGPTLVKPTQTLTLTCSFSGFSLSTS GVGVGWVRQPPGKALEWLAFIFWDDDKYY SPSLESRLTITKDTSKNQVVLTMTNMDPVDT ATYYCARSGDDYLYYALDYWGQGTLVT | 28 | H1432 |
| Y100aM | QVTLKESGPTLVKPTQTLTLTCSFSGFSLSTS GVGVGWVRQPPGKALEWLAFIFWDDDKYY SPSLESRLTITKDTSKNQVVLTMTNMDPVDT ATYYCARSYDDYLMYALDYWGQGTLVT | 29 | H1515 |
| A100cS | QVTLKESGPTLVKPTQTLTLTCSFSGFSLSTS GVGVGWVRQPPGKALEWLAFIFWDDDKYY SPSLESRLTITKDTSKNQVVLTMTNMDPVDT ATYYCARSYDDYLYYSLDYWGQGTLVT | 30 | H1362 |
| L100dF | QVTLKESGPTLVKPTQTLTLTCSFSGFSLSTS GVGVGWVRQPPGKALEWLAFIFWDDDKYY SPSLESRLTITKDTSKNQVVLTMTNMDPVDT ATYYCARSYDDYLYYAFDYWGQGTLVT | 31 | H1437 |
| Y102T | QVTLKESGPTLVKPTQTLTLTCSFSGFSLSTS GVGVGWVRQPPGKALEWLAFIFWDDDKYY SPSLESRLTITKDTSKNQVVLTMTNMDPVDT ATYYCARSYDDYLYYALDTWGQGTLVT | 32 | H1461 |

*The amino acid number represents the Kabat number.
≥The boxed residue is the residue that has been changed relative to the sequence of H1079.
The underlined sequences represent CDRs 1-3, respectively.

TABLE 13

L198 variants obtained by PCR-based mutagenesis

| Amino Acid Change* | Sequence≥ | SEQ ID NO: | New VK Designation |
|---|---|---|---|
| N90S | DIQMTQSPSSLSAFVGDGVTMTCWASQSIND YLNWYHQRPGEAPELLVFAASNLQIGVPSRF RGSGSETYFTLTINSLQPEDSGTYFCQSGHSF PLTFGGGTKLEI | 33 | L314 |
| N90H | DIQMTQSPSSLSAFVGDGVTMTCWASQSIND YLNWYHQRPGEAPELLVFAASNLQIGVPSRF RGSGSETYFTLTINSLQPEDSGTYFCQHGHSF PLTFGGGTKLEI | 34 | L305 |

TABLE 13-continued

L198 variants obtained by PCR-based mutagenesis

| Amino Acid Change* | Sequence≋ | SEQ ID NO: | New VK Designation |
|---|---|---|---|
| N90L | DIQMTQSPSSLSAFVGDGVTMTCWASQSIND YLNWYHQRPGEAPELLVFAASNLQIGVPSRF RGSGSETYFTLTINSLQPEDSGTYFCQ<u>L</u>GHSF PLTFGGGTKLEI | 35 | L303 |
| G91A | DIQMTQSPSSLSAFVGDGVTMTCWASQSIND YLNWYHQRPGEAPELLVFAASNLQIGVPSRF RGSGSETYFTLTINSLQPEDSGTYFCQN<u>A</u>HSF PLTFGGGTKLEI | 36 | L298 |
| H92W | DIQMTQSPSSLSAFVGDGVTMTCWASQSIND YLNWYHQRPGEAPELLVFAASNLQIGVPSRF RGSGSETYFTLTINSLQPEDSGTYFCQNG<u>W</u>S FPLTFGGGTKLEI | 37 | L321 |

*The amino acid number represents the Kabat number.
≋The boxed residue is the residue that has been changed relative to the sequence of L198.
The underlined sequences represent CDRs 1-3, respectively.

The following antibodies were made using the H1079 variants set forth in Table 12 paired with L198:

TABLE 14 mAbs made by pairing H1079 variants with L198

| mAb designation | H1079 variant | VK | Affinity (IC50 in nM) |
|---|---|---|---|
| 1123 | H1511 | L198 | 0.11 |
| 926 | H1420 | L198 | 0.07 |
| 963 | H1432 | L198 | 0.09 |
| 1127 | H1515 | L198 | 0.09 |
| 810 | H1362 | L198 | 0.22 |
| 968 | H1437 | L198 | 0.053 |
| 992 | H1461 | L198 | 0.065 |

Monoclonal antibodies 416, 926, 810, 963, 968 and 992 were tested, along with control mAb 88, for the ability to block IL-6 binding to IL-6R-expressing cells. Briefly, human recombinant IL-6 at 1 nM was incubated with anti-IL-6 antibodies at 1 µg/ml -0.1 µg/ml -10 ng/ml -0 ng/ml for 30 min on ice. FcR-blocked U266 cells (about 250,000 cells) were then added and co-incubated for another 30 min on ice. After washing, a purified IL-6-specific mouse antibody (B-F6) was added and incubated with the cells for 30 min on ice. Finally an APC-conjugated polyclonal goat-anti-mouse Fc gamma was added and incubated for 30 min on ice. After washing, the cells were analyzed by flow cytometry by gating on the population of live cells only. Each sample started out with 250,000 cells. All flow cytometry data is based on a minimum of 10,000 live (PI-negative) cells. The results of these experiments are set forth in FIGS. 4A-4G.

The following antibodies were made using the L198 variants set forth in Table 13 paired with H1079:

TABLE 15 mAbs made by pairing L198 variants with H1079

| mAb designation | L198 variant | VH | Affinity (1C50 in nM) |
|---|---|---|---|
| 774 | L314 | H1079 | 0.16 |
| 770 | L305 | H1079 | 0.12 |
| 765 | L298 | H1079 | 0.07 |
| 808 | L321 | H1079 | 0.08 |

Multiple mutations in H1079 were also prepared by the procedure outlined above.

TABLE 16

H1079 multiple mutants obtained by PCR-based mutagenesis

| Amino Acid Changes* | Sequence§ | SEQ ID NO: | New VH Designation |
|---|---|---|---|
| Y96A A100cS | QVTLKESGPTLVKPTQTLTLTCSFSGFSLSTS GVGVGWVRQPPGKALEWLAFIEWDDDKYY SPSLESRLTITKDTSKNQVVLTMTNMDPVDT ATYYCARS<u>A</u>DDYLYY<u>S</u>LDYWGQGTLVT | 38 | H1519 |
| Y96A L100dF | QVTLKESGPTLVKPTQTLTLTCSFSGFSLSTS GVGVGWVRQPPGKALEWLAFIEWDDDKYY SPSLESRLTITKDTSKNQVVLTMTNMDPVDT ATYYCARS<u>A</u>DDYLYYA<u>F</u>DYWGQGTLVT | 39 | H1520 |
| Y96A A100cS L100dF | QVTLKESGPTLVKPTQTLTLTCSFSGFSLSTS GVGVGWVRQPPGKALEWLAFIEWDDDKYY SPSLESRLTITKDTSKNQVVLTMTNMDPVDT ATYYCARS<u>A</u>DDYLYY<u>SF</u>DYWGQGTLVT | 40 | H1521 |

TABLE 16-continued

H1079 multiple mutants obtained by PCR-based mutagenesis

| Amino Acid Changes* | Sequence§ | SEQ ID NO: | New VH Designation |
|---|---|---|---|
| Y96A A100cS L100dF Y102T | QVTLKESGPTLVKPTQTLTLTCSFSGFSLSTS GVGVGWVRQPPGKALEWLAFIFWDDDKYY SPSLESRLTITKDTSKNQVVLTMTNMDPVDT ATYYCARS[A]DDYLYY[SFDT]WGQGTLVT | 41 | H1522 |

*The amino acid number represents the Kabat number.
§The boxed residues are the residues that have been changed relative to the sequence of H1079.
The underlined sequences represent CDRs 1-3, respectively.

In addition, a variant heavy chain, designated H1553, was created by making a single amino acid change (F52W) in CDR2 of H1079. H1553 has the following amino acid sequence:

(SEQ ID NO: 42)
QVLKESGPTVKPTQTLTLTCSFSGFSLSTSGVGVGWVRQPPGKALEWLAF

I[W]WDDDKYYSPSLESRLTITKDTSKNQVVLTMTNMDPVDTATYYCARSYD

DYLYYALDYWGQGTLVT.

Furthermore, the amino acid change found in the CDR2 of H1553 was combined with the four CDR3 amino acid substitutions in H1522 to create H1579, having the following amino acid sequence:

(SEQ ID NO: 43)
QVLKESGPTVKPTQTLTLTCSFSGFSLSTSGVGVGWVRQPPGKALEWLAF

I[W]WDDDKYYSPSLESRLTITKDTSKNQVVLTMTNMDPVDTATYYCARS[A]D

DYLYY[SFDT]WGQGTLVT.

The following mAbs were obtained by combining VH and VK variants, as shown in Table 17, below:

TABLE 17 mAbs created by combining VH and VK variants:

| mAb designation | VH variant | VK variant | Affinity (IC50 in nM) |
|---|---|---|---|
| 1154 | H1522 | L198 | 0.027 |
| 1155 | H1522 | L305 | 0.032 |
| 1156 | H1522 | L314 | 0.023 |
| 1192 | H1553 | L198 | 0.029 |
| 1259 | H1579 | L198 | 0.028 |
| 1337 | H1579 | L305 | 0.047 |
| 1338 | H1579 | L314 | 0.031 |
| 1339 | H1579 | L298 | 0.026 |
| 1340 | H1579 | L321 | 0.028 |

The affinity of exemplary mAbs for IL-6 was determined by IC50 ELISA and by Biacore, as shown in Table 18, below. IC50 ELISA was performed as described above. Affinity analysis by Biacore was performed according to manufacturer protocols using HBS-EP buffer (Biacore AB). Briefly, 100 µg/ml goat anti-human IgG (Sigma-Aldrich Co.) was immobilized on the surface of a CM5 sensor chip (Biacore AB) with affinity for each IL-6 mAb determined by injection of 15 µof 5 µg/ml of the mAb at a flow rate of 5 µ/min followed by injection of 100 µof 40 nM to 1.25 nM human IL-6 (Strathmann Biotec GmbH & Co. KG) at a flow rate of 30 µ/min on a Biacore 2000 system (Biacore AB).

TABLE 18

Affinity of mAbs by IC50 ELISA and Biacore

| mAb | Affinity (nM) by IC50 ELISA | Affinity (nM) by Biacore |
|---|---|---|
| 88 (chimeric B-E8) | 0.01 | 0.02 |
| 1339 | 0.026 | 0.071 |
| 1259 | 0.028 | 0.093 |
| 1340 | 0.028 | not determined |
| 1338 | 0.031 | 0.072 |
| 1337 | 0.047 | not determined |
| 926 | 0.033 | 0.13 |
| 416 | 0.056 | 0.3 |

Monoclonal antibodies 1259, 1337, 1338, 1339 and 1340 are IgG1 kappa. All of the constant domains are the same. The constant domains are in the expression plasmids and therefore do not vary from mAb to mAb. Only the VH and VK domains were selected from the library.

This Example therefore illustrates the production of several additional human anti-IL-6 monoclonal antibodies comprising variant VH and VK chains obtained by PCR-based mutagenesis.

Example 3

Sequences and Vectors

Exemplary Heavy and Light Chain Sequences
The nucleotide sequences encoding the murine mAb B-E8 heavy and light chains are depicted in Table 19:

TABLE 19 heavy and light chain sequences of B-E8 mAb B-E8 heavy chain

GTCGACCCACGCGTCCGGACatggacaggcttacttcttcattcctgct gctgattgtccctgcatatgtcttgtccCAAGTTACTCTAAAAGAGTCT

GGCCCTGGGATATTGAAGCCCTCACAGACCCTCAGTCTGACTTGTTCTT

TCTCTGGGTTTTCACTGAGCACTTCTGGTATGGGTGTAGGCTGGATTCG

TCAGCCTTCAGGGAAGGGTCTGGAGTGGCTGGCACACATTTGGTGGGAT

GATGATAAGTACTATAACCCATCCCTGAAGAGCCAGCTCACAATCTCCA

AGGATACCTCCAGAAACCAGGTATTCCTCAAGATCACCAGTGTGGACAC

TGCAGATACTGCCACTTACTACTGTGCTCGATCCTATGATGACTATCTT

TABLE 19-continued heavy and light chain sequences of B-E8

TACTATGCTTTGGACTACTGGGGTCAAGGAACCTCAGTCACCGTCTCCT

CAGCCAAAACGACACCCCCATCTGTCTATCCACTGGCCCCTGGATCTGC
(SEQ ID NO: 44)

mAb B-E8 light chain

GTCGACCCACGCGTCCGGAAAATTTGAAGatggtgtccacttctcagct ccttggacttttgcttttctggacttcagcctccagatgtGACATTGTG

ATGACTCAGTCTCCAGCCACCCTGTCTGTGACTCCAGGAGATAGAGTCT

TCAACAAAAATCACATGAGTCTCCAAGGCTTCTCATCAAATCTGTTTCC

CAATCCATCTCTGGGATCCCCTCAGGTTCAGTGGCAGTGGCATAGGGTC

AGATTTCACTCTCAGTATCAACAGTGTGGAACCTGAAGATGTTGGAGTG

TATTACTGTCAAAATGGTCACAGCTTTCCGCTCACGTTCGGTGCTGGGA

CCAAGCTGGAGCTGAAA*CGGGCTGATGCTGCACCAACTGTATCCATCTT*

*CCCACCATCATGCGAGATTCGAACATCT* (SEQ ID NO: 45)

Lowercase letters represent the leader sequence
Underlined sequences represent CDRs 1-3, respectively
Italicized letters represent the mouse Cγ1 sequence
Italicized letters represent the mouse Cκ sequence The amino acid sequences of the human mAb 926 heavy and light chains are depicted in Table 20:

TABLE 20 heavy and light chain sequences of mAb 926 mAb 926 heavy chain

MGWSCIILFLVATATGAHSQVTLKESGPTLVKPTQTLTLTCSFSGFSLST

SGVGVGWVRQPPGKALEWLAFIFWDDDKYYSPSLESRLTITKDTSKNQVV

LTMTNMDPVDTATYYCARSADDYLYYALDYWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKEN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK (SEQ ID NO: 46)

mAb 926 light chain

MGWSCIILFLVATATGVHSDIQMTQSPSSLSAFVGDGVTMTCWASQSIND

YLNWYHQRPGEAPELLVFAASNLQIGVPSRFRGSGSETYFTLTINSLQPE

DSGTYFCQNGHSFPLTFGGGTKLEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC (SEQ ID NO: 47)

The amino acid sequences of the human mAb 1339 heavy and light chains are depicted in Table 21:

TABLE 21 heavy and light chain sequences of mAb 1339 mAb 1339 heavy chain

MGWSCIILFLVATATGAHSQVTLKESGPTLVKPTQTLTLTCSFSGFSLST

SGVGVGWVRQPPGKALEWLAFIWWDDDKYYSPSLESRLTITKDTSKNQVV

LTMTNMDPVDTATYYCARSADDYLYYSFDTWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK (SEQ ID NO: 48)

mAb 1339 light chain

MGWSCIILFLVATATGVHSDIQMTQSPSSLSAFVGDGVTMTCWASQSIND

YLNWYHQRPGEAPELLVFAASNLQIGVPSRFRGSGSETYFTLTINSLQPE

DSGTYFCQNAHSFPLTFGGGTKLEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC (SEQ ID NO: 49)

Construction of Double Gene Vector Expressing the Heavy and Light Chains of mAb 1339

Cloning Heavy Chain H1579 into pCONG1

H1579 was subcloned from the original expression vector by digesting the variable region with BssHII and BstEII restriction enzymes into pACeL heavy vector. H1579pAcEL-H was digested with HindIII/ApaI and ligated into HindIII/ApaI-cut pConG1. H1579.pConG1 clone was sequence verified.

Cloning Light Chain L298 into pCONK2

L298 was subcloned from the original expression vector by digesting variable region with ApaL1/XhoI and ligating into a vaccinia transfer vector VKE to provide compatible sequence encoding necessary restriction sites for subsequent dual gene cloning. Variable sequence was PCR amplified to add HindIII site at 5' end and BsiWI site at 3' end. PCR product was cloned into TOPO to facilitate complete digestion with HindIII and BsiWI in subsequent cloning reaction. L298.TOPO was sequence verified, digested with HindIII/BsiWI and ligated into HindIII/BsiWI-cut pConK2. L298.pConK2 was sequence verified.

Creation of Double Gene Vector

Figure 9:
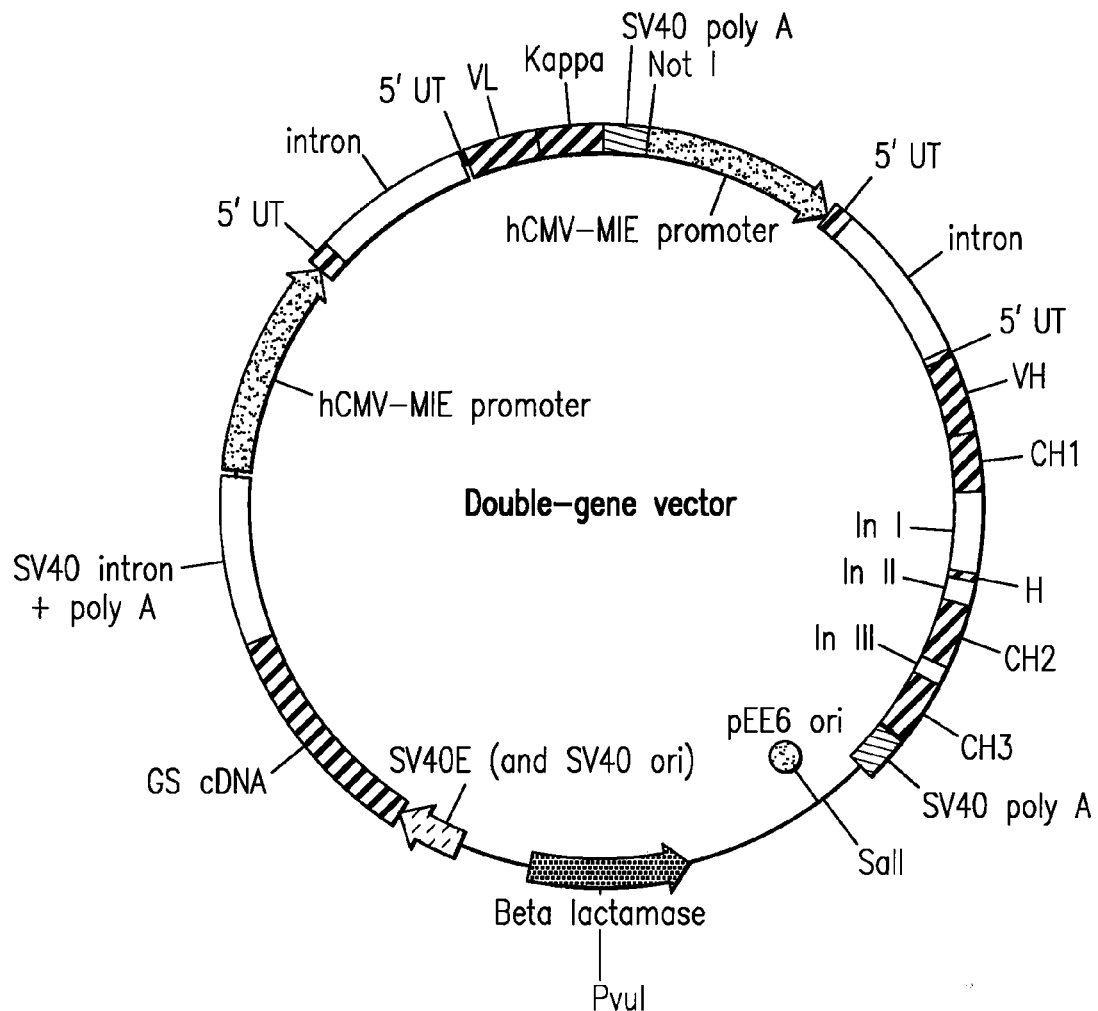
FIG. 9 is a map of the mAb 1339 double gene vector (expressing a heavy chain containing the H1579 heavy chain variable region and a light chain containing the L298 light chain variable region).

Heavy chain expression cassette was released as a NotI/PvuI fragment with a 24 hour digestion of H1579.pConG1. L298.pConK2 was digested with AvrII to prevent re-formation of parental clones, and L298 variable region cassette was released with PvuI and NotI digestion. Following gel purification, Heavy and Light chain cassettes were ligated at a 1:1 ratio in an overnight ligation reaction at 14° C. Colonies were screened for presence of both heavy and light chain inserts by whole-cell PCR, positive clones were confirmed by sequencing. A map of the double gene vector is depicted in FIG. 9. The sequence of the double gene vector is set forth in Table 22:

TABLE 22 nucleotide sequence of mAb 1339 double gene vector (SEQ ID NO: 50)

```
   1 GCTTTCTCAT AGCTCACGCT GTAGGTATCT CAGTTCGGTG TAGGTCGTTC GCTCCAAGCT
  61 GGGCTGTGTG CACGAACCCC CCGTTCAGCC CGACCGCTGC GCCTTATCCG GTAACTATCG
 121 TCTTGAGTCC AACCCGGTAA GACACGACTT ATCGCCACTG GCAGCAGCCA CTGGTAACAG
 181 GATTAGCAGA GCGAGGTATG TAGGCGGTGC TACAGAGTTC TTGAAGTGGT GGCCTAACTA
 241 CGGCTACACT AGAAGAACAG TATTTGGTAT CTGCGCTCTG CTGAAGCCAG TTACCTTCGG
 301 AAAAAGAGTT GGTAGCTCTT GATCCGGCAA ACAAACCACC GCTGGTAGCG GTGGTTTTTT
 361 TGTTTGCAAG CAGCAGATTA CGCGCAGAAA AAAGGATCT CAAGAAGATC CTTTGATCTT
 421 TTCTACGGGG TCTGACGCTC AGTGGAACGA AAACTCACGT TAAGGGATTT TGGTCATGAG
 481 ATTATCAAAA AGGATCTTCA CCTAGATCCT TTTAAATTAA AAATGAAGTT TTAAATCAAT
 541 CTAAAGTATA TATGAGTAAA CTTGGTCTGA CAGTTACCAA TGCTTAATCA GTGAGGCACC
 601 TATCTCAGCG ATCTGTCTAT TTCGTTCATC CATAGTTGCC TGACTCCCCG TCGTGTAGAT
 661 AACTACGATA CGGGAGGGCT TACCATCTGG CCCCAGTGCT GCAATGATAC CGCGAGACCC
 721 ACGCTCACCG GCTCCAGATT TATCAGCAAT AAACCAGCCA GCCGGAAGGG CCGAGCGCAG
 781 AAGTGGTCCT GCAACTTTAT CCGCCTCCAT CCAGTCTATT AATTGTTGCC GGGAAGCTAG
 841 AGTAAGTAGT TCGCCAGTTA ATAGTTTGCG CAACGTTGTT GCCATTGCTA CAGGCATCGT
 901 GGTGTCACGC TCGTCGTTTG GTATGGCTTC ATTCAGCTCC GGTTCCCAAC GATCAAGGCG
 961 AGTTACATGA TCCCCCATGT TGTGCAAAAA AGCGGTTAGC TCCTTCGGTC CTCCGATCGT
1021 TGTCAGAAGT AAGTTGGCCG CAGTGTTATC ACTCATGGTT ATGGCAGCAC TGCATAATTC
1081 TCTTACTGTC ATGCCATCCG TAAGATGCTT TTCTGTGACT GGTGAGTACT CAACCAAGTC
1141 ATTCTGAGAA TAGTGTATGC GGCGACCGAG TTGCTCTTGC CCGGCGTCAA CACGGGATAA
1201 TACCGCGCCA CATAGCAGAA CTTTAAAAGT GCTCATCATT GGAAAACGTT CTTCGGGGCG
1261 AAAACTCTCA AGGATCTTAC CGCTGTTGAG ATCCAGTTCG ATGTAACCCA CTCGTGCACC
1321 CAACTGATCT TCAGCATCTT TTACTTTCAC CAGCGTTTCT GGGTGAGCAA AAACAGGAAG
1381 GCAAAATGCC GCAAAAAAGG GAATAAGGGC GACACGGAAA TGTTGAATAC TCATACTCTT
1441 CCTTTTTCAA TATTATTGAA GCATTTATCA GGGTTATTGT CTCATGAGCG GATACATATT
1501 TGAATGTATT TAGAAAAATA AACAAATAGG GGTTCCGCGC ACATTTCCCC GAAAAGTGCC
1561 ACCTGACGTC TAAGAAACCA TTATTATCAT GACATTAACC TATAAAAATA GGCGTATCAC
1621 GAGGCCCTGA TGGCTCTTTG CGGCACCCAT CGTTCGTAAT GTTCCGTGGC ACCGAGGACA
1681 ACCCTCAAGA GAAAATGTAA TCACACTGGC TCACCTTCGG GTGGGCCTTT CTGCGTTTAT
1741 AAGGAGACAC TTTATGTTTA AGAAGGTTGG TAAATTCCTT GCGGCTTTGG CAGCCAAGCT
1801 AGATCCGGCT GTGGAATGTG TGTCAGTTAG GGTGTGGAAA GTCCCCAGGC TCCCCAGCAG
1861 GCAGAAGTAT GCAAAGCATG CATCTCAATT AGTCAGCAAC CAGGTGTGGA AAGTCCCCAG
1921 GCTCCCCAGC AGGCAGAAGT ATGCAAAGCA TGCATCTCAA TTAGTCAGCA ACCATAGTCC
1981 CGCCCCTAAC TCCGCCCATC CCGCCCCTAA CTCCGCCCAG TTCCGCCCAT TCTCCGCCCC
2041 ATGGCTGACT AATTTTTTTT ATTTATGCAG AGGCCGAGGC CGCCTCGGCC TCTGAGCTAT
2101 TCCAGAAGTA GTGAGGAGGC TTTTTTGGAG GCCTAGGCTT TTGCAAAAAG CTAGCTTGGG
2161 GCCACCGCTC AGAGCACCTT CCACCATGGC CACCTCAGCA AGTTCCCACT TGAACAAAAA
2221 CATCAAGCAA ATGTACTTGT GCCTGCCCCA GGGTGAGAAA GTCCAAGCCA TGTATATCTG
2281 GGTTGATGGT ACTGGAGAAG GACTGCGCTG CAAAACCCGC ACCCTGGACT GTGAGCCCAA
```

TABLE 22-continued nucleotide sequence of mAb 1339 double gene vector

```
2341 GTGTGTAGAA GAGTTACCTG AGTGGAATTT TGATGGCTCT AGTACCTTTC AGTCTGAGGG
2401 CTCCAACAGT GACATGTATC TCAGCCCTGT TGCCATGTTT CGGGACCCCT TCCGCAGAGA
2461 TCCCAACAAG CTGGTGTTCT GTGAAGTTTT CAAGTACAAC CGGAAGCCTG CAGAGACCAA
2521 TTTAAGGCAC TCGTGTAAAC GGATAATGGA CATGGTGAGC AACCAGCACC CCTGGTTTGG
2581 AATGGAACAG GAGTATACTC TGATGGGAAC AGATGGGCAC CCTTTTGGTT GGCCTTCCAA
2641 TGGCTTTCCT GGGCCCCAAG GTCCGTATTA CTGTGGTGTG GGCGCAGACA AAGCCTATGG
2701 CAGGGATATC GTGGAGGCTC ACTACCGCGC CTGCTTGTAT GCTGGGGTCA AGATTACAGG
2761 AACAAATGCT GAGGTCATGC CTGCCCAGTG GGAACTCCAA ATAGGACCCT GTGAAGGAAT
2821 CCGCATGGGA GATCATCTCT GGGTGGCCCG TTTCATCTTG CATCGAGTAT GTGAAGACTT
2881 TGGGGTAATA GCAACCTTTG ACCCCAAGCC CATTCCTGGG AACTGGAATG GTGCAGGCTG
2941 CCATACCAAC TTTAGCACCA AGGCCATGCG GGAGGAGAAT GGTCTGAAGC ACATCGAGGA
3001 GGCCATCGAG AAACTAAGCA AGCGGCACCG GTACCACATT CGAGCCTACG ATCCCAAGGG
3061 GGGCCTGGAC AATGCCCGTG GTCTGACTGG GTTCCACGAA ACGTCCAACA TCAACGACTT
3121 TTCTGCTGGT GTCGCCAATC GCAGTGCCAG CATCCGCATT CCCCGGACTG TCGGCCAGGA
3181 GAAGAAAGGT TACTTTGAAG ACCGCGGCCC CTCTGCCAAT TGTGACCCCT TGCAGTGAC
3241 AGAAGCCATC GTCCGCACAT GCCTTCTCAA TGAGACTGGC GACGAGCCCT TCCAATACAA
3301 AAACTAATTA GACTTTGAGT GATCTTGAGC CTTTCCTAGT TCATCCCACC CCGCCCCAGA
3361 GAGATCTTTG TGAAGGAACC TTACTTCTGT GGTGTGACAT AATTGGACAA ACTACCTACA
3421 GAGATTTAAA GCTCTAAGGT AAATATAAAA TTTTTAAGTG TATAATGTGT TAAACTACTG
3481 ATTCTAATTG TTTGTGTATT TTAGATTCCA ACCTATGGAA CTGATGAATG GGAGCAGTGG
3541 TGGAATGCCT TTAATGAGGA AAACCTGTTT TGCTCAGAAG AAATGCCATC TAGTGATGAT
3601 GAGGCTACTG CTGACTCTCA ACATTCTACT CCTCCAAAAA AGAAGAGAAA GGTAGAAGAC
3661 CCCAAGGACT TTCCTTCAGA ATTGCTAAGT TTTTTGAGTC ATGCTGTGTT TAGTAATAGA
3721 ACTCTTGCTT GCTTTGCTAT TTACACCACA AAGGAAAAAG CTGCACTGCT ATACAAGAAA
3781 ATTATGGAAA AATATTCTGT AACCTTTATA AGTAGGCATA ACAGTTATAA TCATAACATA
3841 CTGTTTTTTC TTACTCCACA CAGGCATAGA GTGTCTGCTA TTAATAACTA TGCTCAAAAA
3901 TTGTGTACCT TTAGCTTTTT AATTTGTAAA GGGGTTAATA AGGAATATTT GATGTATAGT
3961 GCCTTGACTA GAGATCATAA TCAGCCATAC CACATTTGTA GAGGTTTTAC TTGCTTTAAA
4021 AAACCTCCCA CACCTCCCCC TGAACCTGAA ACATAAAATG AATGCAATTG TTGTTGTTAA
4081 CTTGTTTATT GCAGCTTATA ATGGTTACAA ATAAAGCAAT AGCATCACAA ATTTCACAAA
4141 TAAAGCATTT TTTTCACTGC ATTCTAGTTG TGGTTTGTCC AAACTCATCA ATGTATCTTA
4201 TCATGTCTGG ATCTCTAGCT TCGTGTCAAG GACGGTGACT GCAGTGAATA ATAAAATGTG
4261 TGTTTGTCCG AAATACGCGT TTTGAGATTT CTGTCGCCGA CTAAATTCAT GTCGCGCGAT
4321 AGTGGTGTTT ATCGCCGATA GAGATGGCGA TATTGGAAAA ATCGATATTT GAAAATATGG
4381 CATATTGAAA ATGTCGCCGA TGTGAGTTTC TGTGTAACTG ATATCGCCAT TTTTCCAAAA
4441 GTGATTTTTG GCATACGCG ATATCTGGCG ATAGCGCTTA TATCGTTTAC GGGGGATGGC
4501 GATAGAGGAC TTTGGTGACT TGGGCGATTC TGTGTGTCGC AAATATCGCA GTTTCGATAT
4561 AGGTGACAGA CGATATGAGG CTATATCGCC GATAGAGGCG ACATCAAGCT GGCACATGGC
4621 CAATGCATAT CGATCTATAC ATTGAATCAA TATTGGCCAT TAGCCATATT ATTCATTGGT
```

TABLE 22-continued nucleotide sequence of mAb 1339 double gene vector

```
4681 TATATAGCAT AAATCAATAT TGGCTATTGG CCATTGCATA CGTTGTATCC ATATCATAAT
4741 ATGTACATTT ATATTGGCTC ATGTCCAACA TTACCGCCAT GTTGACATTG ATTATTGACT
4801 AGTTATTAAT AGTAATCAAT TACGGGGTCA TTAGTTCATA GCCCATATAT GGAGTTCCGC
4861 GTTACATAAC TTACGGTAAA TGGCCCGCCT GGCTGACCGC CCAACGACCC CCGCCCATTG
4921 ACGTCAATAA TGACGTATGT TCCCATAGTA ACGCCAATAG GGACTTTCCA TTGACGTCAA
4981 TGGGTGGAGT ATTTACGGTA AACTGCCCAC TTGGCAGTAC ATCAAGTGTA TCATATGCCA
5041 AGTACGCCCC CTATTGACGT CAATGACGGT AAATGGCCCG CCTGGCATTA TGCCCAGTAC
5101 ATGACCTTAT GGGACTTTCC TACTTGGCAG TACATCTACG TATTAGTCAT CGCTATTACC
5161 ATGGTGATGC GGTTTTGGCA GTACATCAAT GGGCGTGGAT AGCGGTTTGA CTCACGGGGA
5221 TTTCCAAGTC TCCACCCCAT TGACGTCAAT GGGAGTTTGT TTTGGCACCA AAATCAACGG
5281 GACTTTCCAA AATGTCGTAA CAACTCCGCC CCATTGACGC AAATGGGCGG TAGGCGTGTA
5341 CGGTGGGAGG TCTATATAAG CAGAGCTCGT TTAGTGAACC GTCAGATCGC CTGGAGACGC
5401 CATCCACGCT GTTTTGACCT CCATAGAAGA CACCGGGACC GATCCAGCCT CCGCGGCCGG
5461 GAACGGTGCA TTGGAACGCG GATTCCCCGT GCCAAGAGTG ACGTAAGTAC CGCCTATAGA
5521 GTCTATAGGC CCACCCCCTT GGCTTCTTAT GCATGCTATA CTGTTTTTGG CTTGGGGTCT
5581 ATACACCCCC GCTTCCTCAT GTTATAGGTG ATGGTATAGC TTAGCCTATA GGTGTGGGTT
5641 ATTGACCATT ATTGACCACT CCCCTATTGG TGACGATACT TTCCATTACT AATCCATAAC
5701 ATGGCTCTTT GCCACAACTC TCTTTATTGG CTATATGCCA ATACACTGTC CTTCAGAGAC
5761 TGACACGGAC TCTGTATTTT TACAGGATGG GGTCTCATTT ATTATTTACA AATTCACATA
5821 TACAACACCA CCGTCCCCAG TGCCCGCAGT TTTTATTAAA CATAACGTGG GATCTCACGC
5881 GAATCTCGGG TACGTGTTCC GGACATGGGC TCTTCTCCGG TAGCGGCGGA GCTTCTACAT
5941 CCGAGCCCTG CTCCCATGCC TCCAGCGACT CATGGTCGCT CGGCAGCTCC TTGCTCCTAA
6001 CAGTGGAGGC CAGACTTAGG CACAGCACGA TGCCCACCAC CACCAGTGTG CCGCACAAGG
6061 CCGTGGCGGT AGGGTATGTG TCTGAAAATG AGCTCGGGGA GCGGGCTTGC ACCGCTGACG
6121 CATTTGGAAG ACTTAAGGCA GCGGCAGAAG AAGATGCAGG CAGCTGAGTT GTTGTGTTCT
6181 GATAAGAGTC AGAGGTAACT CCCGTTGCGG TGCTGTTAAC GGTGGAGGGC AGTGTAGTCT
6241 GAGCAGTACT CGTTGCTGCC GCGCGCGCCA CCAGACATAA TAGCTGACAG ACTAACAGAC
6301 TGTTCCTTTC CATGGGTCTT TTCTGCAGTC ACCGTCCTTG ACACGAAGCT TAAGCCGCCA
6361 CCATGGGATG GAGCTGTATC ATCCTCTTCT TGGTAGCAAC AGCTACAGGC GTGCACTCCG
6421 ACATCCAGAT GACCCAGTCT CCGTCCTCCC TGTCTGCTTT TGTGGGAGAC GGAGTCACCA
6481 TGACTTGTTG GGCAAGTCAG AGTATCAACG ACTATTTAAA TTGGTATCAC CAGAGGCCAG
6541 GGGAGGCCCC TGAGCTCCTG GTCTTTGCTG CCTCCAATTT GCAAATTGGA GTCCCGTCAA
6601 GGTTCAGGGG CAGTGGATCT GAGACGTATT TCACTTTAAC TATCAACAGT CTGCAACCTG
6661 AAGATAGTGG CACATACTTC TGTCAGAATG CTCACTCTTT CCCGCTTACT TTCGGCGGAG
6721 GGACCAAGCT CGAGATCAAA CGTACGGTGG CTGCACCATC TGTCTTCATC TTCCCGCCAT
6781 CTGATGAGCA GTTGAAATCT GGAACTGCCT CTGTTGTGTG CCTGCTGAAT AACTTCTATC
6841 CCAGAGAGGC CAAAGTACAG TGGAAGGTGG ATAACGCCCT CCAATCGGGT AACTCCCAGG
6901 AGAGTGTCAC AGAGCAGGAC AGCAAGGACA GCACCTACAG CCTCAGCAGC ACCCTGACGC
6961 TGAGCAAAGC AGACTACGAG AAACACAAAG TCTACGCCTG CGAAGTCACC CATCAGGGCC
```

TABLE 22-continued nucleotide sequence of mAb 1339 double gene vector

```
7021 TGAGCTCGCC CGTCACAAAG AGCTTCAACA GGGGAGAGTG TTAGGAATTC ATTGATCATA
7081 ATCAGCCATA CCACATTTGT AGAGGTTTTA CTTGCTTTAA AAAACCTCCC ACACCTCCCC
7141 CTGAACCTGA AACATAAAAT GAATGCAATT GTTGTTGTTA ACTTGTTTAT TGCAGCTTAT
7201 AATGGTTACA AATAAAGCAA TAGCATCACA AATTTCACAA ATAAAGCATT TTTTTCACTG
7261 CATTCTAGTT GTGGTTTGTC CAAACTCATC AATGTATCTT ATCATGTCTG GCGGCCGCCG
7321 ATATTTGAAA ATATGGCATA TTGAAAATGT CGCCGATGTG AGTTTCTGTG TAACTGATAT
7381 CGCCATTTTT CCAAAAGTGA TTTTTGGGCA TACGCGATAT CTGGCGATAG CGCTTATATC
7441 GTTTACGGGG GATGGCGATA GACGACTTTG GTGACTTGGG CGATTCTGTG TGTCGCAAAT
7501 ATCGCAGTTT CGATATAGGT GACAGACGAT ATGAGGCTAT ATCGCCGATA GAGGCGACAT
7561 CAAGCTGGCA CATGGCCAAT GCATATCGAT CTATACATTG AATCAATATT GGCCATTAGC
7621 CATATTATTC ATTGGTTATA TAGCATAAAT CAATATTGGC TATTGGCCAT TGCATACGTT
7681 GTATCCATAT CATAATATGT ACATTTATAT TGGCTCATGT CCAACATTAC CGCCATGTTG
7741 ACATTGATTA TTGACTAGTT ATTAATAGTA ATCAATTACG GGTCATTAG TTCATAGCCC
7801 ATATATGGAG TTCCGCGTTA CATAACTTAC GGTAAATGGC CCGCCTGGCT GACCGCCCAA
7861 CGACCCCCGC CCATTGACGT CAATAATGAC GTATGTTCCC ATAGTAACGC CAATAGGGAC
7921 TTTCCATTGA CGTCAATGGG TGGAGTATTT ACGGTAAACT GCCCACTTGG CAGTACATCA
7981 AGTGTATCAT ATGCCAAGTA CGCCCCCTAT TGACGTCAAT GACGGTAAAT GGCCCGCCTG
8041 GCATTATGCC CAGTACATGA CCTTATGGGA CTTTCCTACT TGGCAGTACA TCTACGTATT
8101 AGTCATCGCT ATTACCATGG TGATGCGGTT TTGGCAGTAC ATCAATGGGC GTGGATAGCG
8161 GTTTGACTCA CGGGGATTTC CAAGTCTCCA CCCCATTGAC GTCAATGGGA GTTTGTTTTG
8221 GCACCAAAAT CAACGGGACT TTCCAAAATG TCGTAACAAC TCCGCCCCAT TGACGCAAAT
8281 GGGCGGTAGG CGTGTACGGT GGGAGGTCTA TATAAGCAGA GCTCGTTTAG TGAACCGTCA
8341 GATCGCCTGG AGACGCCATC CACGCTGTTT TGACCTCCAT AGAAGACACC GGGACCGATC
8401 CAGCCTCCGC GGCCGGGAAC GGTGCATTGG AACGCGGATT CCCCGTGCCA AGAGTGACGT
8461 AAGTACCGCC TATAGAGTCT ATAGGCCCAC CCCCTTGGCT TCTTATGCAT GCTATACTGT
8521 TTTTGGCTTG GGGTCTATAC ACCCCCGCTT CCTCATGTTA TAGGTGATGG TATAGCTTAG
8581 CCTATAGGTG TGGGTTATTG ACCATTATTG ACCACTCCCC TATTGGTGAC GATACTTTCC
8641 ATTACTAATC CATAACATGG CTCTTTGCCA CAACTCTCTT TATTGGCTAT ATGCCAATAC
8701 ACTGTCCTTC AGAGACTGAC ACGGACTCTG TATTTTTACA GGATGGGGTC TCATTTATTA
8761 TTTACAAATT CACATATACA ACACCACCGT CCCCAGTGCC CGCAGTTTTT ATTAAACATA
8821 ACGTGGGATC TCCACGCGAA TCTCGGGTAC GTGTTCCGGA CATGGGCTCT TCTCCGGTAG
8881 CGGCGGAGCT TCTACATCCG AGCCCTGCTC CCATGCCTCC AGCGACTCAT GGTCGCTCGG
8941 CAGCTCCTTG CTCCTAACAG TGGAGGCCAG ACTTAGGCAC AGCACGATGC CCACCACCAC
9001 CAGTGTGCCG CACAAGGCCG TGGCGGTAGG GTATGTGTCT GAAAATGAGC TCGGGGAGCG
9061 GGCTTGCACC GCTGACGCAT TTGGAAGACT TAAGGCAGCG GCAGAAGAAG ATGCAGGCAG
9121 CTGAGTTGTT GTGTTCTGAT AAGAGTCAGA GGTAACTCCC GTTGCGGTGC TGTTAACGGT
9181 GGAGGGCAGT GTAGTCTGAG CAGTACTCGT TGCTGCCGCG CGCGCCACCA GACATAATAG
9241 CTGACAGACT AACAGACTGT TCCTTTCCAT GGGTCTTTTC TGCAGTCACC GTCCTTGACA
9301 CGAAGCTTAA GCCGCCACCA TGGGATGGAG CTGTATCATC CTCTTCTTGG TAGCAACAGC
```

TABLE 22-continued nucleotide sequence of mAb 1339 double gene vector

```
9361  TACAGGCGCG CACTCCCAAG TCACTTTGAA GGAGTCTGGT CCTACGCTGG TGAAACCCAC
9421  ACAGACCCTC ACGCTGACCT GCAGCTTCTC TGGGTTCTCA CTCAGCACTA GTGGAGTGGG
9481  TGTGGGCTGG GTCCGTCAGC CCCCAGGAAA GGCCCTGGAG TGGCTTGCAT TCATTTGGTG
9541  GGATGATGAT AAGTACTACA GCCCGTCTCT GGAGAGCAGG CTCACCATCA CCAAGGACAC
9601  CTCCAAAAAC CAGGTGGTCC TTACAATGAC CAACATGGAC CCTGTGGACA CAGCCACATA
9661  TTACTGTGCA CGATCCGCTG ATGACTATCT TTACTATTCT TTTGACACGT GGGGCCAGGG
9721  AACCCTGGTC ACCGTCTCCT CAGCCTCCAC CAAGGGCCCA TCGGTCTTCC CCCTGGCACC
9781  CTCCTCCAAG AGCACCTCTG GGGGCACAGC GGCCCTGGGC TGCCTGGTCA AGGACTACTT
9841  CCCCGAACCG GTGACGGTGT CGTGGAACTC AGGCGCCCTG ACCAGCGGCG TGCACACCTT
9901  CCCGGCTGTC CTACAGTCCT CAGGACTCTA CTCCCTCAGC AGCGTGGTGA CCGTGCCCTC
9961  CAGCAGCTTG GGCACCCAGA CCTACATCTG CAACGTGAAT CACAAGCCCA GCAACACCAA
10021 GGTGGACAAG AGAGTTGGTG AGAGGCCAGC ACAGGGAGGG AGGGTGTCTG CTGGAAGCCA
10081 GGCTCAGCGC TCCTGCCTGG ACGCATCCCG CTATGCAGT CCCAGTCCAG GCAGCAAGG
10141 CAGGCCCCGT CTGCCTCTTC ACCCGGAGGC CTCTGCCCGC CCCACTCATG CTCAGGGAGA
10201 GGGTCTTCTG GCTTTTTCCC CAGGCTCTGG GCAGGCACAG GCTAGGTGCC CCTAACCCAG
10261 GCCCTGCACA CAAAGGGGCA GGTGCTGGGC TCAGACCTGC CAAGAGCCAT ATCCGGGAGG
10321 ACCCTGCCCC TGACCTAAGC CCACCCCAAA GGCCAAACTC TCCACTCCCT CAGCTCGGAC
10381 ACCTTCTCTC CTCCCAGATT CCAGTAACTC CCAATCTTCT CTCTGCAGAG CCCAAATCTT
10441 GTGACAAAAC TCACACATGC CCACCGTGCC CAGGTAAGCC AGCCCAGGCC TCGCCCTCCA
10501 GCTCAAGGCG GACAGGTGCC CTAGAGTAG CCTGCATCCA GGGACAGGCC CCAGCCGGGT
10561 GCTGACACGT CCACCTCCAT CTCTTCCTCA GCACCTGAAC TCCTGGGGGG ACCGTCAGTC
10621 TTCCTCTTCC CCCCAAAACC CAAGGACACC CTCATGATCT CCCGGACCCC TGAGGTCACA
10681 TGCGTGGTGG TGGACGTGAG CCACGAAGAC CCTGAGGTCA AGTTCAACTG GTACGTGGAC
10741 GGCGTGGAGG TGCATAATGC CAAGACAAAG CCGCGGGAGG AGCAGTACAA CAGCACGTAC
10801 CGTGTGGTCA GCGTCCTCAC CGTCCTGCAC CAGGACTGGC TGAATGGCAA GGAGTACAAG
10861 TGCAAGGTCT CCAACAAAGC CCTCCCAGCC CCCATCGAGA AAACCATCTC CAAAGCCAAA
10921 GGTGGGACCC GTGGGGTGCG AGGGCCACAT GGACAGAGGC CGGCTCGGCC CACCCTCTGC
10981 CCTGAGAGTG ACCGCTGTAC CAACCTCTGT CCCTACAGGG CAGCCCCGAG AACCACAGGT
11041 GTACACCCTG CCCCCATCCC GGGAGGAGAT GACCAAGAAC CAGGTCAGCC TGACCTGCCT
11101 GGTCAAAGGC TTCTATCCCA GCGACATCGC CGTGGAGTGG GAGAGCAATG GGCAGCCGGA
11161 GAACAACTAC AAGACCACGC CTCCCGTGCT GGACTCCGAC GGCTCCTTCT TCCTCTATAG
11221 CAAGCTCACC GTGGACAAGA GCAGGTGGCA GCAGGGGAAC GTCTTCTCAT GCTCCGTGAT
11281 GCATGAGGCT CTGCACAACC ACTACACGCA GAAGAGCCTC TCCCTGTCTC CGGGTAAATA
11341 GGAATTCATT GATCATAATC AGCCATACCA CATTTGTAGA GGTTTTACTT GCTTTAAAAA
11401 ACCTCCCACA CCTCCCCCTG AACCTGAAAC ATAAAATGAA TGCAATTGTT GTTGTTAACT
11461 TGTTTATTGC AGCTTATAAT GGTTACAAAT AAAGCAATAG CATCACAAAT TTCACAAATA
11521 AAGCATTTTT TCACTGCAT TCTAGTTGTG GTTTGTCCAA ACTCATCAAT GTATCTTATC
11581 ATGTCTGGAT CCTCTACGCC GGACGCATCG TGGCCGGCAT CACCGGCGCC ACAGGTGCGG
11641 TTGCTGGCGC CTATATCGCC GACATCACCG ATGGGGAAGA TCGGGCTCGC CACTTCGGGC
```

TABLE 22-continued nucleotide sequence of mAb 1339 double gene vector

```
11701 TCATGAGCGC TTGTTTCGGC GTGGGTATGG TGGCAGGCCC CGTGGCCGGG GGACTGTTGG

11761 GCGCCATCTC CTTGCATGCA CCATTCCTTG CGGCGGCGGT GCTCAACGGC CTCAACCTAC

11821 TACTGGGCTG CTTCCTAATG CAGGAGTCGC ATAAGGGAGA GCGTCGACCT CGGGCCGCGT

11881 TGCTGGCGTT TTTCCATAGG CTCCGCCCCC CTGACGAGCA TCACAAAAAT CGACGCTCAA

11941 GTCAGAGGTG GCGAAACCCG ACAGGACTAT AAAGATACCA GGCGTTTCCC CCTGGAAGCT

12001 CCCTCGTGCG CTCTCCTGTT CCGACCCTGC CGCTTACCGG ATACCTGTCC GCCTTTCTCC

12061 CTTCGGGAAG CGTGGC
```

Example 4

Creation of a Cho Cell Line Expressing mAb 1339

CHO-K1 HD, a cell line that was adapted to grow in high density suspension culture, was transfected with mAb 1339 dual gene vector (as described in Example 3, above). CHO-K1 HD cells were carried in suspension until time of transfection. The day before the transfection, suspension lines were seeded into 6-well plates in presence of serum to allow attachment of the cells.

Four separate transfections were performed, each separated by 7 days, using subsequent passages of CHO-K1 HD cells and freshly purified and digested DNA from separate plasmid DNA preps. Each week, cells were seeded into two 6-well plates, one plate for a 2.5:1 DNA:lipofectamine ratio, and the other for a 3.0:1 ratio. Therefore, a total of 48 pools were transfected over the course of 4 weeks. Each pool was followed for growth and antibody production levels; not every pool survived drug selection. Pools are denoted by the following nomenclature: mAb name/transfection number, DNA:lipofectamine ratio, letter of transfected well, and dish number. (Example: mAb 1339/1 2.5 B2 pool).

Productivity was measured using a 3-day secretion assay. Data is presented in mAb titer (µg/ml) and specific productivity (µg/million cells/day). Antibody titer and specificity are determined by ELISA. Results of secretion assays from all tested 1339 pools are set forth in Table 23.

TABLE 23 productivity of transfected CHO cells

| IL-6 mAb Pool | mAb conc. (in µg/ml) | SPR (µg/E6 cells/day) | µg/E6 cells | final cell no. (×10⁶) |
|---|---|---|---|---|
| TRANSFECTION 1 | | | | |
| mAb 1339/1 2.5 A1 pool (2E+05) | 6.34 | 3.019 | 9.057 | 1.400 |
| mAb 1339/1 2.5 A1 pool (2E+05) | 7.15 | 2.020 | 6.059 | 2.360 |
| mAb 1339/1 2.5 A1 (5E+05) | 10.10 | 3.367 | 10.100 | 2.000 |
| mAb 1339/1 2.5 A1 (1E+06) | 17.68 | 3.274 | 9.822 | 3.600 |
| mAb 1339/1 2.5 A1 #D2 | 1.60 | 3.048 | 9.143 | 0.350 |
| mAb 1339/1 2.5 A2 pool | 0.40 | 0.437 | 1.311 | 0.610 |
| mAb 1339/1 2.5 B1 pool | 0.78 | 0.765 | 2.294 | 0.680 |
| mAb 1339/1 2.5 B2 pool | 10.18 | 18.244 | 54.731 | 0.372 |
| mAb 1339/1 2.5 B2 (2E+05) | 28.81 | 27.166 | 81.499 | 0.707 |
| mAb 1339/1 2.5 B2 (2E+05) | 23.95 | 20.790 | 62.370 | 0.768 |
| mAb 1339/1 2.5 B2 (2E+05) | 10.58 | 21.374 | 64.121 | 0.330 |
| mAb 1339/1 2.5 B2 (5E+05) | 54.21 | 24.255 | 72.765 | 1.490 |
| mAb 1339/1 2.5 B2 (5E+05) | 37.23 | 20.683 | 62.050 | 1.200 |
| mAb 1339/1 2.5 B2 (1E+06) | 77.50 | 24.603 | 73.810 | 2.100 |
| mAb 1339/1 2.5 C1 pool | 4.29 | 9.226 | 27.677 | 0.310 |
| mAb 1339/1 2.5 C2 pool | 0.26 | 0.231 | 0.692 | 0.737 |
| mAb 1339/1 2.5 C2 #D1 | 0.00 | 0.000 | 0.000 | 1.180 |
| mAb 1339/1 2.5 C2 #D2 | 0.48 | 0.281 | 0.842 | 1.140 |
| TRANSFECTION 2 | | | | |
| mAb 1339/2 2.5 C1 pool | 5.89 | 3.812 | 11.437 | 11.030 |
| mAb b 1339/2 pool 2.5 C2 | 2.95 | 0.624 | 1.873 | 3.150 |
| TRANSFECTION 3 | | | | |
| mAb 1339/3 2.5 A1 pool | 0 | 0.000 | 0.000 | 1.160 |
| mAb 1339/3 2.5 A2 pool | 0.56 | 0.213 | 0.640 | 1.750 |
| mAb 1339/3 2.5 B1 pool | 0 | 0.000 | 0.000 | 1.340 |
| mAb 1339/3 2.5 B2 pool | 0.35 | 0.175 | 0.526 | 1.330 |
| mAb 1339/3 2.5 C1 pool | 0 | 0.000 | 0.000 | 2.040 |
| mAb 1339/3 2.5 C2 pool | 0.71 | 0.601 | 1.802 | 0.788 |
| mAb 1339/3 3.0 A1 pool | 0.80 | 0.368 | 1.103 | 1.450 |
| mAb 1339/3 3.0 A2 pool | 0 | 0.000 | 0.000 | 0.110 |
| mAb 1339/3 3.0 A2 pool | 0 | 0.000 | 0.000 | 0.220 |

TABLE 23-continued productivity of transfected CHO cells

| IL-6 mAb Pool | mAb conc. (in µg/ml) | SPR (µg/E6 cells/day) | µg/E6 cells | final cell no. (×10$^6$) |
|---|---|---|---|---|
| mAb 1339/3 3.0 B1 pool | 0 | 0.000 | 0.000 | 2.730 |
| mAb 1339/3 3.0 B2 pool | 0.89 | 0.436 | 1.309 | 1.360 |
| mAb 1339/3 3.0 C2 pool | 0 | 0.000 | 0.000 | 1.130 |

Figure 10:
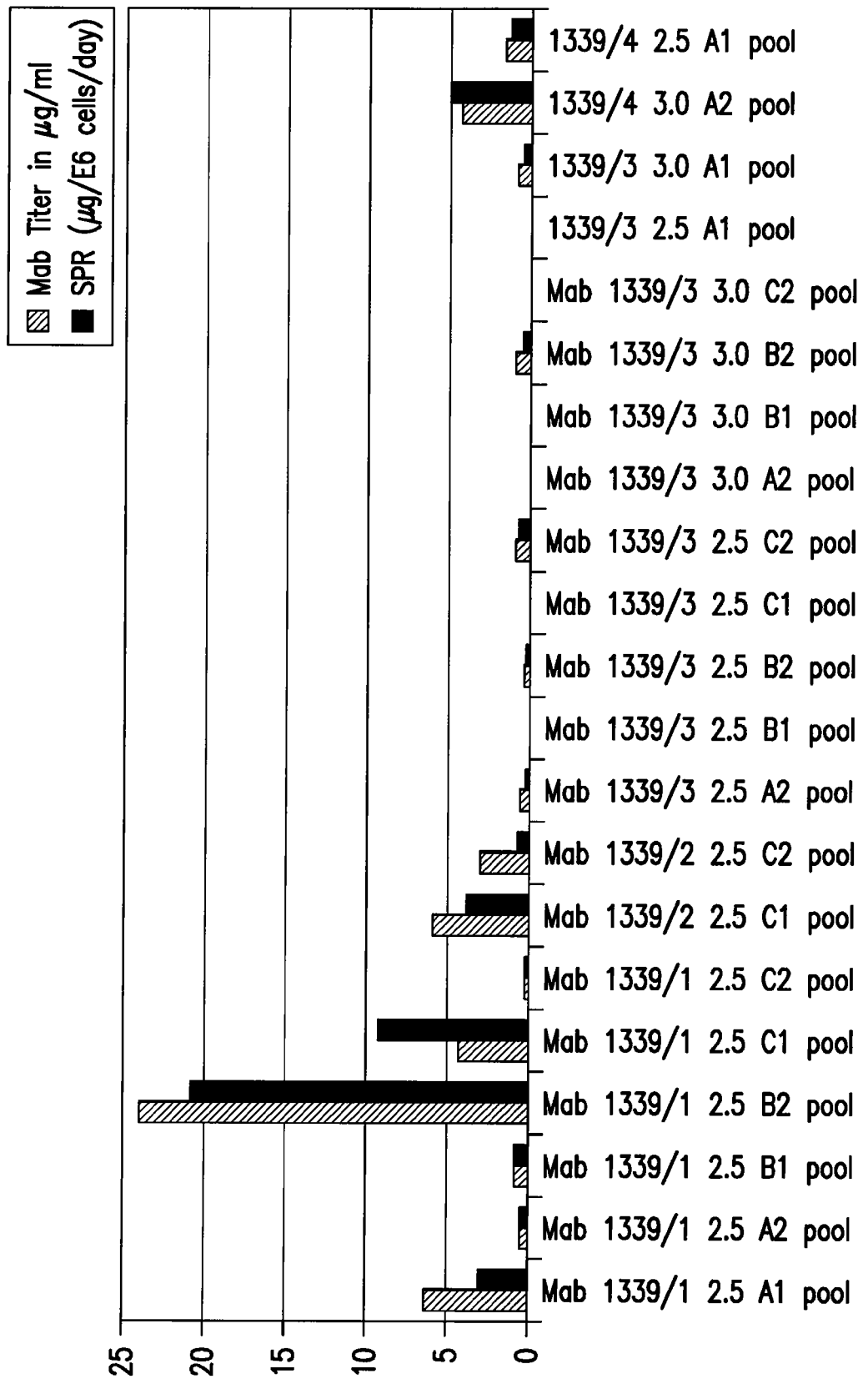
FIG. 10 shows the mAb yields obtained with various CHO-based cell line isolates expressing the mAb 1339 double gene vector.

The mAb yields from small scale secretion experiments is depicted in FIG. 10.

Example 5

Antibody Specificity and Biological Activity

Antibody Specificity

Purified mAb 1339 was tested to confirm specificity for IL-6. Purified mAb 1339 was tested by ELISA for binding to a panel of control antigens, including human insulin, human serum albumin, human hemoglobin, and bovine serum albumin. No non-specific binding was seen to these antigens. (Data not shown).

Figure 5A:
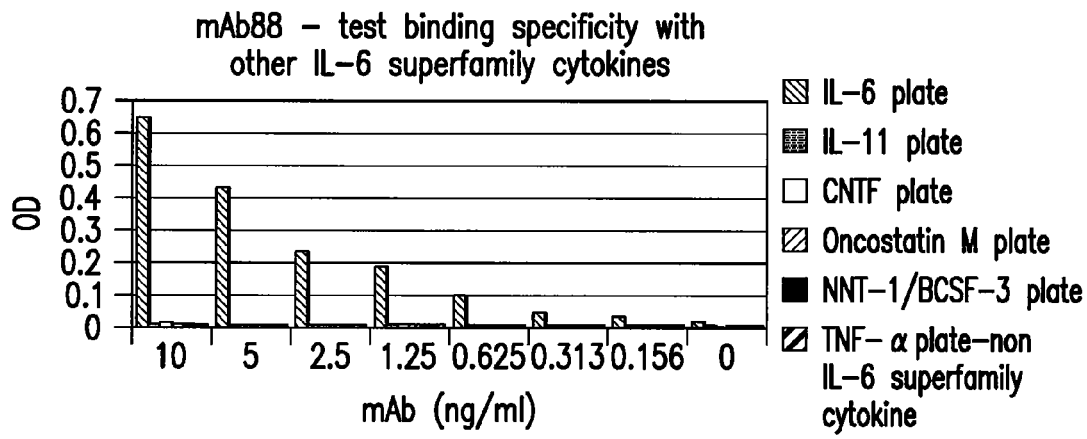
FIGS. 5A and 5B show the results of binding specificity experiments in which a control mAb 88 (chimeric B-E8) (FIG. 5A), or a candidate, affinity-improved human mAb 1339 (FIG. 5B) were tested by ELISA for binding to a panel of IL-6 superfamily members.
Figure 5B:
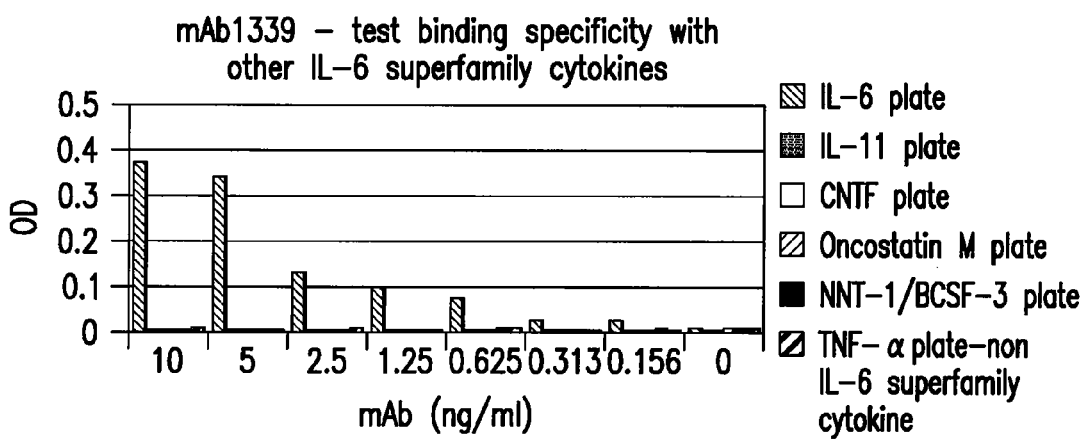

In addition, purified mAb 1339 and control mAb 88 were tested by ELISA for binding to a panel of IL-6 superfamily members: CNFT, oncostatin M, IL-11, and NNT-1. As shown in FIGS. 5A and 5B, neither mAb 1339 nor mAb 88 bound to any of these cytokines in the ELISA.

Inhibition of IL-6-Induced Murine and Human Cell Proliferation

In order to assess the biological activity of the human anti-IL-6 mAbs, their ability to inhibit IL-6-induced murine B9 myeloma cell proliferation (FIG. 12) and IL-6-induced human U266 cell proliferation (FIG. 13) was assessed. The murine B9 cell line is human IL-6 sensitive.

Figure 12:
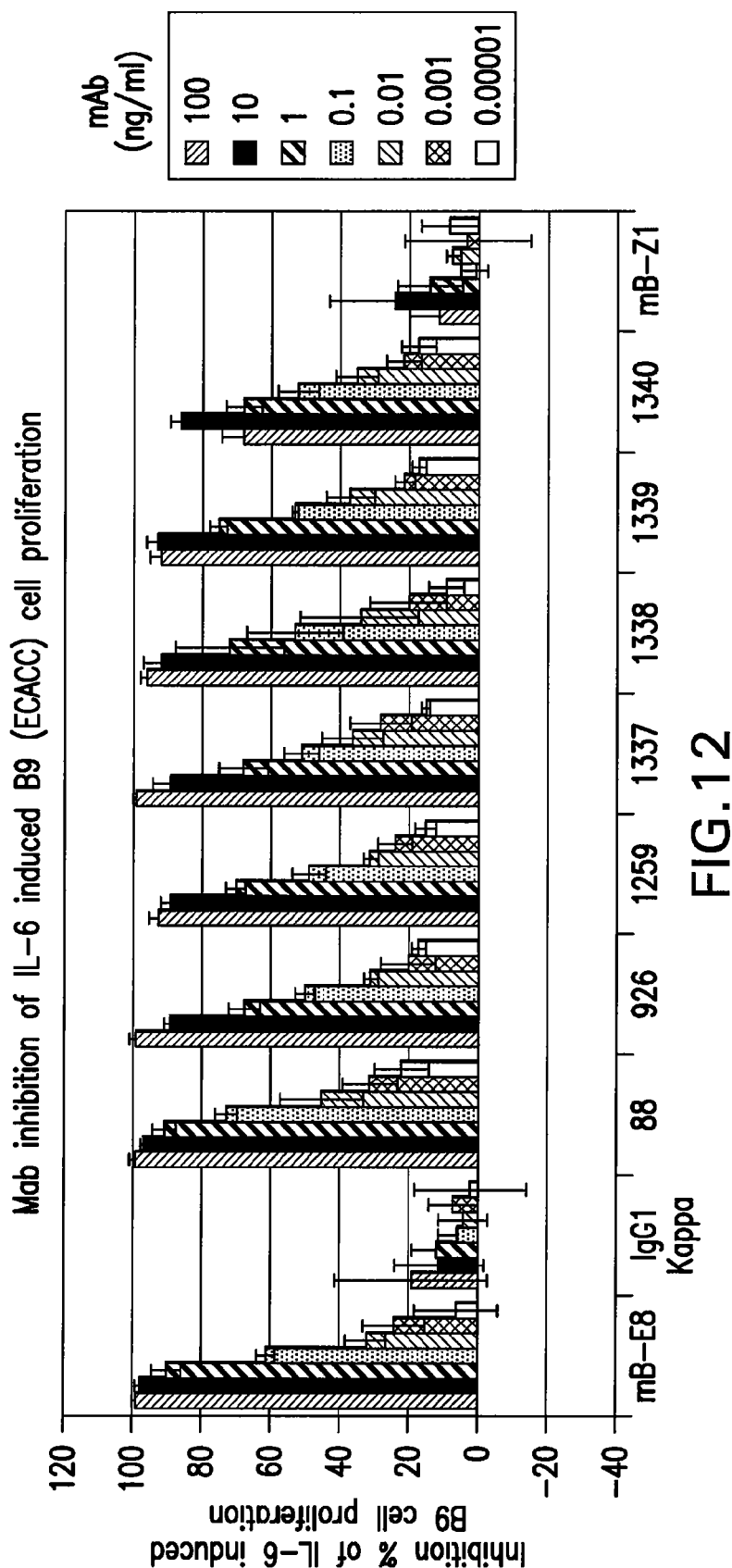
FIG. 12 shows the results of experiments in which IL-6-specific mAbs were tested for their ability to inhibit the IL-6-dependent proliferation of the murine B9 (ECACC) myeloma cell line. IgG1 Kappa and niB-Z1 are human and mouse IgG1 isotype control antibodies, respectively. For each mAb, the seven columns from left to right indicate the percent inhibition of IL-6 (10 pg/ml)-induced B9 cell proliferation at mAb concentrations of 100, 10, 1, 0.1, 0.01, 0.001, and 0.0001 ng/ml, respectively. Each column represents a mean of three experiments +/− standard deviation.

As shown in FIG. 12, mAbs 926, 1259, 1337, 1338, 1339 and 1340 all showed a dose-dependent inhibitory effect on IL-6-induced murine myeloma cell proliferation. For example, at mAb concentrations of 100 ng/ml, the inhibition level observed with mAbs 926, 1337, 1338 and 1339 is very close to the inhibition level observed with the murine mAb B-E8.

Figure 13:
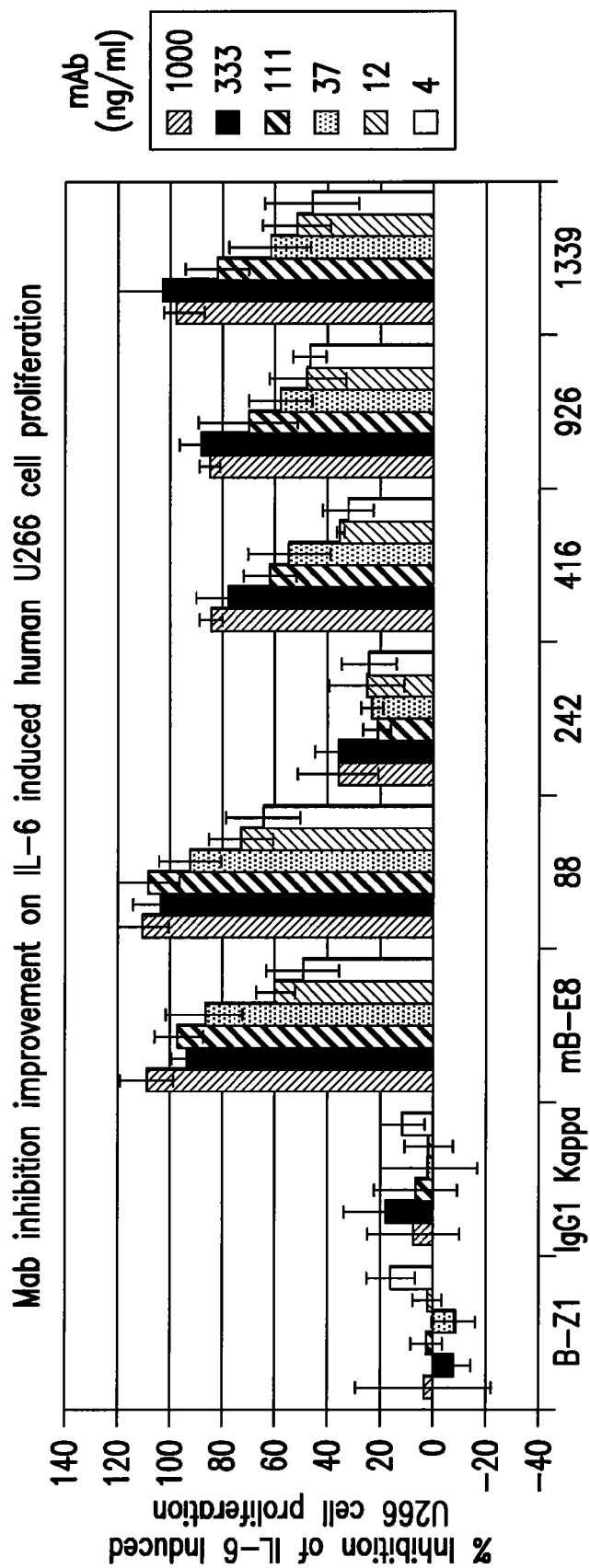
FIG. 13 shows the results of experiments in which IL-6-specific mAbs were tested for their ability to inhibit the IL-6-dependent proliferation of the human U266 myeloma cell line. For each mAb, the six columns from left to right indicate the percent inhibition of IL-6 (500 pg/ml)-induced U266 cell proliferation at mAb concentrations of 1000, 333, 111, 37, 12, and 4 ng/ml, respectively. Each column represents a mean of three experiments +/− standard deviation.

As shown in FIG. 13, mAbs 416, 926, and 1339 showed a dose-dependent inhibitory effect on IL-6-induced human myeloma cell proliferation.

Inhibition of the Interaction Between IL-6 and IL-6R

To further assess the biological activity of the human anti-IL-6 mAbs, their ability to inhibit the interaction between IL-6 and the IL-6 receptor was assessed using flow cytometry.

Flow cytometry was carried out using standard methods. First, Fc-receptor blocking on U266 cells was carried out. U266 is an IgE and IL-6 producing human plasmacytoma line. U266 cells were harvested and spun down. Cells were counted and washed twice in flow buffer (FB) and adjusted to roughly 120% of the final cell number needed for the assay, calculating 150,000 cells per well of a 96 well plate. Cells were resuspended in FB at 5×10e6 cells/ml and adjusted to 0.1 mg huIgG/ml. Cells were mixed and incubated on ice for 20-30 min. Next, 15 volumes FB was added and the cells were spun down. The supernatant was discarded and the cells were washed two more times with 20 ml FB. The cells were then resuspended to a density of 1.5×10e6 cells/ml and 100 µl was added per well to the preincubation plate. Next, recombinant human IL-6 and anti-human IL-6 mAbs were coincubated. All of the necessary dilutions of mAbs and IL-6 in FB were first prepared. Next 50 µl of mAb was preincubated with 50 µl of IL-6 (preferably at 1 nM final) for 30 minutes on ice after mixing the plate on a plate vortex for 30 s at medium power. Control wells for each mAb were included with either no IL-6 or IL-6 in the absence of antibody. Next, U266 cells were coincubated with IL-6 and anti-IL6 mAbs. The blocked and washed cells were added in 100 µl FB to the IL6/MAb mix from above. The final incubation volume was 200 µl. The cells were incubated for 30 min on ice. The wash steps between incubations were carried out as follows: Initially the incubation plate was spun at 250×g for 4 min in a centrifuge set to 4° C. The plates were carefully flipped and wiped without dislocating the pellets. Next, the cells were resuspended by vortexing the plate for 10 s at highest power. 220 µl FB was added and the plate was spun again. This wash step was repeated one more time and the vortexed cell pellets were finally resuspended in 100 µl of the respective antibody dilution. Then the cells were incubated with the mouse anti IL-6 antibody B-F6. 100 µl of the antibody [5 µg/ml in FB] was added directly to the washed cell pellets from above which were loosened up by brief vortexing and then carefully vortexed again at medium power for 15 s. The cells were incubated for 30 min on ice and washed. Next the cells were incubated with APC coupled goat anti-mouse IgG1. The loosened, washed cell pellets were resuspended in 100 µl of the labeled antibody [2.5 µg allophycocyanin/ml]. Cells were kept in the dark and vortexed and incubated on ice for 30 min. The cells were washed and resuspended in 200 to 400 µl FB. Analysis by flow cytometry was then conducted. First, propidium iodide (PI) was added using a 150-fold dilution of the PI stock. A live gate based on the exclusion of PI by looking at Fl-3 vs. FSC was set. PI was added only for the next samples of cells to avoid extended incubation of cells with PI.

Figure 6A:
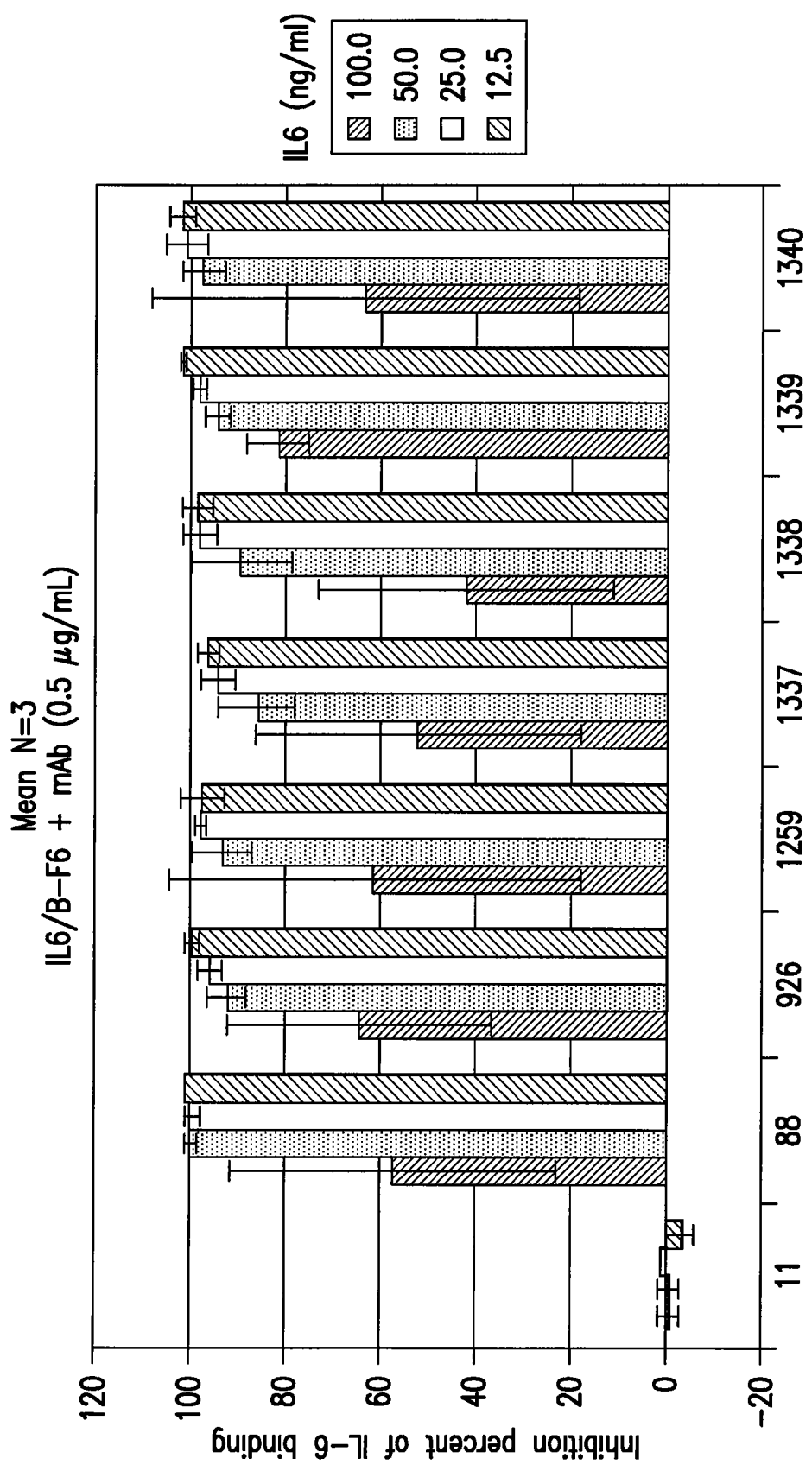
FIGS. 6A and 7A show the results of experiments in which IL-6-specific mAbs were tested for their ability to inhibit the interaction between IL-6 and the IL-6 receptor expressed on U266 cells, as analyzed by flow cytometry. Each column represents a mean of three experiments +/− standard deviation.
Figure 6B:
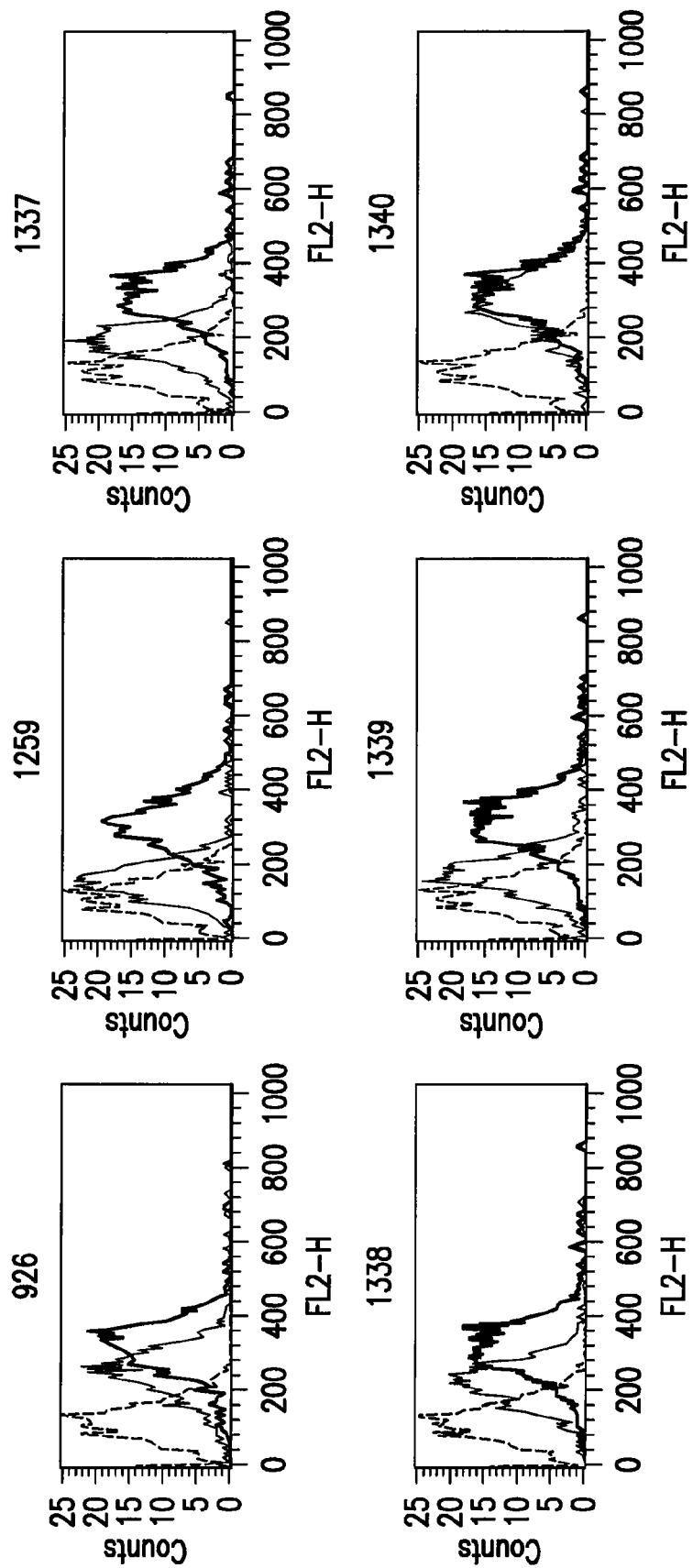
FIGS. 6B and 7B show the results of single, representative experiments at 100 ng/ml IL-6 which illustrate the inhibitory effect of various anti-IL-6 mAbs on the interaction between IL-6 and the IL-6 receptor expressed on U266 cells, as analyzed by flow cytometry. The dark solid lines represent 100 ng/ml IL-6 alone in the absence of mAb; the light solid lines represent 100 ng/ml IL-6 in the presence of mAb; and the dashed lines represent mAb alone in the absence of IL-6.
Figure 7A:
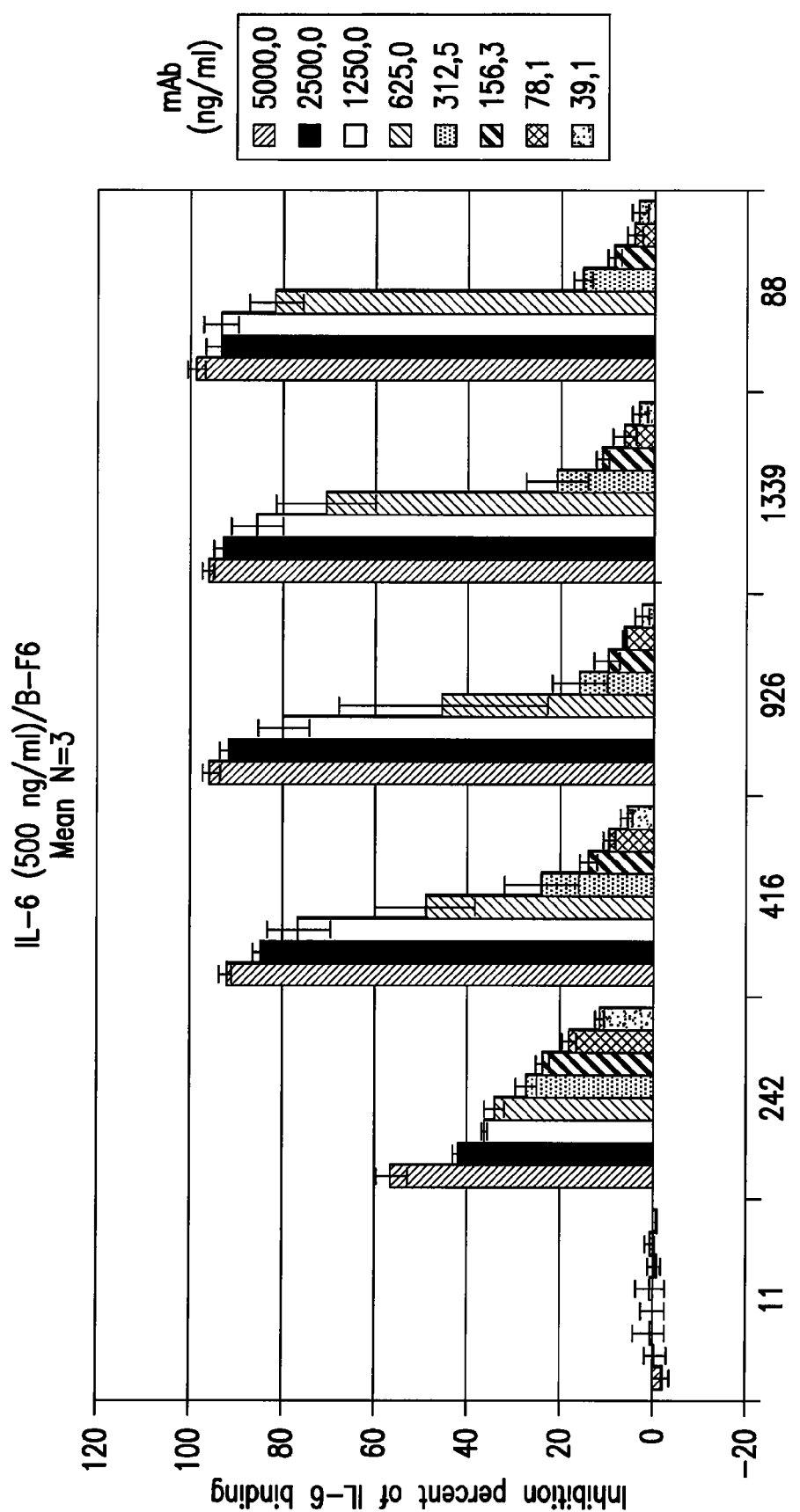
Figure 7B:
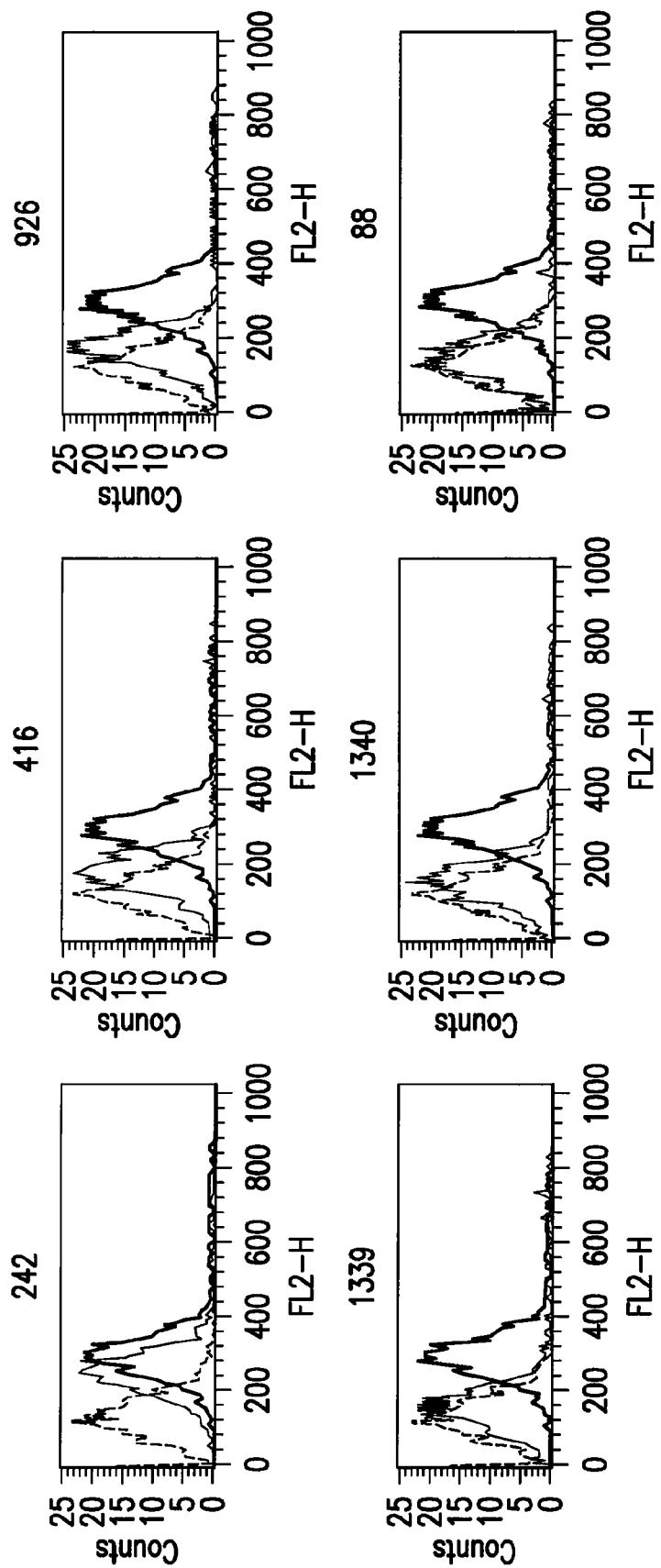

As shown in FIGS. 6A and 6B, mAbs 926, 1259, 1337, 1338, 1339 and 1340 all showed an inhibitory effect on IL-6 binding to IL-6 receptor on U266 cells under increasing concentrations of IL-6 with the antibody concentration held constant at 0.5 µg/ml. A notably high level of inhibition was observed with mAb 1339. Similarly, FIGS. 7A and 7B show an inhibitory effect of mAbs 242, 416, 926 and 1339 on IL-6 binding to IL-6 receptor on U266 cells under increasing concentrations of mAb with the IL-6 concentration held constant at 500 ng/ml.

The inhibitory effect of the mAbs was also demonstrated when biotinylated IL-6 was used (data not shown).

These results show that mAbs 242, 416, 926, 1259, 1337, 1338, 1339 and 1340 are capable of inhibiting the interaction between IL-6 and its receptor and therefore confirm the biological activity of these mAbs.

Figure 8:
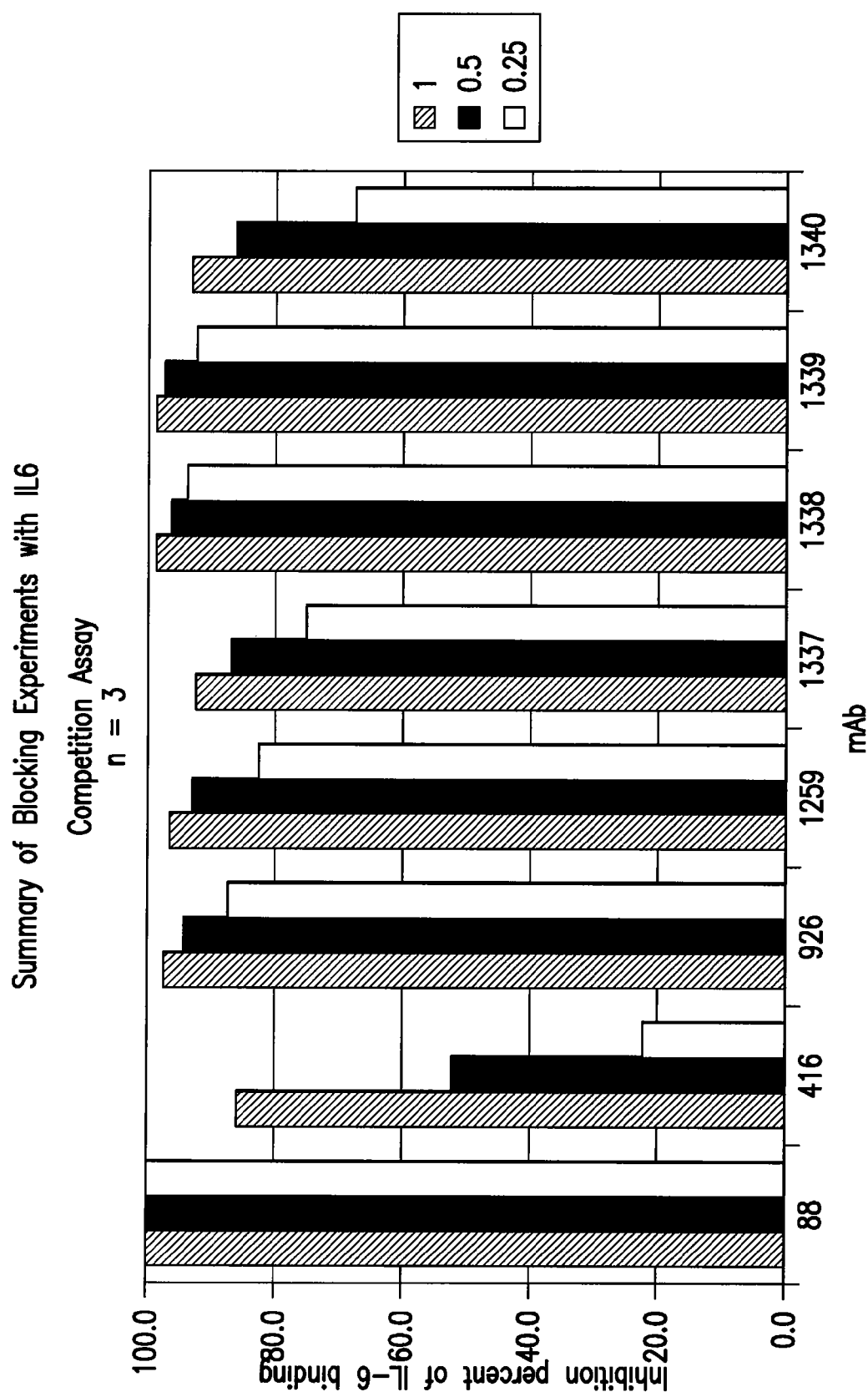
FIG. 8 is a summary chart showing the results of three separate IL-6 binding inhibition assays.

Finally, a competition assay as described in Example 2 for FIGS. 4A-4G was performed using mAbs 416, 926, 1259, 1337, 1338, 1339 and 1340, along with control mAb 88. As shown in FIG. 8, all of the mAbs tested exhibited a dose-dependent inhibitory effect on recombinant human IL-6 binding to the IL-6 receptor.

Example 6 mAb Specificity of mAbs 926 and 1339

Figure 14:
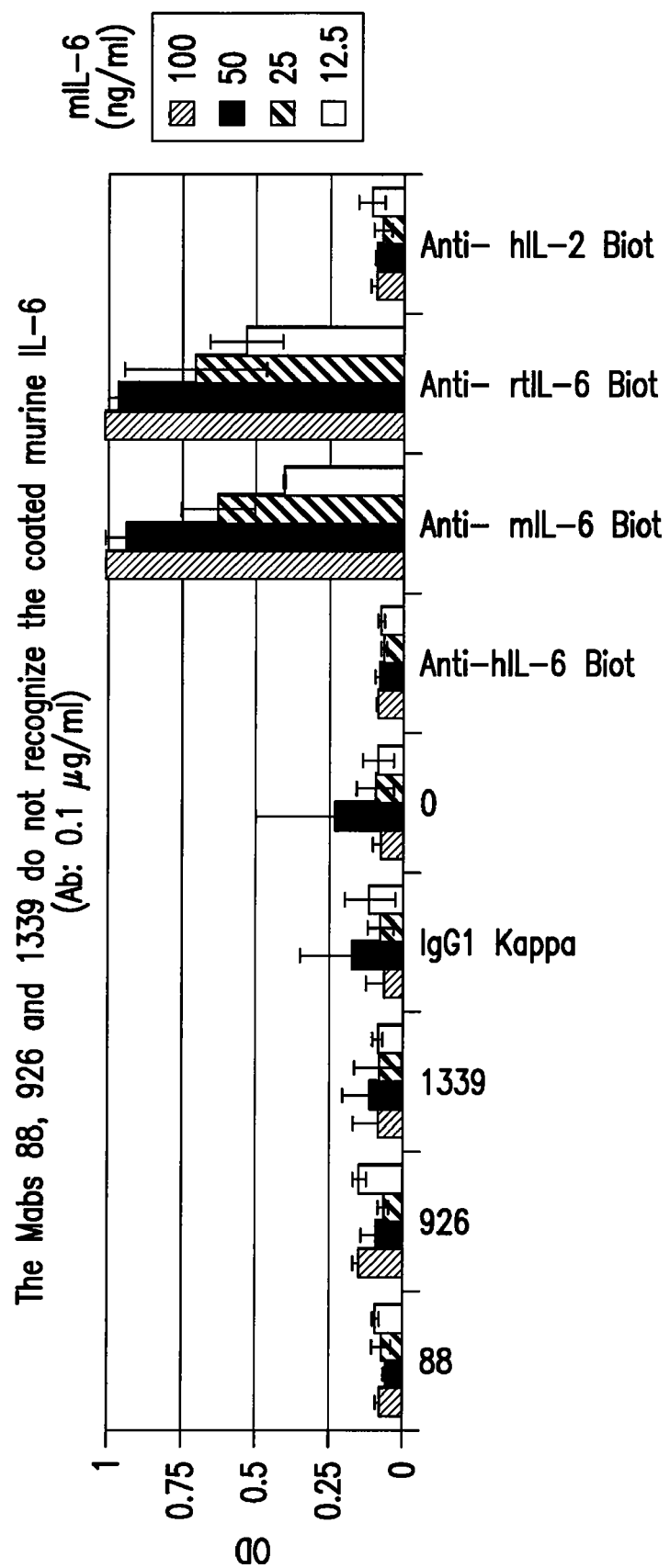
FIGS. 14 and 15 show the results of experiments in which IL-6-specific mAbs were tested for their ability to detect murine IL-6 (FIG. 14) or rat IL-6 (FIG. 15) by ELISA. Biotinylated polyclonal antibody (pAb) controls were anti-human IL-6, anti-mouse IL-6, anti-rat IL-6, and anti-human IL-2. For sample "0," no antibody was added. For each sample, the four columns from left to right indicate the optical density associated with binding to 100 ng/ml murine or rat IL-6 at antibody concentrations of 100, 50, 25, and 12.5 ng/ml, respectively. Each column represents a mean of two experiments +/− standard deviation.
Figure 15:
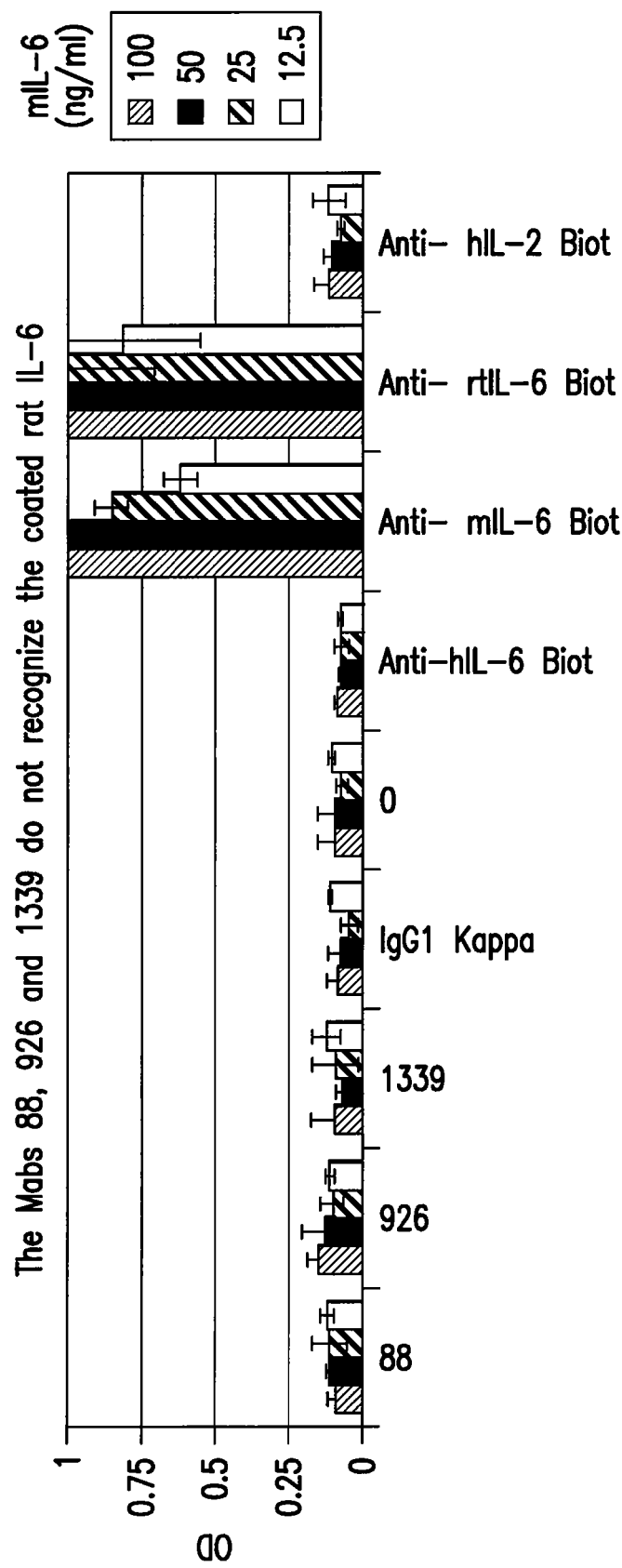

Cross-reactivity with murine and rat IL-6 was determined for mAbs 926 and 1339 by ELISA as described above. Wells were coated with 100 ng/ml murine or rat IL-6 (R&D Systems) at 100 µl/well. For experiments using human monoclonal antibodies, IgG1 Kappa (human myeloma IgG1; Sigma-Aldrich Co.) mAb was used as a control. Rabbit anti-human IgG-HRP (Dako) was added at a dilution of 1/10,000 at 100 µl/well for detection of mAbs. Polyclonal antibody (pAb) controls included biotinylated goat anti-human IL-6 (Peprotech), biotinylated goat anti-murine IL-6 (Peprotech), and biotinylated goat anti-human Il-2 (Peprotech). For pAbs, Streptavidin-HRP (Prozyme) was added for detection at 100 µl/well. Antibodies were applied at concentrations of 12.5, 25, 50, and 100 ng/ml. As shown in FIGS. 14 and 15, respectively, mAbs 926 and 1339 do not detect coated recombinant murine or rat IL-6 by ELISA.

Example 7

Detection of Natural Human and Monkey IL-6

Figure 16:
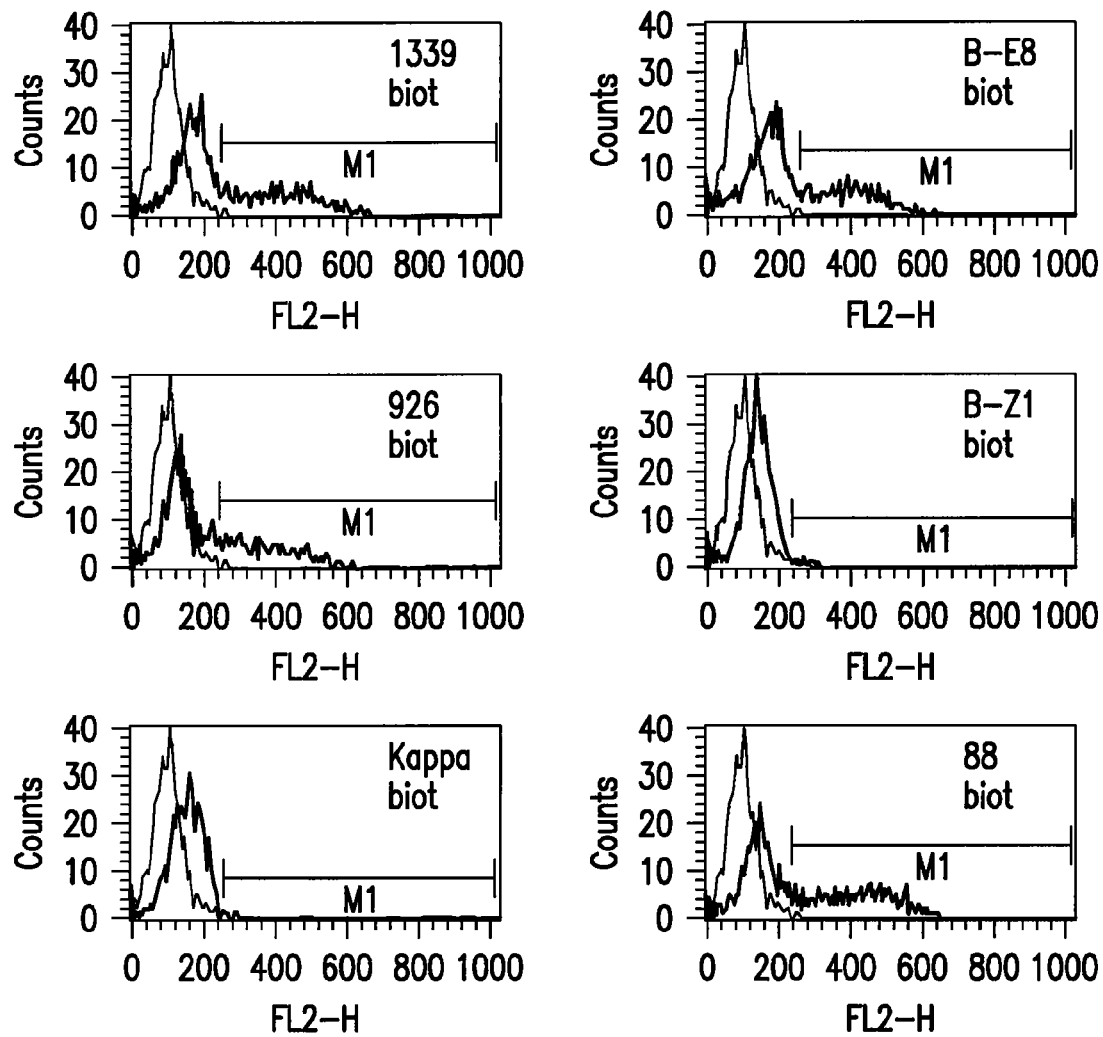
FIG. 16 shows the results of experiments in which IL-6-specific mAbs were tested for their ability to detect natural intracytoplasmic IL-6 in human monocytes from peripheral blood mononuclear cells (PBMNC) activated for 24 hours with LPS. The thicker lines represent mAb detection of IL-6 from LPS-stimulated monocytes while the thinner lines represent absence of added antibody.

The ability of mAbs 926 and 1339 to detect natural human IL-6 was analyzed in activated human monocytes. Monocytes from peripheral blood mononuclear cells were activated for 24 hours with lipopolysaccharide (LPS; 20 µg/ml; Sigma-Aldrich Co.) in order to induce intracytoplasmic expression of IL-6 (data not shown). Cells were treated with 1 µg/ml Brefeldin A (Sigma-Aldrich Co.) 6 hours before the end of LPS treatment to inhibit transport of IL-6 to the supernatant. Activated cells were analyzed by flow cytometry as previously described with 0.8 µg/ml biotinylated mAbs 88, 1339, 926, B-E8 (anti-murine-IL-6; Diaclone), B-Z1 (mouse IgG1; Diaclone), and human IgG1 Kappa (Sigma-Aldrich Co.). Three independent experiments were performed for each antibody. Representative experiments are shown in FIG. 16, showing that mAbs 926 and 1339 recognize natural intracytoplasmic IL-6.

Figure 17:
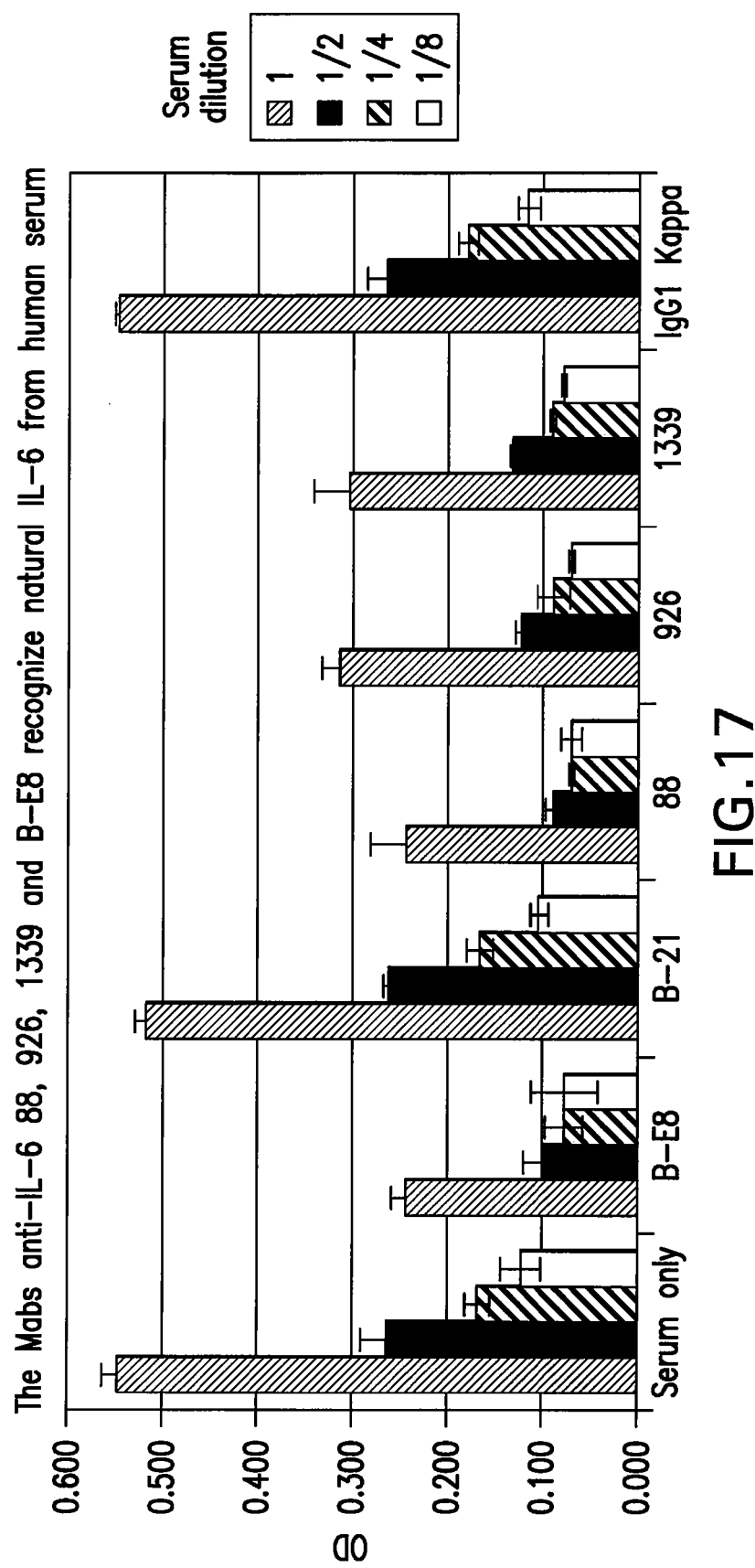
FIGS. 17 and 18 show the results of experiments in which IL-6-specific mAbs were tested for their ability to detect IL-6 from plasma. A "Serum only" sample to which no mAb was added served as a reference. Reduction in the optical density signal in the IL-6-specific antibody samples in comparison to the "Serum only" sample indicates interaction of serum IL-6 with the antibodies. Antibodies were tested at 5 µg/ml.

Additionally, the ability of mAbs 926 and 1339 to detect natural human IL-6 from human serum was determined by ELISA using the Diaclone High Sensitivity human IL-6 ELISA kit according to manufacturer protocols. Using the latter kit, the detection of human IL-6 was determined by mAb competition (5 µg/ml) with the IL-6 antibody coated on the ELISA plate wells. Addition of serum containing IL-6 (Serum AB batch 5; Blood Center, Besançon, France) in the absence of a competitor antibody results in detection of IL-6 by the ELISA kit. Addition of serum containing IL-6 in the presence of a competitor antibody results in a reduction in the ability of the ELISA kit to detect IL-6 in the serum. Control antibodies included B-E8 (anti-murine-IL-6; Diaclone), B-Z1 (mouse IgG1; Diaclone), and human IgG1 Kappa (Sigma-Aldrich Co.). As shown in FIG. 17, mAbs 926 and 1339 detect natural IL-6 from healthy donor serum.

Figure 18:
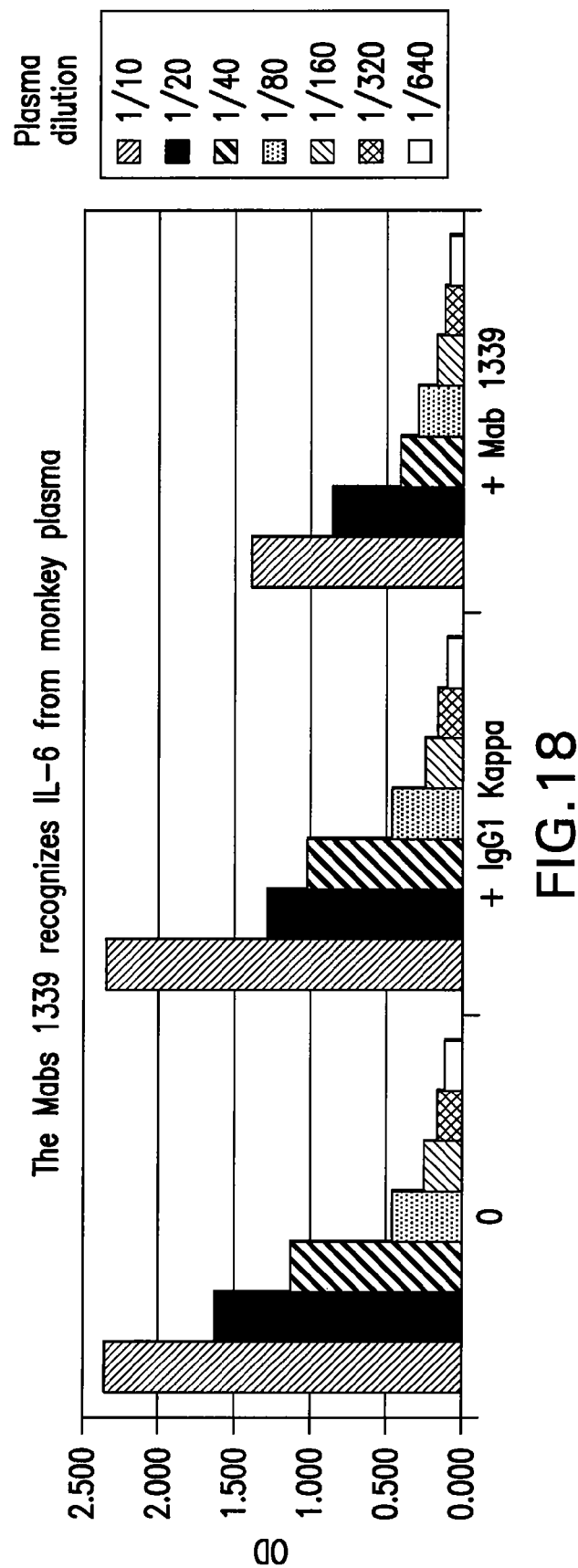

The ability of mAb 1339 to detect natural monkey IL-6 from rhesus monkey serum (BPRC, The Netherlands) was determined by ELISA using the U-Cytech Monkey IL-6 ELISA kit (U-Cytech biosciences) according to manufacturer protocols. Using the latter kit, the detection of monkey IL-6 was determined by mAb competition (5 µg/ml) with the IL-6 antibody coated on the ELISA plate wells. Addition of serum containing IL-6 in the absence of a competitor antibody results in detection of IL-6 by the ELISA kit. Addition of serum containing IL-6 in the presence of a competitor antibody results in a reduction in the ability of the ELISA kit to detect IL-6 in the serum. Monkey IgG1 Kappa served as a control antibody. As shown in FIG. 18, mAb 1339 detects natural IL-6 from monkey serum.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

The Sequence Listing written in the file named "sequence listing ascii.txt", 86,016 bytes, created on Jul. 26, 2007, on a compact disc for the U.S. Application entitled Anti-IL-6 Monoclonal Antibodies and Uses Thereof, is herein incorporated by reference.

What is claimed is:

1. An isolated monoclonal antibody comprising:
   (a) a variable heavy chain region (VH) comprising:
   (i) a VH-CDR1 comprising an amino acid sequence selected from the group consisting of: SEQ ID NO:51, SEQ ID NO:52, SEQ ID NO:53, SEQ ID NO:54, and SEQ ID NO:55;
   (ii) a VH-CDR2 comprising an amino acid sequence selected from the group consisting of: SEQ ID NO:56, SEQ ID NO:57, SEQ ID NO:58, SEQ NO:59, SEQ ID NO:60, SEQ ID NO:61, SEQ ID NO:97 and SEQ ID NO:101;
   (iii) a VH-CDR3 comprising an amino acid sequence selected from the group consisting of: SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, and SEQ ID NO:98; and
   (b) a variable light chain region (VL) comprising:
   (i) a VL-CDR1 comprising an amino acid sequence selected from the group consisting of: SEQ ID NO:74, SEQ ID NO:75, SEQ ID NO:76, SEQ ID NO:77, SEQ ID NO:78, and SEQ ID NO:79;
   (ii) a VL-CDR2 comprising an amino acid sequence selected from the group consisting of: SEQ ID NO:80, SEQ ID NO:81, SEQ ID NO:82, SEQ ID NO:83, SEQ ID NO:84, and SEQ ID NO:85;
   (iii) a VL-CDR3 comprising an amino acid sequence selected from the group consisting of: SEQ ID NO:86, SEQ ID NO:87, SEQ ID NO:88, SEQ ID NO:89, ID NO:90, SEQ ID NO:91, SEQ ID NO:92, SEQ ID NO:93, SEQ ID NO:94, SEQ ID NO:95, and SEQ ID NO:96;

wherein said antibody binds specifically to an IL-6 antigen.

2. A pharmaceutical composition comprising the isolated monoclonal antibody of claim 1 and a pharmaceutically acceptable carrier.

3. The isolated monoclonal antibody of claim 1, wherein said antibody inhibits IL-6-induced proliferation of murine B9 (ECACC) cells or human U266 myeloma cells at a level of 80% or greater inhibition.

4. The isolated monoclonal antibody of claim 1, wherein said antibody binds specifically to IL-6, inhibiting the binding of IL-6 to its receptor at a level of 80% or greater inhibition.

5. The antibody of claim 1, wherein said VH-CDR1 comprises the amino acid sequence of SEQ ID NO:54, said VH-CDR2 comprises the amino acid sequence of SEQ ID NO:101, and said VH-CDR3 comprises the amino acid sequence of SEQ ID NO:73.

6. The antibody of claim 1, wherein said VL-CDR1 comprises the amino acid sequence of SEQ ID NO:79, said VL-CDR2 comprises the amino acid sequence of SEQ ID NO:85, and said VL-CDR3 comprises the amino acid sequence of SEQ ID NO:95.

7. The antibody of claim 1, wherein said VH-CDR1 comprises the amino acid sequence of SEQ ID NO:54, said VH-CDR2 comprises the amino acid sequence of SEQ ID NO:101, said VH-CDR3 comprises the amino acid sequence of SEQ ID NO:73, said VL-CDR1 comprises the amino acid sequence of SEQ ID NO:79, said VL-CDR2 comprises the amino acid sequence of SEQ ID NO:85, and said VL-CDR3 comprises the amino acid sequence of SEQ ID NO:95.

8. The antibody of claim 1, wherein said VH comprises the amino acid sequence of SEQ ID NO:43 and said VL comprises the amino acid sequence of SEQ ID NO:36.

9. The antibody of claim 1, wherein said antibody comprises a combination of CDRS selected from the group consisting of:

(a) the VH-CDR1 of SEQ ID NO:51, the VH-CDR2 of SEQ ID NO:56, the VH-CDR3 of SEQ ID NO:62, the VL-CDR1 of SEQ ID NO:76, the VL-CDR2 of SEQ ID NO:82, and the VL-CDR3 of SEQ ID NO:88;

(b) the VH-CDR1 of SEQ ID NO:51, the VH-CDR2 of SEQ ID NO:56, the VH-CDR3 of SEQ ID NO:62, the VL-CDR1 of SEQ ID NO:77, the VL-CDR2 of SEQ ID NO:83, and the VL-CDR3 of SEQ ID NO:89;

(c) the VH-CDR1 of SEQ ID NO:51, the VH-CDR2 of SEQ ID NO:56, the VH-CDR3 of SEQ ID NO:62, the VL-CDR1 of SEQ ID NO:78, the VL-CDR2 of SEQ ID NO:84, and the VL-CDR3 of SEQ ID NO:90;

(d) the VH-CDR1 of SEQ ID NO:51, the VH-CDR2 of SEQ ID NO:56, the VH-CDR3 of SEQ ID NO:62, the VL-CDR1 of SEQ ID NO:79, the VL-CDR2 of SEQ ID NO:85, and the VL-CDR3 of SEQ ID NO:91;

(e) the VH-CDR1 of SEQ ID NO:51, the VH-CDR2 of SEQ ID NO:56, the VH-CDR3 of SEQ ID NO:98, the VL-CDR1 of SEQ ID NO:78, the VL-CDR2 of SEQ ID NO:84, and the VL-CDR3 of SEQ ID NO:90;

(f) the VH-CDR1 of SEQ ID NO:53, the VH-CDR2 of SEQ ID NO:58, the VH-CDR3 of SEQ ID NO:62, the VL-CDR1 of SEQ ID NO:75, the VL-CDR2 of SEQ ID NO:81, and the VL-CDR3 of SEQ ID NO:87;

(g) the VH-CDR1 of SEQ ID NO:53, the VH-CDR2 of SEQ ID NO:59, the VH-CDR3 of SEQ ID NO:62, the VL-CDR1 of SEQ ID NO:75, the VL-CDR2 of SEQ ID NO:81, and the VL-CDR3 of SEQ ID NO:87;

(h) the VH-CDR1 of SEQ ID NO:54, the VH-CDR2 of SEQ ID NO:60, the VH-CDR3 of SEQ ID NO:62, the VL-CDR1 of SEQ ID NO:75, the VL-CDR2 of SEQ ID NO:81, and the VL-CDR3 of SEQ ID NO:87;

(i) the VH-CDR1 of SEQ ID NO:54, the VH-CDR2 of SEQ ID NO:60, the VH-CDR3 of SEQ ID NO:62, the VL-CDR1 of SEQ ID NO:76, the VL-CDR2 of SEQ ID NO:82, and the VL-CDR3 of SEQ ID NO:88;

(j) the VH-CDR1 of SEQ ID NO:52, the VH-CDR2 of SEQ ID NO:57, the VH-CDR3 of SEQ ID NO:62, the VL-CDR1 of SEQ ID NO:74, the VL-CDR2 of SEQ ID NO:80, and the VL-CDR3 of SEQ ID NO:86;

(k) the VH-CDR1 of SEQ ID NO:52, the VH-CDR2 of SEQ ID NO:57, the VH-CDR3 of SEQ ID NO:62, the VL-CDR1 of SEQ ID NO:75, the VL-CDR2 of SEQ ID NO:81, and the VL-CDR3 of SEQ ID NO:87;

(l) the VH-CDR1 of SEQ ID NO:52, the VH-CDR2 of SEQ ID NO:57, the VH-CDR3 of SEQ ID NO:62, the VL-CDR1 of SEQ ID NO:76, the VL-CDR2 of SEQ ID NO:82, and the VL-CDR3 of SEQ ID NO:88;

(m) the VH-CDR1 of SEQ ID NO:51, the VH-CDR2 of SEQ ID NO:97, the VH-CDR3 of SEQ ID NO:62, the VL-CDR1 of SEQ ID NO:75, the VL-CDR2 of SEQ ID NO:81, and the VL-CDR3 of SEQ ID NO:87;

(n) the VH-CDR1 of SEQ ID NO:51, the VH-CDR2 of SEQ ID NO:97, the VH-CDR3 of SEQ ID NO:62, the VL-CDR1 of SEQ ID NO:76, the VL-CDR2 of SEQ ID NO:82, and the VL-CDR3 of SEQ ID NO:88;

(o) the VH-CDR1 of SEQ ID NO:54, the VH-CDR2 of SEQ ID NO:60, the VH-CDR3 of SEQ ID NO:62, the VL-CDR1 of SEQ ID NO:79, the VL-CDR2 of SEQ ID NO:85, and the VL-CDR3 of SEQ ID NO:91;

(p) the VH-CDR1 of SEQ ID NO:54, the VH-CDR2 of SEQ ID NO:60, the VH-CDR3 of SEQ ID NO:63, the VL-CDR1 of SEQ ID NO:79, the VL-CDR2 of SEQ ID NO:85, and the VL-CDR3 of SEQ ID NO:91;

(q) the VH-CDR1 of SEQ ID NO:54, the VH-CDR2 of SEQ ID NO:60, the VH-CDR3 of SEQ ID NO:64, the VL-CDR1 of SEQ ID NO:79, the VL-CDR2 of SEQ ID NO:85, and the VL-CDR3 of SEQ ID NO:91;

(r) the VH-CDR1 of SEQ ID NO:54, the VH-CDR2 of SEQ ID NO:60, the VH-CDR3 of SEQ ID NO:65, the VL-CDR1 of SEQ ID NO:79, the VL-CDR2 of SEQ ID NO:85, and the VL-CDR3 of SEQ ID NO:91;

(s) the VH-CDR1 of SEQ ID NO:54, the VH-CDR2 of SEQ ID NO:60, the VH-CDR3 of SEQ ID NO:66, the VL-CDR1 of SEQ ID NO:79, the VL-CDR2 of SEQ ID NO:85, and the VL-CDR3 of SEQ ID NO:91;

(t) the VH-CDR1 of SEQ ID NO:54, the VH-CDR2 of SEQ ID NO:60, the VH-CDR3 of SEQ ID NO:67, the VL-CDR1 of SEQ ID NO:79, the VL-CDR2 of SEQ ID NO:85, and the VL-CDR3 of SEQ ID NO:91;

(u) the VH-CDR1 of SEQ ID NO:54, the VH-CDR2 of SEQ ID NO:60, the VH-CDR3 of SEQ ID NO:68, the VL-CDR1 of SEQ ID NO:79, the VL-CDR2 of SEQ ID NO:85, and the VL-CDR3 of SEQ ID NO:91;

(v) the VH-CDR1 of SEQ ID NO:54, the VH-CDR2 of SEQ ID NO:60, the VH-CDR3 of SEQ ID NO:69, the VL-CDR1 of SEQ ID NO:79, the VL-CDR2 of SEQ ID NO:85, and the VL-CDR3 of SEQ ID NO:91;

(w) the VH-CDR1 of SEQ ID NO:54, the VH-CDR2 of SEQ ID NO:60, the VH-CDR3 of SEQ ID NO:62, the VL-CDR1 of SEQ ID NO:79, the VL-CDR2 of SEQ ID NO:85, and the VL-CDR3 of SEQ ID NO:92;

(x) the VH-CDR1 of SEQ ID NO:54, the VH-CDR2 of SEQ ID NO:60, the VH-CDR3 of SEQ ID NO:62, the VL-CDR1 of SEQ ID NO:79, the VL-CDR2 of SEQ ID NO:85, and the VL-CDR3 of SEQ ID NO:93;
(y) the VH-CDR1 of SEQ ID NO:54, the VH-CDR2 of SEQ ID NO:60, the VH-CDR3 of SEQ ID NO:62, the VL-CDR1 of SEQ ID NO:79, the VL-CDR2 of SEQ ID NO:85, and the VL-CDR3 of SEQ ID NO:96;
(z) the VH-CDR1 of SEQ ID NO:54, the VH-CDR2 of SEQ ID NO:60, the VH-CDR3 of SEQ ID NO:62, the VL-CDR1 of SEQ ID NO:79, the VL-CDR2 of SEQ ID NO:85, and the VL-CDR3 of SEQ ID NO:96;
(aa) the VH-CDR1 of SEQ ID NO:54, the VH-CDR2 of SEQ ID NO:60, the VH-CDR3 of SEQ ID NO:73, the VL-CDR1 of SEQ ID NO:79, the VL-CDR2 of SEQ ID NO:85, and the VL-CDR3 of SEQ ID NO:91;
(bb) the VH-CDR1 of SEQ ID NO:54, the VH-CDR2 of SEQ ID NO:60, the VH-CDR3 of SEQ ID NO:73, the VL-CDR1 of SEQ ID NO:79, the VL-CDR2 of SEQ ID NO:85, and the VL-CDR3 of SEQ ID NO:93;
(cc) the VH-CDR1 of SEQ ID NO:54, the VH-CDR2 of SEQ ID NO:60, the VH-CDR3 of SEQ ID NO:73, the VL-CDR1 of SEQ ID NO:79, the VL-CDR2 of SEQ ID NO:85, and the VL-CDR3 of SEQ ID NO:92;
(dd) the VH-CDR1 of SEQ ID NO:54, the VH-CDR2 of SEQ ID NO:101, the VH-CDR3 of SEQ ID NO:62, the VL-CDR1 of SEQ ID NO:79, the VL-CDR2 of SEQ ID NO:85, and the VL-CDR3 of SEQ ID NO:91;
(ee) the VH-CDR1 of SEQ ID NO:54, the VH-CDR2 of SEQ ID NO:101, the VH-CDR3 of SEQ ID NO:73, the VL-CDR1 of SEQ ID NO:79, the VL-CDR2 of SEQ ID NO:85, and the VL-CDR3 of SEQ ID NO:91;
(ff) the VH-CDR1 of SEQ ID NO:54, the VH-CDR2 of SEQ ID NO:101, the VH-CDR3 of SEQ ID NO:73, the VL-CDR1 of SEQ ID NO:79, the VL-CDR2 of SEQ ID NO:85, and the VL-CDR3 of SEQ ID NO:93;
(gg) the VH-CDR1 of SEQ ID NO:54, the VH-CDR2 of SEQ ID NO:101, the VH-CDR3 of SEQ ID NO:73, the VL-CDR1 of SEQ ID NO:79, the VL-CDR2 of SEQ ID NO:85, and the VL-CDR3 of SEQ ID NO:92; and
(hh) the VH-CDR1 of SEQ ID NO:54, the VH-CDR2 of SEQ ID NO:101, the VH-CDR3 of SEQ ID NO:73, the VL-CDR1 of SEQ ID NO:79, the VL-CDR2 of SEQ ID NO:85, and the VL-CDR3 of SEQ ID NO:96.

\* \* \* \* \*

```
                          SEQUENCE LISTING

<160> NUMBER OF SEQ ID NOS: 101

<210> SEQ ID NO 1
<211> LENGTH: 107
<212> TYPE: PRT
<213> ORGANISM: Homo sapiens

<400> SEQUENCE: 1

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Ser Val Ser Gln Ser Ile Ser Gly Ile Pro Ser Arg Phe Ser Gly
```

-continued

```
            50                  55                  60
Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys
            100                 105

<210> SEQ ID NO 2
<211> LENGTH: 106
<212> TYPE: PRT
<213> ORGANISM: Homo sapiens

<400> SEQUENCE: 2

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Thr Ile Asp Ser Ser
             20                  25                  30

Tyr Leu Ala Trp Tyr Gln Gln Lys Pro Gly Gln Ala Pro Arg Leu Leu
         35                  40                  45

Val Tyr Gly Ala Ser Ser Arg Ala Thr Gly Ile Pro Asp Arg Phe Ser
 50                  55                  60

Asp Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Lys Ser Pro
                 85                  90                  95

Ile Thr Phe Gly Gln Gly Thr Lys Leu Glu
            100                 105

<210> SEQ ID NO 3
<211> LENGTH: 105
<212> TYPE: PRT
<213> ORGANISM: Homo sapiens

<400> SEQUENCE: 3

Asp Val Val Met Thr Gln Ser Pro Ser Ser Val Ser Ala Ser Val Gly
  1               5                  10                  15

Asp Arg Val Thr Ile Thr Cys Arg Ala Ser Gln Asp Ile Asp Asn Phe
             20                  25                  30

Leu Ala Trp Tyr Gln Gln Lys Pro Gly Lys Ala Pro Asn Leu Leu Ile
         35                  40                  45

Tyr Lys Val Ser Ser Leu Arg Ser Gly Val Pro Ser Arg Phe Ser Gly
 50                  55                  60

Ser Arg Ser Gly Thr Asp Phe Thr Leu Thr Ile Thr Ser Leu Gln Pro
 65                  70                  75                  80

Glu Asp Phe Ala Thr Tyr Phe Cys Gln Gln Thr Arg Arg Phe Pro Leu
                 85                  90                  95

Thr Phe Gly Pro Gly Thr Lys Leu Glu
            100                 105

<210> SEQ ID NO 4
<211> LENGTH: 105
<212> TYPE: PRT
<213> ORGANISM: Homo sapiens

<400> SEQUENCE: 4

Asp Ile Val Met Thr Gln Ser Pro Ser Ser Leu Ser Ala Ser Val Gly
  1               5                  10                  15
```

```
Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Thr Tyr Tyr Cys Gln Gln Ala Asn Ser Phe Pro Leu
                85                  90                  95

Thr Phe Gly Gly Gly Thr Lys Leu Glu
            100                 105
```

<210> SEQ ID NO 5
<211> LENGTH: 106
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Leu Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Tyr Arg Pro Leu Thr
                85                  90                  95

Phe Gly Gly Gly Thr Lys Leu Glu Ile Lys
            100                 105
```

<210> SEQ ID NO 6
<211> LENGTH: 105
<212> TYPE: PRT
<213> ORGANISM: Homo sapiens

<400> SEQUENCE: 6

```
Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Ser Ile Ser Ile Tyr
            20                  25                  30

Leu Asn Trp Tyr Gln Gln Lys Pro Gly Lys Ala Pro Asp Leu Leu Ile
        35                  40                  45

Tyr Ala Thr Ser Thr Leu Gln Ser Gly Val Pro Ser Arg Phe Ser Gly
    50                  55                  60

Arg Gly Ser Gly Thr His Phe Thr Leu Thr Ile Asp Ser Leu Gln Pro
65                  70                  75                  80

Glu Asp Phe Ala Thr Tyr Tyr Cys Gln Gln Thr Tyr Arg Asn Leu Phe
                85                  90                  95

Thr Phe Gly Gln Gly Thr Lys Leu Glu
            100                 105
```

<210> SEQ ID NO 7
<211> LENGTH: 107
<212> TYPE: PRT

<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Ser Val Thr Val Thr Cys Arg Ala Ser Gln Lys Met Arg Thr Tyr
            20                  25                  30

Leu His Trp Tyr Gln Gln Lys Pro Gly Lys Ala Pro Lys Leu Leu Ile
        35                  40                  45

Tyr Asp Val Ser Phe Leu Gln Asn Gly Val Pro Ser Arg Phe Ser Gly
    50                  55                  60

Arg Ala Ser Gly Thr Glu Phe Thr Leu Thr Ile Ser Asp Leu Gln Pro
65                  70                  75                  80

Glu Asp Phe Ala Thr Tyr Tyr Cys Gln Gln Ser Tyr Asp Thr Pro Leu
                85                  90                  95

Thr Phe Gly Gln Gly Thr Lys Leu Glu Ile Lys
            100                 105

<210> SEQ ID NO 8
<211> LENGTH: 107
<212> TYPE: PRT
<213> ORGANISM: Homo sapiens

<400> SEQUENCE: 8

Asp Val Val Met Thr Gln Ser Pro Ser Val Ser Ala Ser Val Gly
1               5                   10                  15

Asp Arg Val Thr Ile Thr Cys Arg Ala Ser Gln Val Ile Asp Ser Trp
            20                  25                  30

Leu His Trp Tyr Gln Arg Glu Pro Gly Lys Ala Pro Lys Ile Leu Ile
        35                  40                  45

Tyr Ala Ala Thr Thr Leu Gln Arg Gly Val Pro Ser Arg Phe Ser Gly
    50                  55                  60

Ser Gly Phe Gly Thr Glu Phe Thr Leu Thr Ile Ser Gly Leu Gln Pro
65                  70                  75                  80

Glu Asp Phe Ala Thr Tyr Phe Cys Gln Gln Gly Tyr Ser Phe Pro Ile
                85                  90                  95

Thr Phe Gly Gln Gly Thr Arg Leu Glu Ile Lys
            100                 105

<210> SEQ ID NO 9
<211> LENGTH: 107
<212> TYPE: PRT
<213> ORGANISM: Homo sapiens

<400> SEQUENCE: 9

Asp Val Val Met Thr Gln Ser Pro Ser Ser Leu Ser Ala Ser Val Gly
1               5                   10                  15

Gly Arg Val Thr Ile Thr Cys Arg Ala Ser Gln Thr Ile Gly Asp Tyr
            20                  25                  30

Leu Asn Trp Tyr Gln Gln Lys Pro Gly Lys Ala Pro Arg Leu Leu Ile
        35                  40                  45

Tyr Ser Ala Ser Ile Val Gln Ser Gly Val Pro Ser Arg Phe Ser Ala
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Ser Tyr Ser Phe Pro Leu
                85                  90                  95

```
Thr Phe Gly Gly Gly Thr Lys Leu Glu Ile Lys
            100                 105
```

<210> SEQ ID NO 10
<211> LENGTH: 107
<212> TYPE: PRT
<213> ORGANISM: Homo sapiens

<400> SEQUENCE: 10

```
Glu Ile Val Leu Thr Gln Ser Pro Ser Ser Leu Ser Ala Ser Ala Gly
1               5                   10                  15

Asp Thr Val Thr Ile Ala Cys Arg Ala Ser Gln Gly Ile Arg Thr Ala
            20                  25                  30

Leu Ala Trp Tyr Gln Gln Lys Pro Gly Arg Asn Pro Lys Leu Leu Ile
        35                  40                  45

Ser Glu Ala Tyr Arg Leu Gln Ser Gly Val Ser Pro Lys Phe Ser Gly
    50                  55                  60

Ser Gly Phe Gly Thr Asp Phe Thr Leu Thr Ile Asn Ser Leu Gln Pro
65                  70                  75                  80

Glu Asp Phe Ala Thr Tyr Tyr Cys Gln Gln Phe Asn Asp Phe Pro Leu
                85                  90                  95

Thr Phe Gly Gly Gly Thr Lys Leu Glu Ile Lys
            100                 105
```

<210> SEQ ID NO 11
<211> LENGTH: 107
<212> TYPE: PRT
<213> ORGANISM: Homo sapiens

<400> SEQUENCE: 11

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Ser Lys Ala Ser Ser Leu Glu Tyr Gly Val Pro Ser Arg Phe Ser Gly
    50                  55                  60

Ser Gly Ser Gly Thr Glu Phe Ala Leu Thr Ile Ser Asn Val Gln Pro
65                  70                  75                  80

Glu Asp Phe Ala Thr Tyr Tyr Cys Gln Gln Ser Phe Ala Val Pro Leu
                85                  90                  95

Thr Phe Gly Gly Gly Thr Lys Leu Glu Ile Lys
            100                 105
```

<210> SEQ ID NO 12
<211> LENGTH: 105
<212> TYPE: PRT
<213> ORGANISM: Homo sapiens

<400> SEQUENCE: 12

```
Asp Ile Gln Met Thr Gln Ser Pro Ser Ser Leu Ser Ala Phe Val Gly
1               5                   10                  15

Asp Gly Val Thr Met Thr Cys Trp Ala Ser Gln Ser Ile Asn Asp Tyr
            20                  25                  30

Leu Asn Trp Tyr His Gln Arg Pro Gly Glu Ala Pro Glu Leu Leu Val
        35                  40                  45

Phe Ala Ala Ser Asn Leu Gln Ile Gly Val Pro Ser Arg Phe Arg Gly
    50                  55                  60
```

Ser Gly Ser Glu Thr Tyr Phe Thr Leu Thr Ile Asn Ser Leu Gln Pro
65                  70                  75                  80

Glu Asp Ser Gly Thr Tyr Phe Cys Gln Gln Thr Ser Ser Phe Pro Leu
                85                  90                  95

Thr Phe Gly Gly Gly Thr Lys Leu Glu
            100                 105

<210> SEQ ID NO 13
<211> LENGTH: 105
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Thr Ile Ser Asp Phe
            20                  25                  30

Leu Asn Trp Tyr Gln Gln Lys Pro Gly Lys Ala Pro Lys Leu Leu Ile
        35                  40                  45

His Ala Ser Ser Asn Leu Gln Ser Gly Val Pro Ser Arg Phe Ser Gly
    50                  55                  60

Ser Gly Ser Gly Thr Asp Phe Thr Leu Thr Ile Ser Asp Leu Gln Pro
65                  70                  75                  80

Glu Asp Phe Ala Thr Tyr Ser Cys Gln Gln Thr Tyr Ser Thr Leu Gly
                85                  90                  95

Thr Phe Gly Gln Gly Thr Arg Leu Glu
            100                 105

<210> SEQ ID NO 14
<211> LENGTH: 107
<212> TYPE: PRT
<213> ORGANISM: Homo sapiens

<400> SEQUENCE: 14

Asp Val Val Met Thr Gln Ser Pro Ser Ser Leu Ser Ala Ser Val Gly
1               5                   10                  15

Gly Arg Val Thr Ile Thr Cys Arg Ala Ser Gln Thr Ile Gly Asp Tyr
            20                  25                  30

Leu Asn Trp Tyr Gln Gln Arg Pro Gly Lys Ala Pro Arg Leu Leu Ile
        35                  40                  45

Tyr Ser Ala Ser Ile Val Gln Ser Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Phe Ala Thr Tyr Ser Cys Gln Gln Ser Tyr Ser Phe Pro Leu
                85                  90                  95

Thr Phe Gly Gly Gly Thr Lys Leu Glu Ile Lys
            100                 105

<210> SEQ ID NO 15
<211> LENGTH: 104
<212> TYPE: PRT
<213> ORGANISM: Homo sapiens

<400> SEQUENCE: 15

Asp Ile Val Met Thr Gln Ser Pro Ser Ser Leu Ser Ala Ser Val Gly
1               5                   10                  15

Asp Arg Val Thr Ile Thr Cys Arg Ala Ser Arg Asn Ile Asn Thr Tyr

```
                    20                  25                  30
Leu Asn Trp Tyr Gln Gln Lys Pro Gly Lys Ala Pro Lys Leu Leu Val
         35                  40                  45

His Ser Ala Ser Thr Leu Gln Ser Gly Ala Pro Ser Arg Phe Ser Gly
 50                  55                  60

Ser Gly Tyr Gly Thr Glu Phe Thr Leu Ile Ile Ser Ser Leu Gln Pro
 65                  70                  75                  80

Asp Asp Phe Ala Thr Tyr Tyr Cys Gln Gln Gly Tyr Asn Thr Leu Thr
                 85                  90                  95

Phe Gly Pro Gly Thr Lys Leu Glu
                100
```

<210> SEQ ID NO 16
<211> LENGTH: 107
<212> TYPE: PRT
<213> ORGANISM: Homo sapiens

<400> SEQUENCE: 16

```
Glu Ile Val Leu Thr Gln Ser Pro Ser Ser Leu Ser Ala Ser Val Gly
  1               5                  10                  15

Asp Arg Val Thr Ile Ser Cys Arg Ala Ser Gln Asn Ile Ile Asp Tyr
                 20                  25                  30

Leu Asn Trp Tyr Gln His Lys Pro Gly Lys Val Pro Thr Leu Leu Ile
         35                  40                  45

Ser Gly Thr Ser Thr Leu Gln Ser Gly Val Pro Ser Arg Phe Ser Gly
 50                  55                  60

Ser Gly Phe Gly Thr Asp Phe Thr Leu Thr Ile Ser Ser Val Gln Pro
 65                  70                  75                  80

Glu Asp Val Ala Thr Tyr Tyr Cys Gln Gln Gly His Gly Thr Pro Leu
                 85                  90                  95

Ser Phe Gly Gly Gly Thr Lys Leu Glu Ile Lys
                100                 105
```

<210> SEQ ID NO 17
<211> LENGTH: 107
<212> TYPE: PRT
<213> ORGANISM: Homo sapiens

<400> SEQUENCE: 17

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Met Ser Asp Tyr
                 20                  25                  30

Leu Asn Trp Tyr Gln Gln Lys Pro Gly Lys Ala Pro Lys Leu Leu Ile
         35                  40                  45

Tyr Ser Ala Ser Gly Leu Gln Ser Gly Val Pro Ser Arg Phe Ser Gly
 50                  55                  60

Ser Gly Ser Gly Thr Asp Phe Thr Leu Thr Ile Ile Asn Leu Gln Pro
 65                  70                  75                  80

Glu Asp Val Ala Ala Tyr Tyr Cys Gln Gln Ser Phe Ser Phe Pro Leu
                 85                  90                  95

Thr Phe Gly Pro Gly Thr Lys Leu Glu Ile Lys
                100                 105
```

<210> SEQ ID NO 18
<211> LENGTH: 106
<212> TYPE: PRT
<213> ORGANISM: Homo sapiens

```
<400> SEQUENCE: 18

Asp Ile Gln Met Thr Gln Ser Pro Ser Ser Leu Ser Ala Phe Val Gly
1               5                   10                  15

Asp Gly Val Thr Met Thr Cys Trp Ala Ser Gln Ser Ile Asn Asp Tyr
            20                  25                  30

Leu Asn Trp Tyr His Gln Arg Pro Gly Glu Ala Pro Glu Leu Leu Val
        35                  40                  45

Phe Ala Ala Ser Asn Leu Gln Ile Gly Val Pro Ser Arg Phe Arg Gly
    50                  55                  60

Ser Gly Ser Glu Thr Tyr Phe Thr Leu Thr Ile Asn Ser Leu Gln Pro
65                  70                  75                  80

Glu Asp Ser Gly Thr Tyr Phe Cys Gln Asn Gly His Ser Phe Pro Leu
                85                  90                  95

Thr Phe Gly Gly Gly Thr Lys Leu Glu Ile
                100                 105

<210> SEQ ID NO 19
<211> LENGTH: 119
<212> TYPE: PRT
<213> ORGANISM: Homo sapiens

<400> SEQUENCE: 19

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Ser
            20                  25                  30

Gly Met Cys Val Ser Trp Ile Arg Gln Pro Pro Gly Lys Ala Leu Glu
        35                  40                  45

Trp Leu Ala Leu Ile Tyr Trp Asp Asp Asp Lys Arg Tyr Asn Pro Ser
    50                  55                  60

Leu Arg Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Tyr Asp Asp Tyr Leu Tyr Tyr Ala Leu Asp Tyr Trp
                100                 105                 110

Gly Gln Gly Thr Leu Val Thr
            115

<210> SEQ ID NO 20
<211> LENGTH: 119
<212> TYPE: PRT
<213> ORGANISM: Homo sapiens

<400> SEQUENCE: 20

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Ser
            20                  25                  30

Gly Met Cys Val Ser Trp Ile Arg Gln Pro Pro Gly Lys Ala Leu Glu
        35                  40                  45

Trp Leu Ala Leu Ile Tyr Trp Asp Asp Asp Lys Arg Tyr Asn Pro Ser
    50                  55                  60

Leu Arg Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
```

```
                    85                  90                  95
Cys Ala Arg Ser His Asp Asp Tyr Leu Tyr Tyr Ala Leu Asp Tyr Trp
            100                 105                 110

Gly Gln Gly Thr Leu Val Thr
        115

<210> SEQ ID NO 21
<211> LENGTH: 119
<212> TYPE: PRT
<213> ORGANISM: Homo sapiens

<400> SEQUENCE: 21

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Arg Thr Ser
            20                  25                  30

Gly Val Ser Val Gly Trp Phe Arg Gln Pro Pro Gly Lys Ala Leu Glu
        35                  40                  45

Trp Leu Ala Leu Val Tyr Trp Asp Asp Asp Arg Tyr Asn Pro Ser
    50                  55                  60

Leu Lys Asn Arg Leu Thr Ile Thr Arg Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Tyr Asp Asp Tyr Leu Tyr Tyr Ala Leu Asp Tyr Trp
            100                 105                 110

Gly Gln Gly Thr Leu Val Thr
        115

<210> SEQ ID NO 22
<211> LENGTH: 119
<212> TYPE: PRT
<213> ORGANISM: Homo sapiens

<400> SEQUENCE: 22

Gln Val Thr Leu Lys Glu Ser Gly Pro Thr Leu Val Lys Pro Thr Gln
1               5                   10                  15

Thr Leu Thr Leu Thr Cys Ile Phe Ser Gly Phe Ser Phe Lys Thr Ser
            20                  25                  30

Gly Val Ser Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Asn Arg Leu Thr Ile Thr Arg Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Tyr Asp Asp Tyr Leu Tyr Tyr Ala Leu Asp Tyr Trp
            100                 105                 110

Gly Gln Gly Thr Leu Val Thr
        115

<210> SEQ ID NO 23
<211> LENGTH: 119
<212> TYPE: PRT
<213> ORGANISM: Homo sapiens

<400> SEQUENCE: 23
```

```
Gln Val Thr Leu Lys Glu Ser Gly Pro Thr Leu Val Lys Pro Thr Gln
  1               5                  10                  15

Thr Leu Thr Leu Thr Cys Ser Phe Ser Gly Phe Ser Leu Ser Thr Ser
             20                  25                  30

Gly Val Gly Val Gly Trp Val Arg Gln Pro Pro Gly Lys Ala Leu Glu
         35                  40                  45

Trp Leu Ala Phe Ile Phe Trp Asp Asp Lys Tyr Tyr Ser Pro Ser
     50                  55                  60

Leu Glu Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
             85                  90                  95

Cys Ala Arg Ser Tyr Asp Asp Tyr Leu Tyr Tyr Ala Leu Asp Tyr Trp
            100                 105                 110

Gly Gln Gly Thr Leu Val Thr
            115

<210> SEQ ID NO 24
<211> LENGTH: 122
<212> TYPE: PRT
<213> ORGANISM: Homo sapiens

<400> SEQUENCE: 24

Gln Val Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Val Ala Val Gly Trp Ile Arg Gln Pro Pro Gly Lys Ala Leu Glu
         35                  40                  45

Trp Leu Ala Leu Ile Phe Trp Asp Asp Lys His Tyr Ser Pro Ser
     50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
             85                  90                  95

Cys Ala Arg Ser Tyr Asp Asp Tyr Leu Tyr Tyr Ala Leu Asp Tyr Trp
            100                 105                 110

Gly Gln Gly Thr Leu Val Thr Val Ser Ser
            115                 120

<210> SEQ ID NO 25
<211> LENGTH: 119
<212> TYPE: PRT
<213> ORGANISM: Homo sapiens

<400> SEQUENCE: 25

Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Cys Val Ser Trp Ile Arg Gln Pro Pro Gly Lys Ala Leu Glu
         35                  40                  45

Trp Leu Leu Ile Tyr Trp Asp Asp Lys Arg Tyr Ser Pro Ser
     50                  55                  60

Leu Glu Thr Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
```

```
                            85                  90                  95
Cys Ala Arg Ser Tyr Asp Asp Tyr Leu Tyr Tyr Ala Leu Asp Tyr Trp
                100                 105                 110

Gly Gln Gly Thr Leu Val Thr
            115

<210> SEQ ID NO 26
<211> LENGTH: 119
<212> TYPE: PRT
<213> ORGANISM: Artificial Sequence
<220> FEATURE:
<223> OTHER INFORMATION: Human H1511 variant

<400> SEQUENCE: 26

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Val Gly Val Gly Trp Val Arg Gln Pro Pro Gly Lys Ala Leu Glu
        35                  40                  45

Trp Leu Ala Phe Ile Phe Trp Asp Asp Asp Lys Tyr Tyr Ser Pro Ser
    50                  55                  60

Leu Glu Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Phe Tyr Asp Asp Tyr Leu Tyr Tyr Ala Leu Asp Tyr Trp
                100                 105                 110

Gly Gln Gly Thr Leu Val Thr
            115

<210> SEQ ID NO 27
<211> LENGTH: 119
<212> TYPE: PRT
<213> ORGANISM: Artificial Sequence
<220> FEATURE:
<223> OTHER INFORMATION: Human H1420 variant

<400> SEQUENCE: 27

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Val Gly Val Gly Trp Val Arg Gln Pro Pro Gly Lys Ala Leu Glu
        35                  40                  45

Trp Leu Ala Phe Ile Phe Trp Asp Asp Asp Lys Tyr Tyr Ser Pro Ser
    50                  55                  60

Leu Glu Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Ala Asp Asp Tyr Leu Tyr Tyr Ala Leu Asp Tyr Trp
                100                 105                 110

Gly Gln Gly Thr Leu Val Thr
            115

<210> SEQ ID NO 28
<211> LENGTH: 119
<212> TYPE: PRT
```

```
<213> ORGANISM: Artificial Sequence
<220> FEATURE:
<223> OTHER INFORMATION: Human H1432 variant

<400> SEQUENCE: 28

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Val Gly Val Gly Trp Val Arg Gln Pro Pro Gly Lys Ala Leu Glu
        35                  40                  45

Trp Leu Ala Phe Ile Phe Trp Asp Asp Asp Lys Tyr Tyr Ser Pro Ser
    50                  55                  60

Leu Glu Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Gly Asp Asp Tyr Leu Tyr Tyr Ala Leu Asp Tyr Trp
            100                 105                 110

Gly Gln Gly Thr Leu Val Thr
        115

<210> SEQ ID NO 29
<211> LENGTH: 119
<212> TYPE: PRT
<213> ORGANISM: Artificial Sequence
<220> FEATURE:
<223> OTHER INFORMATION: Human H1515 variant

<400> SEQUENCE: 29

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Val Gly Val Gly Trp Val Arg Gln Pro Pro Gly Lys Ala Leu Glu
        35                  40                  45

Trp Leu Ala Phe Ile Phe Trp Asp Asp Asp Lys Tyr Tyr Ser Pro Ser
    50                  55                  60

Leu Glu Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Tyr Asp Asp Tyr Leu Met Tyr Ala Leu Asp Tyr Trp
            100                 105                 110

Gly Gln Gly Thr Leu Val Thr
        115

<210> SEQ ID NO 30
<211> LENGTH: 119
<212> TYPE: PRT
<213> ORGANISM: Artificial Sequence
<220> FEATURE:
<223> OTHER INFORMATION: Human H1362 variant

<400> SEQUENCE: 30

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30
```

```
Gly Val Gly Val Gly Trp Val Arg Gln Pro Pro Gly Lys Ala Leu Glu
            35                  40                  45

Trp Leu Ala Phe Ile Phe Trp Asp Asp Lys Tyr Tyr Ser Pro Ser
 50                  55                  60

Leu Glu Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ser Tyr Asp Asp Tyr Leu Tyr Tyr Ser Leu Asp Tyr Trp
                100                 105                 110

Gly Gln Gly Thr Leu Val Thr
            115
```

<210> SEQ ID NO 31
<211> LENGTH: 119
<212> TYPE: PRT
<213> ORGANISM: Artificial Sequence
<220> FEATURE:
<223> OTHER INFORMATION: Human H1437 variant

<400> SEQUENCE: 31

```
Gln Val Thr Leu Lys Glu Ser Gly Pro Thr Leu Val Lys Pro Thr Gln
 1               5                  10                  15

Thr Leu Thr Leu Thr Cys Ser Phe Ser Gly Phe Ser Leu Ser Thr Ser
                20                  25                  30

Gly Val Gly Val Gly Trp Val Arg Gln Pro Pro Gly Lys Ala Leu Glu
            35                  40                  45

Trp Leu Ala Phe Ile Phe Trp Asp Asp Lys Tyr Tyr Ser Pro Ser
 50                  55                  60

Leu Glu Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ser Tyr Asp Asp Tyr Leu Tyr Tyr Ala Phe Asp Tyr Trp
                100                 105                 110

Gly Gln Gly Thr Leu Val Thr
            115
```

<210> SEQ ID NO 32
<211> LENGTH: 119
<212> TYPE: PRT
<213> ORGANISM: Artificial Sequence
<220> FEATURE:
<223> OTHER INFORMATION: Human H1461 variant

<400> SEQUENCE: 32

```
Gln Val Thr Leu Lys Glu Ser Gly Pro Thr Leu Val Lys Pro Thr Gln
 1               5                  10                  15

Thr Leu Thr Leu Thr Cys Ser Phe Ser Gly Phe Ser Leu Ser Thr Ser
                20                  25                  30

Gly Val Gly Val Gly Trp Val Arg Gln Pro Pro Gly Lys Ala Leu Glu
            35                  40                  45

Trp Leu Ala Phe Ile Phe Trp Asp Asp Lys Tyr Tyr Ser Pro Ser
 50                  55                  60

Leu Glu Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95
```

```
Cys Ala Arg Ser Tyr Asp Asp Tyr Leu Tyr Tyr Ala Leu Asp Thr Trp
            100                 105                 110
Gly Gln Gly Thr Leu Val Thr
        115
```

<210> SEQ ID NO 33
<211> LENGTH: 106
<212> TYPE: PRT
<213> ORGANISM: Artificial Sequence
<220> FEATURE:
<223> OTHER INFORMATION: Human L314 variant

<400> SEQUENCE: 33

```
Asp Ile Gln Met Thr Gln Ser Pro Ser Ser Leu Ser Ala Phe Val Gly
1               5                   10                  15
Asp Gly Val Thr Met Thr Cys Trp Ala Ser Gln Ser Ile Asn Asp Tyr
            20                  25                  30
Leu Asn Trp Tyr His Gln Arg Pro Gly Glu Ala Pro Glu Leu Leu Val
        35                  40                  45
Phe Ala Ala Ser Asn Leu Gln Ile Gly Val Pro Ser Arg Phe Arg Gly
    50                  55                  60
Ser Gly Ser Glu Thr Tyr Phe Thr Leu Thr Ile Asn Ser Leu Gln Pro
65                  70                  75                  80
Glu Asp Ser Gly Thr Tyr Phe Cys Gln Ser Gly His Ser Phe Pro Leu
                85                  90                  95
Thr Phe Gly Gly Gly Thr Lys Leu Glu Ile
            100                 105
```

<210> SEQ ID NO 34
<211> LENGTH: 106
<212> TYPE: PRT
<213> ORGANISM: Artificial Sequence
<220> FEATURE:
<223> OTHER INFORMATION: Human L305 variant

<400> SEQUENCE: 34

```
Asp Ile Gln Met Thr Gln Ser Pro Ser Ser Leu Ser Ala Phe Val Gly
1               5                   10                  15
Asp Gly Val Thr Met Thr Cys Trp Ala Ser Gln Ser Ile Asn Asp Tyr
            20                  25                  30
Leu Asn Trp Tyr His Gln Arg Pro Gly Glu Ala Pro Glu Leu Leu Val
        35                  40                  45
Phe Ala Ala Ser Asn Leu Gln Ile Gly Val Pro Ser Arg Phe Arg Gly
    50                  55                  60
Ser Gly Ser Glu Thr Tyr Phe Thr Leu Thr Ile Asn Ser Leu Gln Pro
65                  70                  75                  80
Glu Asp Ser Gly Thr Tyr Phe Cys Gln His Gly His Ser Phe Pro Leu
                85                  90                  95
Thr Phe Gly Gly Gly Thr Lys Leu Glu Ile
            100                 105
```

<210> SEQ ID NO 35
<211> LENGTH: 106
<212> TYPE: PRT
<213> ORGANISM: Artificial Sequence
<220> FEATURE:
<223> OTHER INFORMATION: Human L303 variant

<400> SEQUENCE: 35

```
Asp Ile Gln Met Thr Gln Ser Pro Ser Ser Leu Ser Ala Phe Val Gly
1               5                   10                  15
```

```
Asp Gly Val Thr Met Thr Cys Trp Ala Ser Gln Ser Ile Asn Asp Tyr
            20                  25                  30

Leu Asn Trp Tyr His Gln Arg Pro Gly Glu Ala Pro Glu Leu Leu Val
        35                  40                  45

Phe Ala Ala Ser Asn Leu Gln Ile Gly Val Pro Ser Arg Phe Arg Gly
    50                  55                  60

Ser Gly Ser Glu Thr Tyr Phe Thr Leu Thr Ile Asn Ser Leu Gln Pro
65                  70                  75                  80

Glu Asp Ser Gly Thr Tyr Phe Cys Gln Leu Gly His Ser Phe Pro Leu
                85                  90                  95

Thr Phe Gly Gly Gly Thr Lys Leu Glu Ile
            100                 105

<210> SEQ ID NO 36
<211> LENGTH: 106
<212> TYPE: PRT
<213> ORGANISM: Artificial Sequence
<220> FEATURE:
<223> OTHER INFORMATION: Human L298 variant

<400> SEQUENCE: 36

Asp Ile Gln Met Thr Gln Ser Pro Ser Ser Leu Ser Ala Phe Val Gly
1               5                   10                  15

Asp Gly Val Thr Met Thr Cys Trp Ala Ser Gln Ser Ile Asn Asp Tyr
            20                  25                  30

Leu Asn Trp Tyr His Gln Arg Pro Gly Glu Ala Pro Glu Leu Leu Val
        35                  40                  45

Phe Ala Ala Ser Asn Leu Gln Ile Gly Val Pro Ser Arg Phe Arg Gly
    50                  55                  60

Ser Gly Ser Glu Thr Tyr Phe Thr Leu Thr Ile Asn Ser Leu Gln Pro
65                  70                  75                  80

Glu Asp Ser Gly Thr Tyr Phe Cys Gln Asn Ala His Ser Phe Pro Leu
                85                  90                  95

Thr Phe Gly Gly Gly Thr Lys Leu Glu Ile
            100                 105

<210> SEQ ID NO 37
<211> LENGTH: 106
<212> TYPE: PRT
<213> ORGANISM: Artificial Sequence
<220> FEATURE:
<223> OTHER INFORMATION: Human L321 variant

<400> SEQUENCE: 37

Asp Ile Gln Met Thr Gln Ser Pro Ser Ser Leu Ser Ala Phe Val Gly
1               5                   10                  15

Asp Gly Val Thr Met Thr Cys Trp Ala Ser Gln Ser Ile Asn Asp Tyr
            20                  25                  30

Leu Asn Trp Tyr His Gln Arg Pro Gly Glu Ala Pro Glu Leu Leu Val
        35                  40                  45

Phe Ala Ala Ser Asn Leu Gln Ile Gly Val Pro Ser Arg Phe Arg Gly
    50                  55                  60

Ser Gly Ser Glu Thr Tyr Phe Thr Leu Thr Ile Asn Ser Leu Gln Pro
65                  70                  75                  80

Glu Asp Ser Gly Thr Tyr Phe Cys Gln Asn Gly Trp Ser Phe Pro Leu
                85                  90                  95

Thr Phe Gly Gly Gly Thr Lys Leu Glu Ile
            100                 105
```

<210> SEQ ID NO 38
<211> LENGTH: 119
<212> TYPE: PRT
<213> ORGANISM: Artificial Sequence
<220> FEATURE:
<223> OTHER INFORMATION: Human H1519 variant

<400> SEQUENCE: 38

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Val Gly Val Gly Trp Val Arg Gln Pro Pro Gly Lys Ala Leu Glu
        35                  40                  45

Trp Leu Ala Phe Ile Phe Trp Asp Asp Asp Lys Tyr Tyr Ser Pro Ser
    50                  55                  60

Leu Glu Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Ala Asp Asp Tyr Leu Tyr Tyr Ser Leu Asp Tyr Trp
            100                 105                 110

Gly Gln Gly Thr Leu Val Thr
        115

<210> SEQ ID NO 39
<211> LENGTH: 119
<212> TYPE: PRT
<213> ORGANISM: Artificial Sequence
<220> FEATURE:
<223> OTHER INFORMATION: Human H1520 variant

<400> SEQUENCE: 39

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Val Gly Val Gly Trp Val Arg Gln Pro Pro Gly Lys Ala Leu Glu
        35                  40                  45

Trp Leu Ala Phe Ile Phe Trp Asp Asp Asp Lys Tyr Tyr Ser Pro Ser
    50                  55                  60

Leu Glu Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Ala Asp Asp Tyr Leu Tyr Tyr Ala Phe Asp Tyr Trp
            100                 105                 110

Gly Gln Gly Thr Leu Val Thr
        115

<210> SEQ ID NO 40
<211> LENGTH: 119
<212> TYPE: PRT
<213> ORGANISM: Artificial Sequence
<220> FEATURE:
<223> OTHER INFORMATION: Human H1521 variant

<400> SEQUENCE: 40

Gln Val Thr Leu Lys Glu Ser Gly Pro Thr Leu Val Lys Pro Thr Gln

```
            1               5                  10                 15
Thr Leu Thr Leu Thr Cys Ser Phe Ser Gly Phe Ser Leu Ser Thr Ser
                    20                  25                 30

Gly Val Gly Val Gly Trp Val Arg Gln Pro Pro Gly Lys Ala Leu Glu
            35                  40                 45

Trp Leu Ala Phe Ile Phe Trp Asp Asp Asp Lys Tyr Tyr Ser Pro Ser
 50                  55                 60

Leu Glu Ser Arg Leu Thr Ile Thr Lys Asp Thr Ser Lys Asn Gln Val
 65                  70                 75                  80

Val Leu Thr Met Thr Asn Met Asp Pro Val Asp Thr Ala Thr Tyr Tyr
                    85                  90                 95

Cys Ala Arg Ser Ala Asp Asp Tyr Leu Tyr Tyr Ser Phe Asp Tyr Trp
                100                 105                110

Gly Gln Gly Thr Leu Val Thr
            115

<210> SEQ ID NO 41
<211> LENGTH: 119
<212> TYPE: PRT
<213> ORGANISM: Artificial Sequence
<220> FEATURE:
<223> OTHER INFORMATION: Human H1522 variant

<400> SEQUENCE: 41

Gln Val Thr Leu Lys Glu Ser Gly Pro Thr Leu Val Lys Pro Thr Gln
 1               5                  10                 15

Thr Leu Thr Leu Thr Cys Ser Phe Ser Gly Phe Ser Leu Ser Thr Ser
                    20                  25                 30

Gly Val Gly Val Gly Trp Val Arg Gln Pro Pro Gly Lys Ala Leu Glu
            35                  40                 45

Trp Leu Ala Phe Ile Phe Trp Asp Asp Asp Lys Tyr Tyr Ser Pro Ser
 50                  55                 60

Leu Glu Ser Arg Leu Thr Ile Thr Lys Asp Thr Ser Lys Asn Gln Val
 65                  70                 75                  80

Val Leu Thr Met Thr Asn Met Asp Pro Val Asp Thr Ala Thr Tyr Tyr
                    85                  90                 95

Cys Ala Arg Ser Ala Asp Asp Tyr Leu Tyr Tyr Ser Phe Asp Thr Trp
                100                 105                110

Gly Gln Gly Thr Leu Val Thr
            115

<210> SEQ ID NO 42
<211> LENGTH: 119
<212> TYPE: PRT
<213> ORGANISM: Artificial Sequence
<220> FEATURE:
<223> OTHER INFORMATION: Human H1553 variant

<400> SEQUENCE: 42

Gln Val Thr Leu Lys Glu Ser Gly Pro Thr Leu Val Lys Pro Thr Gln
 1               5                  10                 15

Thr Leu Thr Leu Thr Cys Ser Phe Ser Gly Phe Ser Leu Ser Thr Ser
                    20                  25                 30

Gly Val Gly Val Gly Trp Val Arg Gln Pro Pro Gly Lys Ala Leu Glu
            35                  40                 45

Trp Leu Ala Phe Ile Trp Trp Asp Asp Asp Lys Tyr Tyr Ser Pro Ser
 50                  55                 60

Leu Glu Ser Arg Leu Thr Ile Thr Lys Asp Thr Ser Lys Asn Gln Val
```

```
                65                  70                  75                  80
Val Leu Thr Met Thr Asn Met Asp Pro Val Asp Thr Ala Thr Tyr Tyr
                        85                  90                  95

Cys Ala Arg Ser Tyr Asp Asp Tyr Leu Tyr Tyr Ala Leu Asp Tyr Trp
                        100                 105                 110

Gly Gln Gly Thr Leu Val Thr
            115

<210> SEQ ID NO 43
<211> LENGTH: 119
<212> TYPE: PRT
<213> ORGANISM: Artificial Sequence
<220> FEATURE:
<223> OTHER INFORMATION: Human H1579 variant

<400> SEQUENCE: 43

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
                20                  25                  30

Gly Val Gly Val Gly Trp Val Arg Gln Pro Pro Gly Lys Ala Leu Glu
            35                  40                  45

Trp Leu Ala Phe Ile Trp Trp Asp Asp Asp Lys Tyr Tyr Ser Pro Ser
        50                  55                  60

Leu Glu Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                        85                  90                  95

Cys Ala Arg Ser Ala Asp Asp Tyr Leu Tyr Tyr Ser Phe Asp Thr Trp
                        100                 105                 110

Gly Gln Gly Thr Leu Val Thr
            115

<210> SEQ ID NO 44
<211> LENGTH: 490
<212> TYPE: DNA
<213> ORGANISM: Artificial Sequence
<220> FEATURE:
<223> OTHER INFORMATION: Murine mAb B-E8 heavy chain

<400> SEQUENCE: 44
gtcgacccac gcgtccggac atggacaggc ttacttcttc attcctgctg ctgattgtcc      60
ctgcatatgt cttgtcccaa gttactctaa aagagtctgg ccctgggata ttgaagccct     120
cacagaccct cagtctgact tgttctttct ctgggttttc actgagcact tctggtatgg     180
gtgtaggctg gattcgtcag ccttcaggga agggtctgga gtggctggca cacatttggt     240
gggatgatga taagtactat aacccatccc tgaagagcca gctcacaatc tccaaggata     300
cctccagaaa ccaggtattc ctcaagatca ccagtgtgga cactgcagat actgccactt     360
actactgtgc tcgatcctat gatgactatc tttactatgc tttggactac tggggtcaag     420
gaacctcagt caccgtctcc tcagccaaaa cgacaccccc atctgtctat ccactggccc     480
ctggatctgc                                                            490

<210> SEQ ID NO 45
<211> LENGTH: 470
<212> TYPE: DNA
<213> ORGANISM: Artificial Sequence
<220> FEATURE:
<223> OTHER INFORMATION: Murine mAb B-E8 light chain
```

<400> SEQUENCE: 45

```
gtcgacccac gcgtccggaa aatttgaaga tggtgtccac ttctcagctc cttggacttt      60
tgcttttctg gacttcagcc tccagatgtg acattgtgat gactcagtct ccagccaccc     120
tgtctgtgac tccaggagat agagtctctc tttcctgcag ggccagccag agtattagcg     180
actacttaca ctggtatcaa caaaaatcac atgagtctcc aaggcttctc atcaaatctg     240
tttcccaatc catctctggg atcccctcca ggttcagtgg cagtggatca gggtcagatt     300
tcactctcag tatcaacagt gtggaacctg aagatgttgg agtgtattac tgtcaaaatg     360
gtcacagctt tccgctcacg ttcggtgctg ggaccaagct ggagctgaaa cgggctgatg     420
ctgcaccaac tgtatccatc ttcccaccat catgcgagat tcgaacatct                470
```

<210> SEQ ID NO 46
<211> LENGTH: 471
<212> TYPE: PRT
<213> ORGANISM: Artificial Sequence
<220> FEATURE:
<223> OTHER INFORMATION: Human mAb 926 heavy chain

<400> SEQUENCE: 46

```
Met Gly Trp Ser Cys Ile Ile Leu Phe Leu Val Ala Thr Ala Thr Gly
1               5                   10                  15
Ala His Ser Gln Val Thr Leu Lys Glu Ser Gly Pro Thr Leu Val Lys
            20                  25                  30
Pro Thr Gln Thr Leu Thr Leu Thr Cys Ser Phe Ser Gly Phe Ser Leu
        35                  40                  45
Ser Thr Ser Gly Val Gly Val Gly Trp Val Arg Gln Pro Pro Gly Lys
    50                  55                  60
Ala Leu Glu Trp Leu Ala Phe Ile Phe Trp Asp Asp Lys Tyr Tyr
65                  70                  75                  80
Ser Pro Ser Leu Glu Ser Arg Leu Thr Ile Thr Lys Asp Thr Ser Lys
                85                  90                  95
Asn Gln Val Val Leu Thr Met Thr Asn Met Asp Pro Val Asp Thr Ala
            100                 105                 110
Thr Tyr Tyr Cys Ala Arg Ser Ala Asp Asp Tyr Leu Tyr Tyr Ala Leu
        115                 120                 125
Asp Tyr Trp Gly Gln Gly Thr Leu Val Thr Val Ser Ser Ala Ser Thr
    130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
```

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly Lys
465                 470

<210> SEQ ID NO 47
<211> LENGTH: 233
<212> TYPE: PRT
<213> ORGANISM: Artificial Sequence
<220> FEATURE:
<223> OTHER INFORMATION: Human mAb 926 light chain

<400> SEQUENCE: 47

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Phe Val Gly Asp Gly Val Thr Met Thr Cys Trp Ala Ser Gln Ser Ile
        35                  40                  45

Asn Asp Tyr Leu Asn Trp Tyr His Gln Arg Pro Gly Glu Ala Pro Glu
    50                  55                  60

Leu Leu Val Phe Ala Ala Ser Asn Leu Gln Ile Gly Val Pro Ser Arg
65                  70                  75                  80

Phe Arg Gly Ser Gly Ser Glu Thr Tyr Phe Thr Leu Thr Ile Asn Ser
                85                  90                  95

Leu Gln Pro Glu Asp Ser Gly Thr Tyr Phe Cys Gln Asn Gly His Ser
            100                 105                 110

Phe Pro Leu Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly

```
                         165                 170                 175
Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 48
<211> LENGTH: 471
<212> TYPE: PRT
<213> ORGANISM: Artificial Sequence
<220> FEATURE:
<223> OTHER INFORMATION: Human mAb 1339 heavy chain

<400> SEQUENCE: 48

Met Gly Trp Ser Cys Ile Ile Leu Phe Leu Val Ala Thr Ala Thr Gly
1               5                   10                  15

Ala His Ser Gln Val Thr Leu Lys Glu Ser Gly Pro Thr Leu Val Lys
            20                  25                  30

Pro Thr Gln Thr Leu Thr Leu Thr Cys Ser Phe Ser Gly Phe Ser Leu
        35                  40                  45

Ser Thr Ser Gly Val Gly Val Gly Trp Val Arg Gln Pro Pro Gly Lys
    50                  55                  60

Ala Leu Glu Trp Leu Ala Phe Ile Trp Trp Asp Asp Lys Tyr Tyr
65                  70                  75                  80

Ser Pro Ser Leu Glu Ser Arg Leu Thr Ile Thr Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Ser Ala Asp Tyr Leu Tyr Tyr Ser Phe
        115                 120                 125

Asp Thr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300
```

```
Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 49
<211> LENGTH: 233
<212> TYPE: PRT
<213> ORGANISM: Artificial Sequence
<220> FEATURE:
<223> OTHER INFORMATION: Human mAb 1339 light chain

<400> SEQUENCE: 49

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Phe Val Gly Asp Gly Val Thr Met Thr Cys Trp Ala Ser Gln Ser Ile
        35                  40                  45

Asn Asp Tyr Leu Asn Trp Tyr His Gln Arg Pro Gly Glu Ala Pro Glu
50                  55                  60

Leu Leu Val Phe Ala Ala Ser Asn Leu Gln Ile Gly Val Pro Ser Arg
65                  70                  75                  80

Phe Arg Gly Ser Gly Ser Glu Thr Tyr Phe Thr Leu Thr Ile Asn Ser
            85                  90                  95

Leu Gln Pro Glu Asp Ser Gly Thr Tyr Phe Cys Gln Asn Ala His Ser
            100                 105                 110

Phe Pro Leu Thr Phe Gly Gly Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190
```

```
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225                 230

<210> SEQ ID NO 50
<211> LENGTH: 12076
<212> TYPE: DNA
<213> ORGANISM: Artificial Sequence
<220> FEATURE:
<223> OTHER INFORMATION: Human mAb 1339 double gene vector

<400> SEQUENCE: 50
gctttctcat agctcacgct gtaggtatct cagttcggtg taggtcgttc gctccaagct     60
gggctgtgtg cacgaacccc ccgttcagcc cgaccgctgc gccttatccg gtaactatcg    120
tcttgagtcc aacccggtaa gacacgactt atcgccactg gcagcagcca ctggtaacag    180
gattagcaga gcgaggtatg taggcggtgc tacagagttc ttgaagtggt ggcctaacta    240
cggctacact agaagaacag tatttggtat ctgcgctctg ctgaagccag ttaccttcgg    300
aaaaagagtt ggtagctctt gatccggcaa acaaaccacc gctggtagcg tggttttttt    360
tgtttgcaag cagcagatta cgcgcagaaa aaaggatct caagaagatc ctttgatctt    420
ttctacgggg tctgacgctc agtggaacga aaactcacgt taagggattt tggtcatgag    480
attatcaaaa aggatcttca cctagatcct tttaaattaa aaatgaagtt ttaaatcaat    540
ctaaagtata tatgagtaaa cttggtctga cagttaccaa tgcttaatca gtgaggcacc    600
tatctcagcg atctgtctat ttcgttcatc catagttgcc tgactccccg tcgtgtagat    660
aactacgata cgggagggct taccatctgg ccccagtgct gcaatgatac cgcgagaccc    720
acgctcaccg gctccagatt tatcagcaat aaaccagcca gccggaaggg ccgagcgcag    780
aagtggtcct gcaactttat ccgcctccat ccagtctatt aattgttgcc gggaagctag    840
agtaagtagt tcgccagtta atagtttgcg caacgttgtt gccattgcta caggcatcgt    900
ggtgtcacgc tcgtcgtttg gtatggcttc attcagctcc ggttcccaac gatcaaggcg    960
agttacatga tcccccatgt tgtgcaaaaa agcggttagc tccttcggtc ctccgatcgt   1020
tgtcagaagt aagttggccg cagtgttatc actcatggtt atggcagcac tgcataattc   1080
tcttactgtc atgccatccg taagatgctt ttctgtgact ggtgagtact caaccaagtc   1140
attctgagaa tagtgtatgc ggcgaccgag ttgctcttgc ccggcgtcaa cacgggataa   1200
taccgcgcca catagcagaa ctttaaaagt gctcatcatt ggaaaacgtt cttcggggcg   1260
aaaactctca aggatcttac cgctgttgag atccagttcg atgtaaccca ctcgtgcacc   1320
caactgatct tcagcatctt ttactttcac cagcgtttct gggtgagcaa aaacaggaag   1380
gcaaaatgcc gcaaaaaagg gaataagggc gacacggaaa tgttgaatac tcatactctt   1440 ccttttt caa tattattgaa gcatttatca gggttattgt ctcatgagcg gatacatatt   1500
tgaatgtatt tagaaaaata aacaaatagg ggttccgcgc acatttcccc gaaaagtgcc   1560
acctgacgtc taagaaacca ttattatcat gacattaacc tataaaaata ggcgtatcac   1620
gaggccctga tggctctttg cggcacccat cgttcgtaat gttccgtggc accgaggaca   1680
accctcaaga gaaatgtaa tcacactggc tcaccttcgg gtgggccttt ctgcgtttat   1740
aaggagacac tttatgttta agaaggttgg taaattcctt gcggctttgg cagccaagct   1800
agatccggct gtggaatgtg tgtcagttag ggtgtggaaa gtccccaggc tccccagcag   1860
```

```
gcagaagtat gcaaagcatg catctcaatt agtcagcaac caggtgtgga aagtccccag   1920
gctccccagc aggcagaagt atgcaaagca tgcatctcaa ttagtcagca accatagtcc   1980 cgccctaac tccgcccatc ccgcccctaa ctccgcccag ttccgcccat tctccgcccc    2040
atggctgact aattttttt atttatgcag aggccgaggc cgcctcggcc tctgagctat    2100
tccagaagta gtgaggaggc ttttttggag gcctaggctt ttgcaaaaag ctagcttggg   2160
gccaccgctc agagcacctt ccaccatggc cacctcagca agttcccact tgaacaaaaa   2220
catcaagcaa atgtacttgt gcctgcccca gggtgagaaa gtccaagcca tgtatatctg   2280
ggttgatggt actggagaag gactgcgctg caaaacccgc accctggact gtgagcccaa   2340
gtgtgtagaa gagttacctg agtggaattt tgatggctct agtacctttc agtctgaggg   2400
ctccaacagt gacatgtatc tcagcccgt tgccatgttt cgggacccct tccgcagaga    2460
tcccaacaag ctggtgttct gtgaagtttt caagtacaac cggaagcctg cagagaccaa   2520
tttaaggcac tcgtgtaaac ggataatgga catggtgagc aaccagcacc cctggtttgg   2580
aatggaacag gagtatactc tgatgggaac agatgggcac ccttttggtt ggccttccaa   2640
tggctttcct gggccccaag gtccgtatta ctgtggtgtg ggcgcagaca aagcctatgg   2700
cagggatatc gtggaggctc actaccgcgc ctgcttgtat gctggggtca agattacagg   2760
aacaaatgct gaggtcatgc ctgcccagtg ggaactccaa ataggaccct gtgaaggaat   2820
ccgcatggga gatcatctct gggtggcccg tttcatcttg catcgagtat gtgaagactt   2880 tgggtaata gcaaccttg accccaagcc cattcctggg aactggaatg gtgcaggctg     2940
ccataccaac tttagcacca aggccatgcg ggaggagaat ggtctgaagc acatcgagga   3000
ggccatcgag aaactaagca agcggcaccg gtaccacatt cgagcctacg atcccaaggg   3060
gggcctggac aatgcccgtg gtctgactgg gttccacgaa acgtccaaca tcaacgactt   3120
ttctgctggt gtcgccaatc gcagtgccag catccgcatt ccccgactg tcggccagga    3180 gaagaaaggt tactttgaag accgcggccc ctctgccaat tgtgacccct ttgcagtgac   3240
agaagccatc gtccgcacat gccttctcaa tgagactggc gacgagccct tccaatacaa   3300
aaactaatta gactttgagt gatcttgagc cttttcctagt tcatcccacc ccgccccaga   3360
gagatctttg tgaaggaacc ttacttctgt ggtgtgacat aattggacaa actacctaca   3420
gagatttaaa gctctaaggt aaatataaaa ttttttaagtg tataatgtgt taaactactg   3480
attctaattg tttgtgtatt ttagattcca acctatggaa ctgatgaatg ggagcagtgg   3540
tggaatgcct ttaatgagga aaacctgttt tgctcagaag aaatgccatc tagtgatgat   3600
gaggctactg ctgactctca acattctact cctccaaaaa agaagagaaa ggtagaagac   3660
cccaaggact ttccttcaga attgctaagt tttttgagtc atgctgtgtt tagtaataga   3720
actcttgctt gctttgctat ttacaccaca aggaaaaag ctgcactgct atacaagaaa    3780
attatggaaa aatattctgt aacctttata agtaggcata acagttataa tcataacata   3840
ctgttttttc ttactccaca caggcataga gtgtctgcta ttaataacta tgctcaaaaa   3900
ttgtgtacct ttagcttttt aatttgtaaa ggggttaata aggaatattt gatgtatagt   3960
gccttgacta gagatcataa tcagccatac cacatttgta gaggttttac ttgctttaaa   4020
aaacctccca cacctccccc tgaacctgaa acataaaatg aatgcaattg ttgttgttaa   4080
cttgtttatt gcagcttata atggttacaa ataaagcaat agcatcacaa atttcacaaa   4140
taaagcattt ttttcactgc attctagttg tggtttgtcc aaactcatca atgtatctta   4200
tcatgtctgg atctctagct tcgtgtcaag gacggtgact gcagtgaata ataaaatgtg   4260
```

```
tgtttgtccg aaatacgcgt tttgagattt ctgtcgccga ctaaattcat gtcgcgcgat    4320
agtggtgttt atcgccgata gagatggcga tattggaaaa atcgatattt gaaaatatgg    4380
catattgaaa atgtcgccga tgtgagtttc tgtgtaactg atatcgccat ttttccaaaa    4440 gtgattttg ggcatacgcg atatctggcg atagcgctta tatcgtttac gggggatggc     4500
gatagacgac tttggtgact tgggcgattc tgtgtgtcgc aaatatcgca gtttcgatat    4560
aggtgacaga cgatatgagg ctatatcgcc gatagaggcg acatcaagct ggcacatggc    4620
caatgcatat cgatctatac attgaatcaa tattggccat tagccatatt attcattggt    4680
tatatagcat aaatcaatat tggctattgg ccattgcata cgttgtatcc atatcataat    4740
atgtacattt atattggctc atgtccaaca ttaccgccat gttgacattg attattgact    4800
agttattaat agtaatcaat tacggggtca ttagttcata gcccatatat ggagttccgc    4860
gttacataac ttacggtaaa tggcccgcct ggctgaccgc ccaacgaccc ccgcccattg    4920
acgtcaataa tgacgtatgt tcccatagta acgccaatag ggactttcca ttgacgtcaa    4980
tgggtggagt atttacggta aactgcccac ttggcagtac atcaagtgta tcatatgcca    5040
agtacgcccc ctattgacgt caatgacggt aaatggcccg cctggcatta tgcccagtac    5100
atgaccttat gggactttcc tacttggcag tacatctacg tattagtcat cgctattacc    5160
atggtgatgc ggttttggca gtacatcaat gggcgtggat agcggtttga ctcacgggga    5220
tttccaagtc tccaccccat tgacgtcaat gggagtttgt tttggcacca aaatcaacgg    5280
gactttccaa aatgtcgtaa caactccgcc ccattgacgc aaatgggcgg taggcgtgta    5340
cggtgggagg tctatataag cagagctcgt ttagtgaacc gtcagatcgc ctggagacgc    5400
catccacgct gttttgacct ccatagaaga caccgggacc gatccagcct ccgcggccgg    5460
gaacggtgca ttggaacgcg gattccccgt gccaagagtg acgtaagtac cgcctataga    5520
gtctataggc ccaccccctt ggcttcttat gcatgctata ctgtttttgg cttggggtct    5580
atacaccccc gcttcctcat gttataggtg atggtatagc ttagcctata ggtgtgggtt    5640
attgaccatt attgaccact cccctattgg tgacgatact ttccattact aatccataac    5700
atggctcttt gccacaactc tctttattgg ctatatgcca atacactgtc cttcagagac    5760
tgacacggac tctgtatttt tacaggatgg ggtctcattt attatttaca aattcacata    5820
tacaacacca ccgtccccag tgcccgcagt ttttattaaa cataacgtgg gatctcacgc    5880
gaatctcggg tacgtgttcc ggacatgggc tcttctccgg tagcggcgga gcttctacat    5940
ccgagccctg ctcccatgcc tccagcgact catggtcgct cggcagctcc ttgctcctaa    6000
cagtggaggc cagacttagg cacagcacga tgcccaccac caccagtgtg ccgcacaagg    6060
ccgtggcggt agggtatgtg tctgaaaatg agctcgggga gcgggcttgc accgctgacg    6120
catttggaag acttaaggca gcggcagaag aagatgcagg cagctgagtt gttgtgttct    6180
gataagagtc agaggtaact cccgttgcgg tgctgttaac ggtggagggc agtgtagtct    6240
gagcagtact cgttgctgcc gcgcgcgcca ccagacataa tagctgacag actaacagac    6300
tgttcctttc catgggtctt ttctgcagtc accgtccttg acacgaagct taagccgcca    6360
ccatgggatg gagctgtatc atcctcttct tggtagcaac agctacaggc gtgcactccg    6420
acatccagat gacccagtct ccgtcctccc tgtctgcttt gtgggagac ggagtcacca     6480 tgacttgttg ggcaagtcag agtatcaacg actatttaaa ttggtatcac cagaggccag    6540
gggaggcccc tgagctcctg gtctttgctg cctccaattt gcaaattgga gtcccgtcaa    6600
ggttcagggg cagtggatct gagacgtatt tcactttaac tatcaacagt ctgcaacctg    6660
```

```
aagatagtgg cacatacttc tgtcagaatg ctcactcttt cccgcttact ttcggcggag   6720
ggaccaagct cgagatcaaa cgtacggtgg ctgcaccatc tgtcttcatc ttcccgccat   6780
ctgatgagca gttgaaatct ggaactgcct ctgttgtgtg cctgctgaat aacttctatc   6840
ccagagaggc caaagtacag tggaaggtgg ataacgccct ccaatcgggt aactcccagg   6900
agagtgtcac agagcaggac agcaaggaca gcacctacag cctcagcagc accctgacgc   6960
tgagcaaagc agactacgag aaacacaaag tctacgcctg cgaagtcacc catcagggcc   7020
tgagctcgcc cgtcacaaag agcttcaaca ggggagagtg ttaggaattc attgatcata   7080
atcagccata ccacatttgt agaggtttta cttgctttaa aaaacctccc acacctcccc   7140
ctgaacctga aacataaaat gaatgcaatt gttgttgtta acttgtttat tgcagcttat   7200
aatggttaca aataaagcaa tagcatcaca aatttcacaa ataaagcatt tttttcactg   7260
cattctagtt gtggtttgtc caaactcatc aatgtatctt atcatgtctg gcggccgccg   7320
atatttgaaa atatggcata ttgaaaatgt cgccgatgtg agtttctgtg taactgatat   7380
cgccattttt ccaaaagtga ttttgggca tacgcgatat ctggcgatag cgcttatatc   7440
gtttacgggg gatggcgata gacgactttg gtgacttggg cgattctgtg tgtcgcaaat   7500
atcgcagttt cgatataggt gacagacgat atgaggctat atcgccgata gaggcgacat   7560
caagctggca catggccaat gcatatcgat ctatacattg aatcaatatt ggccattagc   7620
catattattc attggttata tagcataaat caatattggc tattggccat gcatacgtt    7680 gtatccatat cataatatgt acatttatat tggctcatgt ccaacattac cgccatgttg   7740
acattgatta ttgactagtt attaatagta atcaattacg gggtcattag ttcatagccc   7800
atatatggag ttccgcgtta cataacttac ggtaaatggc ccgcctggct gaccgcccaa   7860
cgacccccgc ccattgacgt caataatgac gtatgttccc atagtaacgc caatagggac   7920
tttccattga cgtcaatggg tggagtattt acggtaaact gcccacttgg cagtacatca   7980
agtgtatcat atgccaagta cgccccctat tgacgtcaat gacggtaaat ggcccgcctg   8040
gcattatgcc cagtacatga ccttatggga ctttcctact tggcagtaca tctacgtatt   8100
agtcatcgct attaccatgg tgatgcggtt ttggcagtac atcaatgggc gtggatagcg   8160
gtttgactca cggggatttc caagtctcca ccccattgac gtcaatggga gtttgttttg   8220
gcaccaaaat caacgggact ttccaaaatg tcgtaacaac tccgccccat tgacgcaaat   8280
gggcggtagg cgtgtacggt gggaggtcta taagcaga gctcgtttag tgaaccgtca    8340
gatcgcctgg agacgccatc cacgctgttt tgacctccat agaagacacc gggaccgatc   8400
cagcctccgc ggccgggaac ggtgcattgg aacgcggatt ccccgtgcca agagtgacgt   8460
aagtaccgcc tatagagtct ataggcccac ccccttggct tcttatgcat gctatactgt   8520
ttttggcttg gggtctatac accccgctt cctcatgtta taggtgatgg tatagcttag    8580
cctataggtg tgggttattg accattattg accactcccc tattggtgac gatactttcc   8640
attactaatc cataacatgg ctctttgcca caactctctt tattggctat atgccaatac   8700
actgtccttc agagactgac acggactctg tattttaca ggatgggtc tcatttatta     8760 tttacaaatt cacatataca acaccaccgt ccccagtgcc cgcagttttt attaaacata   8820
acgtgggatc tccacgcgaa tctcgggtac gtgttccgga catgggctct ctctccggtag  8880 cggcggagct tctacatccg agccctgctc ccatgcctcc agcgactcat ggtcgctcgg   8940
cagctccttg ctcctaacag tggaggccag acttaggcac agcacgatgc ccaccaccac   9000
cagtgtgccg cacaaggccg tggcggtagg gtatgtgtct gaaaatgagc tcggggagcg   9060
```

```
ggcttgcacc gctgacgcat ttggaagact taaggcagcg gcagaagaag atgcaggcag   9120
ctgagttgtt gtgttctgat aagagtcaga ggtaactccc gttgcggtgc tgttaacggt   9180
ggagggcagt gtagtctgag cagtactcgt tgctgccgcg cgcgccacca gacataatag   9240
ctgacagact aacagactgt tcctttccat gggtcttttc tgcagtcacc gtccttgaca   9300
cgaagcttaa gccgccacca tgggatggag ctgtatcatc ctcttcttgg tagcaacagc   9360
tacaggcgcg cactcccaag tcactttgaa ggagtctggt cctacgctgg tgaaacccac   9420
acagaccctc acgctgacct gcagcttctc tgggttctca ctcagcacta gtggagtggg   9480
tgtgggctgg gtccgtcagc ccccaggaaa ggccctggag tggcttgcat tcatttggtg   9540
ggatgatgat aagtactaca gcccgtctct ggagagcagg ctcaccatca ccaaggacac   9600
ctccaaaaac caggtggtcc ttacaatgac caacatggac cctgtggaca cagccacata   9660
ttactgtgca cgatccgctg atgactatct ttactattct tttgacacgt ggggccaggg   9720
aaccctggtc accgtctcct cagcctccac caagggccca tcggtcttcc ccctggcacc   9780
ctcctccaag agcacctctg gggcacagc ggcctgggc tgcctggtca aggactactt   9840
ccccgaaccg gtgacggtgt cgtggaactc aggcgccctg accagcggcg tgcacacctt   9900
cccggctgtc ctacagtcct caggactcta ctccctcagc agcgtggtga ccgtgccctc   9960
cagcagcttg ggcacccaga cctacatctg caacgtgaat cacaagccca gcaacaccaa  10020
ggtggacaag agagttggtg agaggccagc acagggaggg aggtgtctg ctggaagcca  10080 ggctcagcgc tcctgcctgg acgcatcccg gctatgcagt cccagtccag ggcagcaagg  10140
caggccccgt ctgcctcttc acccggaggc ctctgcccgc cccactcatg ctcagggaga  10200
gggtcttctg gcttttcccc caggctctgg gcaggcacag gctaggtgcc cctaacccag  10260
gccctgcaca caaggggca ggtgctgggc tcagacctgc caagagccat atccgggagg  10320
accctgcccc tgacctaagc ccaccccaaa ggccaaactc tccactccct cagctcggac  10380
accttctctc ctcccagatt ccagtaactc ccaatcttct ctctgcagag cccaaatctt  10440
gtgacaaaac tcacacatgc ccaccgtgcc caggtaagcc agcccaggcc tcgccctcca  10500
gctcaaggcg ggacaggtgc cctagagtag cctgcatcca gggacaggcc ccagccgggt  10560
gctgacacgt ccacctccat ctcttcctca gcacctgaac tcctgggggg accgtcagtc  10620
ttcctcttcc ccccaaaacc caaggacacc ctcatgatct cccggacccc tgaggtcaca  10680
tgcgtggtgg tggacgtgag ccacgaagac cctgaggtca agttcaactg gtacgtggac  10740
ggcgtggagg tgcataatgc caagacaaag ccgcgggagg agcagtacaa cagcacgtac  10800
cgtgtggtca gcgtcctcac cgtcctgcac caggactggc tgaatggcaa ggagtacaag  10860
tgcaaggtct ccaacaaagc cctcccagcc cccatcgaga aaaccatctc caaagccaaa  10920
ggtgggaccc gtggggtgcg agggccacat ggacagaggc cggctcggcc cacccttgc  10980 cctgagagtg accgctgtac caacctctgt ccctacaggg cagccccgag aaccacaggt  11040
gtacaccctg cccccatccc gggaggagat gaccaagaac caggtcagcc tgacctgcct  11100
ggtcaaaggc ttctatccca gcgacatcgc cgtggagtgg gagagcaatg ggcagccgga  11160
gaacaactac aagaccacgc ctcccgtgct ggactccgac ggctccttct tcctctatag  11220
caagctcacc gtggacaaga gcaggtggca gcagggaac gtcttctcat gctccgtgat  11280
gcatgaggct ctgcacaacc actacacgca gaagagcctc tccctgtctc cgggtaaata  11340
ggaattcatt gatcataatc agccatacca catttgtaga ggttttactt gctttaaaaa  11400
acctcccaca cctcccctg aacctgaaac ataaaatgaa tgcaattgtt gttgttaact  11460
```

```
tgtttattgc agcttataat ggttacaaat aaagcaatag catcacaaat ttcacaaata    11520
aagcattttt ttcactgcat tctagttgtg gtttgtccaa actcatcaat gtatcttatc    11580
atgtctggat cctctacgcc ggacgcatcg tggccggcat caccggcgcc acaggtgcgg    11640
ttgctggcgc ctatatcgcc gacatcaccg atggggaaga tcgggctcgc cacttcgggc    11700
tcatgagcgc ttgtttcggc gtgggtatgg tggcaggccc cgtggccggg ggactgttgg    11760
gcgccatctc cttgcatgca ccattccttg cggcggcggt gctcaacggc ctcaacctac    11820
tactgggctg cttcctaatg caggagtcgc ataaggggaga gcgtcgacct cgggccgcgt    11880
tgctggcgtt tttccatagg ctccgccccc ctgacgagca tcacaaaaat cgacgctcaa    11940
gtcagaggtg gcgaaacccg acaggactat aaagatacca ggcgtttccc cctggaagct    12000
ccctcgtgcg ctctcctgtt ccgaccctgc cgcttaccgg atacctgtcc gcctttctcc    12060
cttcgggaag cgtggc                                                    12076
```

<210> SEQ ID NO 51
<211> LENGTH: 7
<212> TYPE: PRT
<213> ORGANISM: Artificial Sequence
<220> FEATURE:
<223> OTHER INFORMATION: Human VH CDR1

<400> SEQUENCE: 51

Thr Ser Gly Met Cys Val Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Human VH CDR1

<400> SEQUENCE: 52

Thr Ser Gly Val Ala Val Gly
1               5

<210> SEQ ID NO 53
<211> LENGTH: 7
<212> TYPE: PRT
<213> ORGANISM: Artificial Sequence
<220> FEATURE:
<223> OTHER INFORMATION: Human VH CDR1

<400> SEQUENCE: 53

Thr Ser Gly Val Ser Val Gly
1               5

<210> SEQ ID NO 54
<211> LENGTH: 7
<212> TYPE: PRT
<213> ORGANISM: Artificial Sequence
<220> FEATURE:
<223> OTHER INFORMATION: Human VH CDR1

<400> SEQUENCE: 54

Thr Ser Gly Val Gly Val Gly
1               5

<210> SEQ ID NO 55
<211> LENGTH: 7
<212> TYPE: PRT
<213> ORGANISM: Artificial Sequence

```
<220> FEATURE:
<223> OTHER INFORMATION: Human VH CDR1

<400> SEQUENCE: 55

Thr Ser Gly Val Ala Val Asn
1               5

<210> SEQ ID NO 56
<211> LENGTH: 16
<212> TYPE: PRT
<213> ORGANISM: Artificial Sequence
<220> FEATURE:
<223> OTHER INFORMATION: Human VH CDR2

<400> SEQUENCE: 56

Leu Ile Tyr Trp Asp Asp Asp Lys Arg Tyr Asn Pro Ser Leu Arg Ser
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Human VH CDR2

<400> SEQUENCE: 57

Leu Ile Phe Trp Asp Asp Asp Lys His Tyr Ser Pro Ser Leu Lys Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Human VH CDR2

<400> SEQUENCE: 58

Leu Val Tyr Trp Asp Asp Asp Arg Arg Tyr Asn Pro Ser Leu Lys Asn
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Human VH CDR2

<400> SEQUENCE: 59

Leu Ile Tyr Trp Asp Asp Asp Lys Arg Tyr Ser Pro Ser Leu Lys Asn
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Human VH CDR2

<400> SEQUENCE: 60

Phe Ile Phe Trp Asp Asp Asp Lys Tyr Tyr Ser Pro Ser Leu Glu Ser
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Human VH CDR2
```

<400> SEQUENCE: 61

Val Ile Tyr Trp Asp Asp Arg Arg Tyr Ser Pro Ser Leu Ser Ser
1               5                   10                  15

<210> SEQ ID NO 62
<211> LENGTH: 12
<212> TYPE: PRT
<213> ORGANISM: Artificial Sequence
<220> FEATURE:
<223> OTHER INFORMATION: Human VH CDR3

<400> SEQUENCE: 62

Ser Tyr Asp Asp Tyr Leu Tyr Tyr Ala Leu Asp Tyr
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Human VH CDR3

<400> SEQUENCE: 63

Phe Tyr Asp Asp Tyr Leu Tyr Tyr Ala Leu Asp Tyr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Human VH CDR3

<400> SEQUENCE: 64

Ser Ala Asp Asp Tyr Leu Tyr Tyr Ala Leu Asp Tyr
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Human VH CDR3

<400> SEQUENCE: 65

Ser Gly Asp Asp Tyr Leu Tyr Tyr Ala Leu Asp Tyr
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Human VH CDR3

<400> SEQUENCE: 66

Ser Tyr Asp Asp Tyr Leu Met Tyr Ala Leu Asp Tyr
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Human VH CDR3

<400> SEQUENCE: 67

Ser Tyr Asp Asp Tyr Leu Tyr Tyr Ser Leu Asp Tyr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Human VH CDR3

<400> SEQUENCE: 68

Ser Tyr Asp Asp Tyr Leu Tyr Tyr Ala Phe Asp Tyr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Human VH CDR3

<400> SEQUENCE: 69

Ser Tyr Asp Asp Tyr Leu Tyr Tyr Ala Leu Asp Thr
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Human VH CDR3

<400> SEQUENCE: 70

Ser Ala Asp Asp Tyr Leu Tyr Tyr Ser Leu Asp Tyr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Human VH CDR3

<400> SEQUENCE: 71

Ser Ala Asp Asp Tyr Leu Tyr Tyr Ala Phe Asp Tyr
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Human VH CDR3

<400> SEQUENCE: 72

Ser Ala Asp Asp Tyr Leu Tyr Tyr Ser Phe Asp Tyr
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Human VH CDR3

<400> SEQUENCE: 73

Ser Ala Asp Asp Tyr Leu Tyr Tyr Ser Phe Asp Thr

```
<210> SEQ ID NO 74
<211> LENGTH: 12
<212> TYPE: PRT
<213> ORGANISM: Artificial Sequence
<220> FEATURE:
<223> OTHER INFORMATION: Human VL CDR1

<400> SEQUENCE: 74

Arg Ala Ser Gln Thr Ile Asp Ser Ser Tyr Leu Ala
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Human VL CDR1

<400> SEQUENCE: 75

Arg Ala Ser Gln Asp Ile Asp Asn Phe Leu Ala
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Human VL CDR1

<400> SEQUENCE: 76

Arg Ala Ser Gln Thr Ile Ser Ser Tyr Leu Asn
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Human VL CDR1

<400> SEQUENCE: 77

Arg Ala Ser Gln Ser Ile Ser Ile Tyr Leu Asn
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Human VL CDR1

<400> SEQUENCE: 78

Arg Ala Ser Gln Thr Ile Ser Asp Phe Leu Asn
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Human VL CDR1

<400> SEQUENCE: 79

Trp Ala Ser Gln Ser Ile Asn Asp Tyr Leu Asn
1               5                   10
```

```
<210> SEQ ID NO 80
<211> LENGTH: 7
<212> TYPE: PRT
<213> ORGANISM: Artificial Sequence
<220> FEATURE:
<223> OTHER INFORMATION: Human VL CDR2

<400> SEQUENCE: 80

Gly Ala Ser Ser Arg Ala Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Human VL CDR2

<400> SEQUENCE: 81

Lys Val Ser Ser Leu Arg Ser
1               5

<210> SEQ ID NO 82
<211> LENGTH: 7
<212> TYPE: PRT
<213> ORGANISM: Artificial Sequence
<220> FEATURE:
<223> OTHER INFORMATION: Human VL CDR2

<400> SEQUENCE: 82

Ala Ala Ser Ser Leu Glu Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Human VL CDR2

<400> SEQUENCE: 83

Ala Thr Ser Thr Leu Gln Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Human VL CDR2

<400> SEQUENCE: 84

Ala Ser Ser Asn Leu Gln Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Human VL CDR2

<400> SEQUENCE: 85

Ala Ala Ser Asn Leu Gln Ile
1               5

<210> SEQ ID NO 86
```

```
<211> LENGTH: 9
<212> TYPE: PRT
<213> ORGANISM: Artificial Sequence
<220> FEATURE:
<223> OTHER INFORMATION: Human VL CDR3

<400> SEQUENCE: 86

Gln Gln Tyr Ala Lys Ser Pro Ile Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Human VL CDR3

<400> SEQUENCE: 87

Gln Gln Thr Arg Arg Phe Pro Leu Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Human VL CDR3

<400> SEQUENCE: 88

Gln Gln Ala Asn Ser Phe Pro Leu Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Human VL CDR3

<400> SEQUENCE: 89

Gln Gln Thr Tyr Arg Asn Leu Phe Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Human VL CDR3

<400> SEQUENCE: 90

Gln Gln Thr Tyr Ser Thr Leu Gly Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Human VL CDR3

<400> SEQUENCE: 91

Gln Asn Gly His Ser Phe Pro Leu Thr
1               5

<210> SEQ ID NO 92
<211> LENGTH: 9
<212> TYPE: PRT
```

<213> ORGANISM: Artificial Sequence
<220> FEATURE:
<223> OTHER INFORMATION: Human VL CDR3

<400> SEQUENCE: 92

Gln Ser Gly His Ser Phe Pro Leu Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Human VL CDR3

<400> SEQUENCE: 93

Gln His Gly His Ser Phe Pro Leu Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Human VL CDR3

<400> SEQUENCE: 94

Gln Leu Gly His Ser Phe Pro Leu Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Human VL CDR3

<400> SEQUENCE: 95

Gln Asn Ala His Ser Phe Pro Leu Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Human VL CDR3

<400> SEQUENCE: 96

Gln Asn Gly Trp Ser Phe Pro Leu Thr
1               5

<210> SEQ ID NO 97
<211> LENGTH: 16
<212> TYPE: PRT
<213> ORGANISM: Artificial Sequence
<220> FEATURE:
<223> OTHER INFORMATION: Human VH CDR2

<400> SEQUENCE: 97

Leu Ile Tyr Trp Asp Asp Asp Lys Arg Tyr Ser Pro Ser Leu Glu Thr
1               5                   10                  15

<210> SEQ ID NO 98
<211> LENGTH: 12
<212> TYPE: PRT
<213> ORGANISM: Artificial Sequence
<220> FEATURE:

```
<223> OTHER INFORMATION: Human VH CDR3

<400> SEQUENCE: 98

Ser His Asp Asp Tyr Leu Tyr Tyr Ala Leu Asp Tyr
1               5                   10

<210> SEQ ID NO 99
<211> LENGTH: 7
<212> TYPE: PRT
<213> ORGANISM: Artificial Sequence
<220> FEATURE:
<221> NAME/KEY: source
<222> LOCATION: 1..7
<223> OTHER INFORMATION: CDR1 of identified human VH consensus sequence
<220> FEATURE:
<221> NAME/KEY: misc_feature
<222> LOCATION: 4,5,7
<223> OTHER INFORMATION: Positions with consensus residues, meaning any
      amino acid

<400> SEQUENCE: 99

Thr Ser Gly Xaa Xaa Val Xaa
1               5

<210> SEQ ID NO 100
<211> LENGTH: 16
<212> TYPE: PRT
<213> ORGANISM: Artificial Sequence
<220> FEATURE:
<221> NAME/KEY: source
<222> LOCATION: 1..16
<223> OTHER INFORMATION: CDR2 of identified human VH consensus sequence
<220> FEATURE:
<221> NAME/KEY: misc_feature
<222> LOCATION: 1,2,3,8,9,11,15,16
<223> OTHER INFORMATION: Positions with consensus residues, meaning any
      amino acid

<400> SEQUENCE: 100

Xaa Xaa Xaa Trp Asp Asp Asp Xaa Xaa Tyr Xaa Pro Ser Leu Xaa Xaa
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Human VH CDR2

<400> SEQUENCE: 101

Phe Ile Trp Trp Asp Asp Asp Lys Tyr Tyr Ser Pro Ser Leu Glu Ser
1               5                   10                  15
```